（12）United States Patent
Van Delft et al.

(10) Patent No.: US 10,072,096 B2
(45) Date of Patent: Sep. 11, 2018

(54) MODIFIED GLYCOPROTEIN, PROTEIN-CONJUGATE AND PROCESS FOR THE PREPARATION THEREOF

(71) Applicant: SynAffix B.V., Oss (NL)

(72) Inventors: Floris Louis Van Delft, Nijmegen (NL); Remon Van Geel, Lith-Oijen (NL); Maria Antonia Wijdeven, Lent (NL); Jorge Merijn Mathieu Verkade, Eindhoven (NL); Ryan Heesbeen, Nijmegen (NL)

(73) Assignee: SYNAFFIX B.V., Oss (NL)

( * ) Notice: Subject to any disclaimer, the term of this patent is extended or adjusted under 35 U.S.C. 154(b) by 9 days.

(21) Appl. No.: 15/029,123

(22) PCT Filed: Oct. 14, 2014

(86) PCT No.: PCT/NL2014/050714
§ 371 (c)(1),
(2) Date: Apr. 13, 2016

(87) PCT Pub. No.: WO2015/057063
PCT Pub. Date: Apr. 23, 2015

(65) Prior Publication Data
US 2016/0280797 A1 Sep. 29, 2016

(30) Foreign Application Priority Data

Oct. 14, 2013 (EP) .................... 13188514
Oct. 14, 2013 (EP) .................... 13188585
Apr. 23, 2014 (EP) .................... 14165563
Apr. 23, 2014 (EP) .................... 14165581

(51) Int. Cl.
*C07K 16/40* (2006.01)
*C12P 21/00* (2006.01)
*C07K 16/32* (2006.01)
*A61K 47/68* (2017.01)

(52) U.S. Cl.
CPC .......... *C07K 16/40* (2013.01); *A61K 47/6871* (2017.08); *C07K 16/32* (2013.01); *C12P 21/00* (2013.01); *C12P 21/005* (2013.01); *C07K 2317/41* (2013.01)

(58) Field of Classification Search
CPC .... C07K 16/40; C07K 16/32; A61K 47/6871; C12P 21/00; C12P 21/005
See application file for complete search history.

(56) References Cited

FOREIGN PATENT DOCUMENTS

| WO | WO-2004/063344 A2 | 7/2004 |
| WO | WO-2007/095506 A1 | 8/2007 |
| WO | WO-2008/029281 A2 | 3/2008 |
| WO | WO-2009/025646 A1 | 2/2009 |
| WO | WO-2009/102820 A2 | 8/2009 |
| WO | WO-2013/037824 A1 | 3/2013 |
| WO | WO-2014/065661 A1 | 5/2014 |

OTHER PUBLICATIONS

Abbas et al., "Allenamides as orthogonal handles for selective modification of cysteine in peptides and proteins", Angew. Chem. Int. Ed., 2014, vol. 53, pp. 7491-7494.
Agnew et al., "Evaluating options for hard to label antibodies", Life Technologies/ ABRF ARG User's Study: 2012-2013, Apr. 2013, pp. 1-12, retrieved from the Internet: URL: http://www.abrforg.Other/ABRFMeetings/ABRF2013/RG%20presentations/RG3_ARG_Agnew.pdf.
Baisch et al., "Convenient chemoenzymatic synthesis of beta-purine-diphosphate sugars (GDP-fucose-analogues)", Bioorganic & Medicinal Chemistry, 1997, vol. 5, No. 2, pp. 383-391.
Bojarova et al., "Synthesis of LacdiNAc-terminated glycoconjugates by mutant galactosyltransferase—A way to new glycodrugs and materials", Glycobiology, 2009, vol. 19, No. 5, pp. 509-517.
Brik et al., "Sugar-assisted ligation for the synthesis of glycopeptides", Chemistry—A European Journal, 2007, vol. 13, pp. 5670-5675.
Clark et al., "Direct in-gel fluorescence detection and cellular imaging of O—GlcNAc-modified proteins", Journal of the American Chemical Society, 2008, vol. 130, pp. 11576-11577.

(Continued)

*Primary Examiner* — Paul J Holland
(74) *Attorney, Agent, or Firm* — Gilberto M. Villacorta; Sunit Talapatra; Foley & Lardner LLP

(57) ABSTRACT

The invention relates to a glycoprotein comprising an optionally fucosylated glycan according to formula (105) or (106), wherein Su(A)x is a modified sugar moiety comprising one or more functional groups A. Functional group A is independently selected from the group consisting of a thiol group, a halogen, a sulfonyloxy group, a halogenated acetamido group, a mercaptoacetamido group and a sulfonated hydroxyacetamido group. The invention also relates to a glycoprotein-conjugate wherein a glycoprotein according to the invention is conjugated to a molecule of interest. Said molecule of interest may for example be an active substance. The invention further relates to a process for the preparation of a modified glycoprotein, and to a method for the preparation of a glycoprotein-conjugate. The invention particularly relates to modified antibodies, antibody-conjugates, antibody-drug conjugates and methods for the preparation thereof.

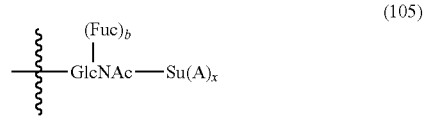

(105)

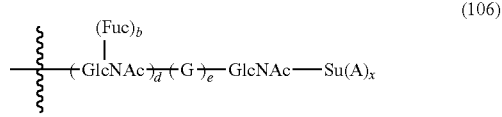

(106)

15 Claims, 12 Drawing Sheets
Specification includes a Sequence Listing.

(56) References Cited

OTHER PUBLICATIONS

Davis et al., "An endoglycosidase with alternative glycan specificity allows broadened glycoprotein remodelling" Journal of the American Chemical Society, 2012, vol. 134, pp. 8030-8033.

Elling et al., "Chemoenzymatic synthesis of biotinylated nucleotide sugars as substrates for glycosyltransferases", Chembiochem, 2001, vol. 2, pp. 884-894.

Finn et al., "Analysis and optimization of copper-catalyzed azide-slkyne cycloaddition for bioconjugation", Angew. Chem. Int. Ed., 2009, vol. 48, pp. 9879-9883.

International Search Report issued in International Patent Application No. PCT/NL2014/050714, dated Feb. 17, 2015.

Kim et al., "Chemical arsenal for the study of O—GlcNAC", Molecules, 2011, vol. 16, pp. 1987-2022.

Kunz et al., "Synthetic vaccines of tumor-associated glycopeptide antigens by immune-compatible thioether linkage to bovine serum albumin", Angew. Chem. Int. Ed., 2007, vol. 46, pp. 5226-5230.

Mercer et al., "Use of novel mutant Galactosyltransferase for the bioconjugation of terminal N-Acetylglucosamine (GlcNAc) residues on live cell surface", Bioconjugate Chemistry, 2013, vol. 24, pp. 144-152.

Okeley et al., "Metabolic engineering of monoclonal antibody carbohydrates for antibody-drug conjugation", Bioconjugate Chemistry, 2013, vol. 24, pp. 1650-1655.

Olsen et al., "EndoS, a novel secreted protein from *Streptococcus pyogenes* with endoglycosidase activity on human IgG", The EMBO Journal, 2001, vol. 20, No. 12, pp. 3046-3055.

Pannecoucke et al., "6-Azido D-galactose transfer to N-acetyl-D-glucosamine derivative using commercially available beta-1, 4-galactosyltransferase", Tetrahedron Letters, 2009, vol. 49, pp. 2294-2297.

Pouilly et al., "Evaluation of analogues of GalNAc as substrates for enzymes of the mammalian GalNAc salvage pathway", Acs Chemical Biology, 2012, vol. 7, pp. 753-760.

Qasba et al., "Site specific conjugation of fluoroprobes to the remodeled Fc N-Glycans of monoclonal antibodies using mutant glycosyltransferases: Application for cell surface antigen detection", Bioconjugate Chemistry, 2009, vol. 20, pp. 1228-1236.

Qasba et al., "Site-specific linking of biomolecules via glycan residues using glycosyltransferases", Biotechnology Progress, 2008, vol. 24, pp. 520-526.

Qasba et al., "Structure-based design of beta-1, 4-galactosyltransferase I (beta-4Gal-T1) with equally efficient N-acetylgalactosaminylstransferase activity", The Journal of Biological Chemistry, Jun. 2002, vol. 277, No. 23, pp. 20833-20839.

Qasba et al., "Studies on the metal binding sites in the catalytic domain of beta-1, 4-galactosyltransferase", Glycobiology, 2002, vol. 12, No. 7, pp. 395-407.

Qasba et al., "The N-terminal stem region of bovine and human beta-1, 4-galactosyltransferase I increase the in vitro folding efficiency of their catalytic domain from inclusion bodies", Protein Expression and Purification, 2003, vol. 30, pp. 219-229.

Qu et al., "Carbohydrates engineered at antibody constant domains can be used for site-specific conjugation of drugs and chelates", Journal of Immunological Methods, 1998, vol. 213, pp. 131-144.

Satoh et al., "Comparison of biological activity among nonfucosylated therapeutic IgG1 antibodies with three different N-linked Fc oligosaccharides: the high-mannose, hybrid, and complex types", Glycobiology, 2006, vol. 17, No. 1, pp. 104-118.

Shabat et al., "Self-immolative dendrimers: a distinctive approach to molecular amplification", Soft Matters, 2010, vol. 6, pp. 1073-1080.

Sharma et al., "Design and synthesis of LNA based mercaptoacetamido-linked nucleoside dimmers", Carbohydrate News Letters (India), Dec. 2013, vol. 14, p. 15, poster abstract.

Wang et al., "Chemoenzymatic glycoengineering of intact IgG antibodies for gain of functions", Journal of the American Chemical Society, 2012, vol. 134, pp. 12308-12318.

Wang et al., "Highly efficient synthesis of UDP-GalNAc/GlcNAc analogues with promiscuous recombinant human UDP-GalNAc pyrophosphorylase AGX1", Chemistry A European Journal, 2010, vol. 16, pp. 13343-13345.

Wong et al., "Enzymes in the synthesis of glycoconjugates", Chemical Reviews, 2011, vol. 111, pp. 4529-4307.

Zeglis et al., "Enzyme-mediated methodology for the site-specific radiolabeling of antibodies based on catalyst-free click chemistry", Bioconjugate Chemistry, 2013, vol. 24, pp. 1057-1067.

SEQUENCE LISTING

```
<160> NUMBER OF SEQ ID NOS: 24

<210> SEQ ID NO 1
<211> LENGTH: 39
<212> TYPE: DNA
<213> ORGANISM: artificial
<220> FEATURE:
<223> OTHER INFORMATION: primer sequence

<400> SEQUENCE: 1
cagcgacata tgtcgctgac cgcatgccct gaggagtcc                        39

<210> SEQ ID NO 2
<211> LENGTH: 36
<212> TYPE: DNA
<213> ORGANISM: artificial
<220> FEATURE:
<223> OTHER INFORMATION: primer sequence

<400> SEQUENCE: 2
gacacctcca aagttctgca cgtaaggtag gctaaa                           36

<210> SEQ ID NO 3
<211> LENGTH: 39
<212> TYPE: DNA
<213> ORGANISM: artificial
<220> FEATURE:
<223> OTHER INFORMATION: primer sequence

<400> SEQUENCE: 3
```

```
ctgatggatg gatccctagc tcggcgtccc gatgtccac                    39

<210> SEQ ID NO 4
<211> LENGTH: 36
<212> TYPE: DNA
<213> ORGANISM: artificial
<220> FEATURE:
<223> OTHER INFORMATION: primer sequence

<400> SEQUENCE: 4
ccttacgtgc agaactttgg aggtgtctct gctcta                       36

<210> SEQ ID NO 5
<211> LENGTH: 36
<212> TYPE: DNA
<213> ORGANISM: artificial
<220> FEATURE:
<223> OTHER INFORMATION: primer sequence

<400> SEQUENCE: 5
gacacctcca aaaaactgca cgtaaggtag gctaaa                       36

<210> SEQ ID NO 6
<211> LENGTH: 36
<212> TYPE: DNA
<213> ORGANISM: artificial
<220> FEATURE:
<223> OTHER INFORMATION: primer sequence

<400> SEQUENCE: 6
ccttacgtgc agtttttttgg aggtgtctct gctcta                      36

<210> SEQ ID NO 7
<211> LENGTH: 36
<212> TYPE: DNA
<213> ORGANISM: artificial
<220> FEATURE:
<223> OTHER INFORMATION: primer sequence

<400> SEQUENCE: 7
gacacctcca aacatctgca cgtaaggtag gctaaa                       36

<210> SEQ ID NO 8
<211> LENGTH: 36
<212> TYPE: DNA
<213> ORGANISM: artificial
<220> FEATURE:
<223> OTHER INFORMATION: primer sequence

<400> SEQUENCE: 8
ccttacgtgc agatgtttgg aggtgtctct gctcta                       36

<210> SEQ ID NO 9
<211> LENGTH: 36
<212> TYPE: DNA
<213> ORGANISM: artificial
<220> FEATURE:
<223> OTHER INFORMATION: primer sequence

<400> SEQUENCE: 9
gacacctcca aaaatctgca cgtaaggtag gctaaa                       36

<210> SEQ ID NO 10
<211> LENGTH: 36
<212> TYPE: DNA
```

```
<213> ORGANISM: artificial
<220> FEATURE:
<223> OTHER INFORMATION: primer sequence

<400> SEQUENCE: 10
ccttacgtgc agattttttgg aggtgtctct gctcta                              36

<210> SEQ ID NO 11
<211> LENGTH: 36
<212> TYPE: DNA
<213> ORGANISM: artificial
<220> FEATURE:
<223> OTHER INFORMATION: primer sequence

<400> SEQUENCE: 11
gacacctcca aacacctgca cgtaaggtag gctaaa                               36

<210> SEQ ID NO 12
<211> LENGTH: 36
<212> TYPE: DNA
<213> ORGANISM: artificial
<220> FEATURE:
<223> OTHER INFORMATION: primer sequence

<400> SEQUENCE: 12
ccttacgtgc aggtgtttgg aggtgtctct gctcta                               36

<210> SEQ ID NO 13
<211> LENGTH: 36
<212> TYPE: DNA
<213> ORGANISM: artificial
<220> FEATURE:
<223> OTHER INFORMATION: primer sequence

<400> SEQUENCE: 13
gacacctcca aacgcctgca cgtaaggtag gctaaa                               36

<210> SEQ ID NO 14
<211> LENGTH: 36
<212> TYPE: DNA
<213> ORGANISM: artificial
<220> FEATURE:
<223> OTHER INFORMATION: primer sequence

<400> SEQUENCE: 14
ccttacgtgc aggcgtttgg aggtgtctct gctcta                               36

<210> SEQ ID NO 15
<211> LENGTH: 36
<212> TYPE: DNA
<213> ORGANISM: artificial
<220> FEATURE:
<223> OTHER INFORMATION: primer sequence

<400> SEQUENCE: 15
gacacctcca aagccctgca cgtaaggtag gctaaa                               36

<210> SEQ ID NO 16
<211> LENGTH: 36
<212> TYPE: DNA
<213> ORGANISM: artificial
<220> FEATURE:
<223> OTHER INFORMATION: primer sequence

<400> SEQUENCE: 16
ccttacgtgc agggctttgg aggtgtctct gctcta                               36
```

<210> SEQ ID NO 17
<211> LENGTH: 402
<212> TYPE: PRT
<213> ORGANISM: Bos taurus

<400> SEQUENCE: 17

```
Met Lys Phe Arg Glu Pro Leu Gly Gly Ser Ala Ala Met Pro Gly
1               5                   10                  15

Ala Ser Leu Gln Arg Ala Cys Arg Leu Val Ala Val Cys Ala Leu
                20                  25                  30

His Leu Gly Val Thr Leu Val Tyr Tyr Leu Ala Gly Arg Asp Leu Arg
                35                  40                      45

Arg Leu Pro Gln Leu Val Gly Val His Pro Leu Gln Gly Ser Ser
        50                  55                  60

His Gly Ala Ala Ala Ile Gly Gln Pro Ser Gly Glu Leu Arg Leu Arg
65                      70                  75                  80

Gly Val Ala Pro Pro Pro Leu Gln Asn Ser Ser Lys Pro Arg Ser
                    85                  90                  95

Arg Ala Pro Ser Asn Leu Asp Ala Tyr Ser His Pro Gly Pro Gly Pro
                100                 105                 110

Gly Pro Gly Ser Asn Leu Thr Ser Ala Pro Val Pro Ser Thr Thr Thr
                115                 120                 125

Arg Ser Leu Thr Ala Cys Pro Glu Glu Ser Pro Leu Leu Val Gly Pro
        130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Leu Phe Arg Asn Arg Gln
                180                 185                 190

Glu His Leu Lys Tyr Trp Leu Tyr Tyr Leu His Pro Met Val Gln Arg
                195                 200                 205

Gln Gln Leu Asp Tyr Gly Ile Tyr Val Ile Asn Gln Ala Gly Glu Ser
        210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                    245                 250                 255

Pro Met Asn Asp His Asn Thr Tyr Arg Cys Phe Ser Gln Pro Arg His
                260                 265                 270

Ile Ser Val Ala Met Asp Lys Phe Gly Phe Ser Leu Pro Tyr Val Gln
                275                 280                 285

Tyr Phe Gly Gly Val Ser Ala Leu Ser Lys Gln Gln Phe Leu Ser Ile
        290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                    325                 330                 335

Ala Val Ile Gly Lys Cys Arg Met Ile Arg His Ser Arg Asp Lys Lys
                340                 345                 350

Asn Glu Pro Asn Pro Gln Arg Phe Asp Arg Ile Ala His Thr Lys Glu
                355                 360                 365

Thr Met Leu Ser Asp Gly Leu Asn Ser Leu Thr Tyr Met Val Leu Glu
```

```
                 370                 375                 380
Val Gln Arg Tyr Pro Leu Tyr Thr Lys Ile Thr Val Asp Ile Gly Thr
385                 390                 395                 400

Pro Ser

<210> SEQ ID NO 18
<211> LENGTH: 402
<212> TYPE: PRT
<213> ORGANISM: artificial
<220> FEATURE:
<223> OTHER INFORMATION: bos taurus GalT Y289N

<400> SEQUENCE: 18

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
                20                  25                  30

His Leu Gly Val Thr Leu Val Tyr Tyr Leu Ala Gly Arg Asp Leu Arg
            35                  40                  45

Arg Leu Pro Gln Leu Val Gly Val His Pro Pro Leu Gln Gly Ser Ser
        50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
                100                 105                 110

Gly Pro Gly Ser Asn Leu Thr Ser Ala Pro Val Pro Ser Thr Thr Thr
            115                 120                 125

Arg Ser Leu Thr Ala Cys Pro Glu Glu Ser Pro Leu Val Gly Pro
        130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
                180                 185                 190

Glu His Leu Lys Tyr Trp Leu Tyr Tyr Leu His Pro Met Val Gln Arg
            195                 200                 205

Gln Gln Leu Asp Tyr Gly Ile Tyr Val Ile Asn Gln Ala Gly Glu Ser
        210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
                260                 265                 270

Ile Ser Val Ala Met Asp Lys Phe Gly Phe Ser Leu Pro Tyr Val Gln
            275                 280                 285

Asn Phe Gly Gly Val Ser Ala Leu Ser Lys Gln Gln Phe Leu Ser Ile
        290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335
```

Ala Val Ile Gly Lys Cys Arg Met Ile Arg His Ser Arg Asp Lys Lys
             340                 345                 350

Asn Glu Pro Asn Pro Gln Arg Phe Asp Arg Ile Ala His Thr Lys Glu
            355                 360                 365

Thr Met Leu Ser Asp Gly Leu Asn Ser Leu Thr Tyr Met Val Leu Glu
    370                 375                 380

Val Gln Arg Tyr Pro Leu Tyr Thr Lys Ile Thr Val Asp Ile Gly Thr
385                 390                 395                 400

Pro Ser

<210> SEQ ID NO 19
<211> LENGTH: 402
<212> TYPE: PRT
<213> ORGANISM: artificial
<220> FEATURE:
<223> OTHER INFORMATION: bos taurus GalT Y289F

<400> SEQUENCE: 19

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
        115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
        275                 280                 285

-continued

```
Phe Phe Gly Gly Val Ser Ala Leu Ser Lys Gln Gln Phe Leu Ser Ile
    290                 295                 300
Asn Gly Phe Pro Asn Asn Tyr Trp Gly Trp Gly Gly Glu Asp Asp Asp
305                 310                 315                 320
Ile Tyr Asn Arg Leu Ala Phe Arg Gly Met Ser Val Ser Arg Pro Asn
                325                 330                 335
Ala Val Ile Gly Lys Cys Arg Met Ile Arg His Ser Arg Asp Lys Lys
            340                 345                 350
Asn Glu Pro Asn Pro Gln Arg Phe Asp Arg Ile Ala His Thr Lys Glu
        355                 360                 365
Thr Met Leu Ser Asp Gly Leu Asn Ser Leu Thr Tyr Met Val Leu Glu
370                 375                 380
Val Gln Arg Tyr Pro Leu Tyr Thr Lys Ile Thr Val Asp Ile Gly Thr
385                 390                 395                 400
Pro Ser

<210> SEQ ID NO 20
<211> LENGTH: 402
<212> TYPE: PRT
<213> ORGANISM: artificial
<220> FEATURE:
<223> OTHER INFORMATION: bos taurus GalT Y289M

<400> SEQUENCE: 20

Met Lys Phe Arg Glu Pro Leu Leu Gly Gly Ser Ala Ala Met Pro Gly
1               5                   10                  15
Ala Ser Leu Gln Arg Ala Cys Arg Leu Leu Val Ala Val Cys Ala Leu
            20                  25                  30
His Leu Gly Val Thr Leu Val Tyr Tyr Leu Ala Gly Arg Asp Leu Arg
        35                  40                  45
Arg Leu Pro Gln Leu Val Gly Val His Pro Pro Leu Gln Gly Ser Ser
    50                  55                  60
His Gly Ala Ala Ala Ile Gly Gln Pro Ser Gly Glu Leu Arg Leu Arg
65                  70                  75                  80
Gly Val Ala Pro Pro Pro Leu Gln Asn Ser Ser Lys Pro Arg Ser
                85                  90                  95
Arg Ala Pro Ser Asn Leu Asp Ala Tyr Ser His Pro Gly Pro Gly Pro
                100                 105                 110
Gly Pro Gly Ser Asn Leu Thr Ser Ala Pro Val Pro Ser Thr Thr Thr
            115                 120                 125
Arg Ser Leu Thr Ala Cys Pro Glu Glu Ser Pro Leu Leu Val Gly Pro
    130                 135                 140
Met Leu Ile Glu Phe Asn Ile Pro Val Asp Leu Lys Leu Ile Glu Gln
145                 150                 155                 160
Gln Asn Pro Lys Val Lys Leu Gly Gly Arg Tyr Thr Pro Met Asp Cys
                165                 170                 175
Ile Ser Pro His Lys Val Ala Ile Ile Leu Phe Arg Asn Arg Gln
                180                 185                 190
Glu His Leu Lys Tyr Trp Leu Tyr Tyr Leu His Pro Met Val Gln Arg
            195                 200                 205
Gln Gln Leu Asp Tyr Gly Ile Tyr Val Ile Asn Gln Ala Gly Glu Ser
    210                 215                 220
Met Phe Asn Arg Ala Lys Leu Leu Asn Val Gly Phe Lys Glu Ala Leu
225                 230                 235                 240
Lys Asp Tyr Asp Tyr Asn Cys Phe Val Phe Ser Asp Val Asp Leu Ile
```

```
                        245                 250                 255
Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
        275                 280                 285

Met Phe Gly Gly Val Ser Ala Leu Ser Lys Gln Gln Phe Leu Ser Ile
    290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
        355                 360                 365

Thr Met Leu Ser Asp Gly Leu Asn Ser Leu Thr Tyr Met Val Leu Glu
    370                 375                 380

Val Gln Arg Tyr Pro Leu Tyr Thr Lys Ile Thr Val Asp Ile Gly Thr
385                 390                 395                 400

Pro Ser

<210> SEQ ID NO 21
<211> LENGTH: 402
<212> TYPE: PRT
<213> ORGANISM: artificial
<220> FEATURE:
<223> OTHER INFORMATION: bos taurus GalT Y289I

<400> SEQUENCE: 21

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
        115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Leu Phe Arg Asn Arg Gln
            180                 185                 190

Glu His Leu Lys Tyr Trp Leu Tyr Tyr Leu His Pro Met Val Gln Arg
        195                 200                 205
```

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                    245                 250                 255

Pro Met Asn Asp His Asn Thr Tyr Arg Cys Phe Ser Gln Pro Arg His
                260                 265                 270

Ile Ser Val Ala Met Asp Lys Phe Gly Phe Ser Leu Pro Tyr Val Gln
        275                 280                 285

Ile Phe Gly Gly Val Ser Ala Leu Ser Lys Gln Gln Phe Leu Ser Ile
        290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                    325                 330                 335

Ala Val Ile Gly Lys Cys Arg Met Ile Arg His Ser Arg Asp Lys Lys
                340                 345                 350

Asn Glu Pro Asn Pro Gln Arg Phe Asp Arg Ile Ala His Thr Lys Glu
            355                 360                 365

Thr Met Leu Ser Asp Gly Leu Asn Ser Leu Thr Tyr Met Val Leu Glu
        370                 375                 380

Val Gln Arg Tyr Pro Leu Tyr Thr Lys Ile Thr Val Asp Ile Gly Thr
385                 390                 395                 400

Pro Ser

<210> SEQ ID NO 22
<211> LENGTH: 402
<212> TYPE: PRT
<213> ORGANISM: artificial
<220> FEATURE:
<223> OTHER INFORMATION: bos taurus GalT Y289V

<400> SEQUENCE: 22

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
        115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
145                 150                 155                 160

```
Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
        275                 280                 285

Val Phe Gly Gly Val Ser Ala Leu Ser Lys Gln Gln Phe Leu Ser Ile
    290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
        355                 360                 365

Thr Met Leu Ser Asp Gly Leu Asn Ser Leu Thr Tyr Met Val Leu Glu
370                 375                 380

Val Gln Arg Tyr Pro Leu Tyr Thr Lys Ile Thr Val Asp Ile Gly Thr
385                 390                 395                 400

Pro Ser

<210> SEQ ID NO 23
<211> LENGTH: 402
<212> TYPE: PRT
<213> ORGANISM: artificial
<220> FEATURE:
<223> OTHER INFORMATION: bos taurus GalT Y289A

<400> SEQUENCE: 23

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
```

```
            115                 120                 125
Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
        275                 280                 285

Ala Phe Gly Gly Val Ser Ala Leu Ser Lys Gln Gln Phe Leu Ser Ile
    290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
        355                 360                 365

Thr Met Leu Ser Asp Gly Leu Asn Ser Leu Thr Tyr Met Val Leu Glu
    370                 375                 380

Val Gln Arg Tyr Pro Leu Tyr Thr Lys Ile Thr Val Asp Ile Gly Thr
385                 390                 395                 400

Pro Ser

<210> SEQ ID NO 24
<211> LENGTH: 402
<212> TYPE: PRT
<213> ORGANISM: artificial
<220> FEATURE:
<223> OTHER INFORMATION: bos taurus GalT Y289G

<400> SEQUENCE: 24

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
                20                  25                  30

His Leu Gly Val Thr Leu Val Tyr Tyr Leu Ala Gly Arg Asp Leu Arg
            35                  40                  45

Arg Leu Pro Gln Leu Val Gly Val His Pro Pro Leu Gln Gly Ser Ser
        50                  55                  60

His Gly Ala Ala Ala Ile Gly Gln Pro Ser Gly Glu Leu Arg Leu Arg
65                  70                  75                  80
```

```
Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
        115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
        275                 280                 285

Gly Phe Gly Gly Val Ser Ala Leu Ser Lys Gln Gln Phe Leu Ser Ile
    290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
        355                 360                 365

Thr Met Leu Ser Asp Gly Leu Asn Ser Leu Thr Tyr Met Val Leu Glu
    370                 375                 380

Val Gln Arg Tyr Pro Leu Tyr Thr Lys Ile Thr Val Asp Ile Gly Thr
385                 390                 395                 400

Pro Ser
```

MODIFIED GLYCOPROTEIN, PROTEIN-CONJUGATE AND PROCESS FOR THE PREPARATION THEREOF

CROSS-REFERENCE TO RELATED APPLICATIONS

This application is the National Phase of International Patent Application No. PCT/NL2014/050714, filed Oct. 14, 2014, published on Apr. 23, 2015 as WO 2015/057063 A1, which claims priority to European Patent Application No. 13188514.7, filed Oct. 14, 2013, European Patent Application No. 13188585.7, filed Oct. 14, 2013, European Patent Application No. 14165563.9, filed Apr. 23, 2014, and European Patent Application No. 14165581.1, filed Apr. 23, 2014. The contents of these applications are herein incorporated by reference in their entirety.

SEQUENCE LISTING

The instant application contains a Sequence Listing which has been submitted in ASCII format via EFS-WEB and is hereby incorporated by reference in its entirety. Said ASCII copy, created on Apr. 12, 2016, is named 069818-3590SequenceListing.txt and is 31 KB.

TECHNICAL FIELD OF THE INVENTION

The present invention relates to modified glycoproteins, in particular to glycoproteins comprising a modified sugar-moiety. The invention also relates to a glycoprotein-conjugate wherein a glycoprotein according to the invention is conjugated to a molecule of interest. Said molecule of interest may for example be a an active substance. The invention further relates to a process for the preparation of a modified glycoprotein, and to a method for the preparation of a glycoprotein-conjugate. The invention particularly relates to modified antibodies, antibody-conjugates, antibody-drug conjugates and methods for the preparation thereof.

BACKGROUND OF THE INVENTION

Protein conjugates, i.e. proteins conjugated to a molecule of interest via a linker, are known in the art. For example, fluorescent labeling is a powerful technique for in vitro and in vivo visualisation, covalent immobilization of proteins is a useful strategy for industrial application and PEGylation of proteins leads to significantly enhanced circulation time. In addition, there is great interest in antibody-conjugates wherein the molecule of interest is a drug, for example a cytotoxic chemical. Antibody-drug-conjugates are known in the art, and consist of a recombinant antibody covalently bound to a cytotoxic chemical via a synthetic linker. Protein conjugates known from the prior art are commonly prepared by conjugation of a functional group to the side chain of amino acid lysine or cysteine, by acylation or alkylation, respectively.

For lysines, conjugation takes place preferentially at lysine side chains with highest steric accessibility, the lowest pKa, or a combination thereof. Disadvantage of this method is that site-control of conjugation is low.

Better control of site-specificity is obtained by alkylation of cysteines, based on the fact that typically no or few free cysteines are present in a typical protein, thereby offering the option of alkylating only those cysteines that are already present in reduced form or selectively engineered into a protein. Alternatively, cysteines can be selectively liberated by a (partial) reductive step. For example, selective cysteine liberation by reduction is typically performed by treatment of a protein with a reducing agent (e.g. TCEP or DTT), leading to conversion of a disulfide bond into two free thiols. The liberated thiols can then be alkylated with an electrophilic reagent, typically based on a maleimide chemistry, which generally proceeds fast and with high selectivity, or with haloacetamides, which also show strong preference for cysteine but side-reactions with lysine side-chains may be encountered.

A recent report (N. M. Okeley et al., *Bioconj. Chem.* 2013, 24, 1650, incorporated by reference herein) describes the metabolic incorporation of 6-thiofucose into the glycan of a monoclonal antibody, followed by reduction-oxidation-maleimide conjugation. Interestingly, it was found that the 6-thiofucose maleimide conjugate described above was found to display enhanced stability with respect to cysteine maleimide conjugates. However, efficiency of incorporation of 6-thiofucose was found to be only 70%.

One alternative variant of maleimide conjugation, which was applied for the generation of an antibody-drug conjugate, involves a strategy where not the nucleophilic thiol is introduced in the monoclonal antibody, but rather the maleimide. For example, T-DM1 is prepared by first (random) conjugation of lysines with succinimidyl 4-(N-maleimidomethyl)cyclohexane-1-carboxylate (SMCC), thereby effectively charging the antibody with maleimides. In the next stage of the process, the maleimide-functionalized antibody is treated with thiol-functionalized maytansinoid, leading to the conjugate. Hence, this is a unique example where the antibody is effectively converted into an electrophilic reaction partner (instead of the common use of nucleophilic amino acid side chains for conjugation), upon treatment with SMCC. However, also in this case, by nature of the approach, only random conjugation of antibody is achieved.

Notwithstanding the versatility of the above technologies, a general disadvantage of protein conjugates obtained via alkylation with maleimides is that in general the resulting conjugates can be potentially unstable due to the reverse of alkylation, i.e. a retro-Michael reaction.

An alternative strategy to prepare conjugates of a glycoprotein, a subclass of all proteins, involves the generation of one or more aldehyde functions on the protein's glycan structure, either by chemical means (sodium periodate) or by enzymatic means (galactose oxidase). The latter aldehyde function can subsequently be employed for a selective conjugation process, for example by condensation with a functionalized hydroxylamine or hydrazine molecule, thereby generating an oxime-linked or hydrazone-linked protein conjugate, respectively. However, it is known that oximes and hydrazones, in particular derived from aliphatic aldehydes, also show limited stability over time in water or at lower pH. For example, gemtuzumab ozogamicin is an oxime-linked antibody-drug conjugate and is known to suffer from premature deconjugation in vivo.

Qasba et al. disclose in *J. Biol. Chem.* 2002, 277, 20833, incorporated by reference herein, that mutant galactosyltransferases GalT(Y289L), GalT(Y289I) and GalT(Y289N) can enzymatically attach GalNAc to a non-reducing GlcNAc sugar (β-benzyl-GlcNAc).

WO 2007/095506 and WO 2008/029281 (Invitrogen Corporation), incorporated by reference herein, disclose that the combination of GalT(Y289L) mutant with the C2-substituted azidoacetamido moiety 2-GalNAz-UDP leads to the incorporation of GalNAz at a terminal non-reducing Glc- NAc of a glycan. Subsequent conjugation by Staudinger ligation or with copper-catalyzed click chemistry then provides the respective antibody conjugates wherein a fluorescent alkyne probe is conjugated to an antibody. WO 2007/095506 and WO 2008/029281 further disclose that trimming of the glycan can take place with endo H, thereby hydrolyzing a GlcNAc-GlcNAc glycosidic bond and liberating a GlcNAc for enzymatic introduction of GalNAz.

Qasba et al. disclose in *Bioconjugate Chem.* 2009, 20, 1228, incorporated by reference herein, that β-galactosidase-treated monoclonal antibodies (e.g. Rituxan, Remicade, Herceptin) having a G0 glycoform (obtained by treatment of the crude mAbs with galactosidase) are fully regalactosylated to the G2 glycoform after transfer of a galactose moiety comprising a (GalNAz) to the terminal GlcNAc residues of the glycan, leading to tetraazido-substituted antibodies, i.e. two GalNAz moieties per heavy chain. The conjugation of said tetraazido-substituted antibodies to a molecule of interest, for example by Staudinger ligation or cycloaddition with an alkyne, is not disclosed. The transfer of a galactose moiety comprising a C2-substituted keto group (C2-keto-Gal) to the terminal GlcNAc residues of a G0 glycoform glycan, as well as the linking of C2-keto-Gal to aminooxy biotin, is also disclosed. However, as mentioned above, the resulting oxime conjugates may display limited stability due to aqueous hydrolysis.

A disadvantage of the methods disclosed in WO 2007/095506, WO 2004/063344 and *Bioconjugate Chem.* 2009, 20, 1228 is that the conjugates obtained by azide-alkyne click chemistry in all cases feature a triazole linkage, which may be disadvantageous with respect to immunogenicity of the ADC. Moreover, in case copper-catalyzed click chemistry is employed, protein damage resulting from undesired oxidative processes may occur, as is disclosed in e.g. Hong et al., *Angew. Chem. Int. Ed. Engl.* 2009, 48, 9879 (incorporated by reference).

Based on the above, it is clear that galactose can be introduced to proteins featuring a terminal GlcNAc-moiety upon treatment with wild type Gal-T1/UDP-Gal (leading to Gal-GlcNAc-protein), while N-acetylgalactosamine can be introduced upon treatment with GalT1 mutant Y289L (affording GalNAc-GlcNAc-protein). It has also been shown by Elling et al. (*ChemBioChem* 2001, 2, 884, incorporated by reference herein) that a variety of human galactosyltransferases (β4-Gal-T1, β4-Gal-T4 and β3-Gal-T5), but not bovine 134-Gal-T1, can accommodate a 6-biotinylated modification of galactose in UDP-Gal, in the absence of $Mn^{2+}$, leading to effective transfer to model proteins BSA-$(GlcNAc)_{17}$ and ovalbumin. Similarly, Pannecoucke et al. (*Tetrahedron Lett.* 2008, 49, 2294, incorporated by reference herein) demonstrated that commercially available bovine β4-Gal-T1 under standard conditions is also able to transfer UDP-6-azidogalactose to a model GlcNAc-substrate, but the transfer to a GlcNAc-protein was not demonstrated.

Based on the above, it may be concluded that a strategy involving chemoselective or enzymatic modification of glycans on glycoproteins is a versatile strategy for the site-specific preparation of protein conjugates. However, the current technologies generate linkages of unpredictable stability (maleimides, oximes, hydrazones) or unnatural constitution (triazoles). Moreover, the mode of preparation may be slow and require large excesses of reagent (oxime or hydrazone ligation) or may lead to protein damage (copper-catalyzed click chemistry). Finally, the recently disclosed strategy for metabolic thiofucose incorporation has promise, but efficiency of thiofucose incorporation is low (±70%) due to competition with natural fucose.

Conjugations of biomolecules based on thiols are well-known in the art. In particular, reaction of thiols with maleimide is a fast and selective process, which typically rapidly leads to the desired conjugate. Less popular but also regularly applied are halogenated acetamides that may also react with high selectivity with free thiols although chemoselectivity is compromised with respect to maleimide conjugation. A particular advantage of conjugation with halogenated acetamides is the irreversible formation of a thioether, which compares favorably to maleimide conjugates with respect to stability. The latter stability also applied to conjugates formed by reaction of thiols with allenamide, as most recently reported by Abbas et al., *Angew. Chem. Int. Ed.* 2014, 53, 7491-7494, incorporated by reference. Other alternatives for conjugation to thiols are also known, for example vinylsulfone conjugation, but less frequently applied. Finally, light-induced thiol-ene reaction has also been shown to be suitable for protein conjugation, see for example Kunz et al. *Angew. Chem. Int. Ed.* 2007, 46, 5226-5230), also in this case leading to highly stable thioethers.

SUMMARY OF THE INVENTION

The invention relates to a process for the preparation of a modified glycoprotein, the process comprising contacting a glycoprotein comprising a glycan comprising a terminal GlcNAc-moiety with $Su(A)_x$-P in the presence of a catalyst selected from the group consisting of β(1,4)-galactosyltransferases, β(1,3)-N-galactosyltransferases, β(1,4)-galactosyltransferases comprising a mutant catalytic domain and β(1,3)-N-galactosyltransferases comprising a mutant catalytic domain; wherein $Su(A)_x$ is a sugar derivative Su comprising x functional groups A wherein x is 1, 2, 3 or 4 and wherein A is independently selected from the group consisting of a thiol group or a precursor thereof, a halogen, a sulfonyloxy group, a halogenated acetamido group, a mercaptoacetamido group and a sulfonated hydroxyacetamido group; wherein P is a nucleotide; and wherein a glycan comprising a terminal GlcNAc-moiety is a glycan according to formula (101) or (102):

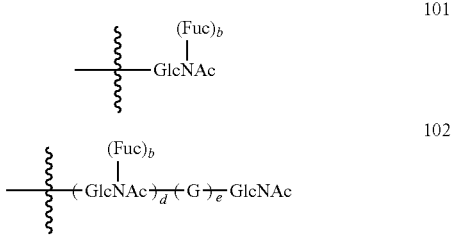

wherein:
b is 0 or 1;
d is 0 or 1;
e is 0 or 1; and
G is a monosaccharide, or a linear or branched oligosaccharide comprising 2 to 20 sugar moieties.

The invention also relates to a glycoprotein comprising a glycan according to formula (105) or (106):

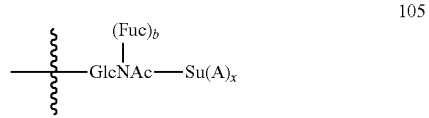

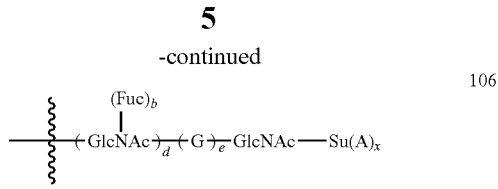

wherein:
b is 0 or 1;
d is 0 or 1;
e is 0 or 1;
G is a monosaccharide, or a linear or branched oligosaccharide comprising 2-20 saccharide moieties; and
$Su(A)_x$ is a sugar derivative Su comprising x functional groups A, wherein x is 1, 2, 3 or 4 and wherein A is independently selected from the group consisting a thiol group, a halogen, a sulfonyloxy group, a halogenated acetamido group, a mercaptoacetamido group and a sulfonated hydroxyacetamido group.

The invention also relates to the use of a glycoprotein according to the invention in the preparation of a glycoprotein-conjugate, wherein a glycoprotein-conjugate is defined as a glycoprotein that is conjugated to a molecule of interest D via a linker L; and to a process for the preparation of a glycoprotein-conjugate, said process comprising reacting a modified glycoprotein according to the invention with a linker-conjugate, wherein said linker-conjugate comprises a functional group B and one or more molecules of interest, wherein said functional group B is a functional group that is capable of reacting with a functional group A on a glycan of the modified glycoprotein, and wherein functional group A is as defined above.

In particular, the invention relates to modified antibodies, antibody-conjugates and antibody-drug conjugates.

DETAILED DESCRIPTION OF THE INVENTION

Definitions

Figure 1:
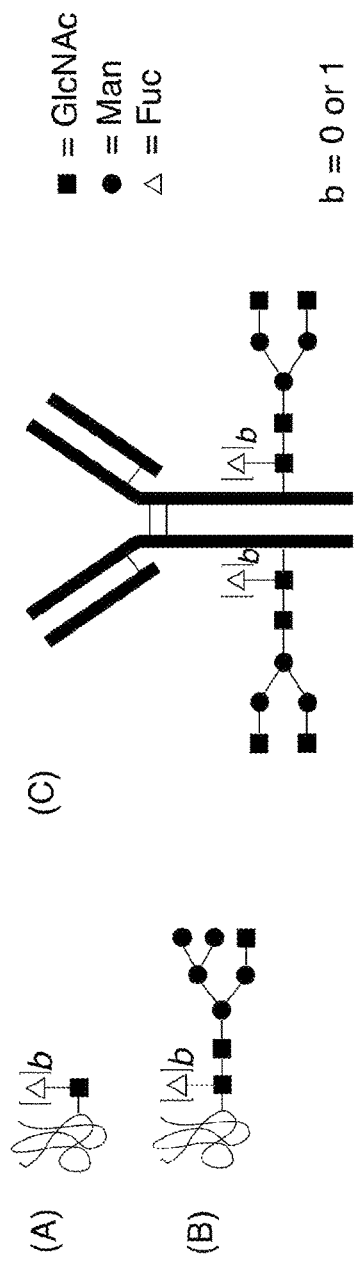
FIG. 1 shows examples of the different glycoforms of a protein that (A) can be obtained by regular expression followed by trimming with endo-glycosidase, or (B) by expression of a mAb in a mammalian system in the presence of swainsonine or by expression in an engineered host organism, e.g. Lec1 CHO or *Pichia*, or (C) by trimming of the regular mixture of glycoforms (G0, G1, G2, G0F, G1F and G2F) upon combined action of sialidase and galactosidase.

The verb "to comprise" as is used in this description and in the claims and its conjugations is used in its non-limiting sense to mean that items following the word are included, but items not specifically mentioned are not excluded.

In addition, reference to an element by the indefinite article "a" or "an" does not exclude the possibility that more than one of the elements is present, unless the context clearly requires that there is one and only one of the elements. The indefinite article "a" or "an" thus usually means "at least one".

The compounds disclosed in this description and in the claims may comprise one or more asymmetric centres, and different diastereomers and/or enantiomers may exist of the compounds. The description of any compound in this description and in the claims is meant to include all diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer.

The compounds may occur in different tautomeric forms. The compounds according to the invention are meant to include all tautomeric forms, unless stated otherwise. When the structure of a compound is depicted as a specific tautomer, it is to be understood that the invention of the present application is not limited to that specific tautomer.

Unsubstituted alkyl groups have the general formula $C_nH_{2n+1}$ and may be linear or branched. Unsubstituted alkyl groups may also contain a cyclic moiety, and thus have the concomitant general formula $C_nH_{2n-1}$. Optionally, the alkyl groups are substituted by one or more substituents further specified in this document. Examples of alkyl groups include methyl, ethyl, propyl, 2-propyl, t-butyl, 1-hexyl, 1-dodecyl, etc.

An aryl group comprises six to twelve carbon atoms and may include monocyclic and bicyclic structures. Optionally, the aryl group may be substituted by one or more substituents further specified in this document. Examples of aryl groups are phenyl and naphthyl.

Arylalkyl groups and alkylaryl groups comprise at least seven carbon atoms and may include monocyclic and bicyclic structures. Optionally, the arylalkyl groups and alkylaryl may be substituted by one or more substituents further specified in this document. An arylalkyl group is for example benzyl. An alkylaryl group is for example 4-t-butylphenyl.

Heteroaryl groups comprise at least two carbon atoms (i.e. at least $C_2$) and one or more heteroatoms N, O, P or S. A heteroaryl group may have a monocyclic or a bicyclic structure. Optionally, the heteroaryl group may be substituted by one or more substituents further specified in this document. Examples of suitable heteroaryl groups include pyridinyl, quinolinyl, pyrimidinyl, pyrazinyl, pyrazolyl, imidazolyl, thiazolyl, pyrrolyl, furanyl, triazolyl, benzofuranyl, indolyl, purinyl, benzoxazolyl, thienyl, phospholyl and oxazolyl.

Heteroarylalkyl groups and alkylheteroaryl groups comprise at least three carbon atoms (i.e. at least $C_3$) and may include monocyclic and bicyclic structures. Optionally, the heteroaryl groups may be substituted by one or more substituents further specified in this document.

Where an aryl group is denoted as a (hetero)aryl group, the notation is meant to include an aryl group and a heteroaryl group. Similarly, an alkyl(hetero)aryl group is meant to include an alkylaryl group and a alkylheteroaryl group, and (hetero)arylalkyl is meant to include an arylalkyl group and a heteroarylalkyl group. A $C_2$-$C_{24}$ (hetero)aryl group is thus to be interpreted as including a $C_2$-$C_{24}$ heteroaryl group and a $C_6$-$C_{24}$ aryl group. Similarly, a $C_3$-$C_{24}$ alkyl(hetero)aryl group is meant to include a $C_7$-$C_{24}$ alkylaryl group and a $C_3$-$C_{24}$ alkylheteroaryl group, and a $C_3$-$C_{24}$ (hetero)arylalkyl is meant to include a $C_7$-$C_{24}$ arylalkyl group and a $C_3$-$C_{24}$ heteroarylalkyl group.

Unless stated otherwise, alkyl groups, alkenyl groups, alkenes, alkynes, (hetero)aryl groups, (hetero)arylalkyl groups and alkyl(hetero)aryl groups may be substituted with one or more substituents selected from the group consisting of C1-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo and silyl groups, wherein the silyl groups can be represented by the formula $(R^{10})_3Si-$, wherein $R^{10}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one or more heteroatoms selected from the group consisting of O, N and S.

An alkynyl group comprises a carbon-carbon triple bond. An unsubstituted alkynyl group comprising one triple bond has the general formula $C_nH_{2n-3}$. A terminal alkynyl is an alkynyl group wherein the triple bond is located at a terminal position of a carbon chain. Optionally, the alkynyl group is substituted by one or more substituents further specified in this document, and/or interrupted by heteroatoms selected from the group of oxygen, nitrogen and sulphur. Examples of alkynyl groups include ethynyl, propynyl, butynyl, octynyl, etc.

A cycloalkynyl group is a cyclic alkynyl group. An unsubstituted cycloalkynyl group comprising one triple bond has the general formula $C_nH_{2n-5}$. Optionally, a cycloalkynyl group is substituted by one or more substituents further specified in this document. An example of a cycloalkynyl group is cyclooctynyl.

A heterocycloalkynyl group is a cycloalkynyl group interrupted by heteroatoms selected from the group of oxygen, nitrogen and sulphur. Optionally, a heterocycloalkynyl group is substituted by one or more substituents further specified in this document. An example of a heterocycloalkynyl group is azacyclooctynyl.

A (hetero)aryl group comprises an aryl group and a heteroaryl group. An alkyl(hetero)aryl group comprises an alkylaryl group and an alkylheteroaryl group. A (hetero)arylalkyl group comprises a arylalkyl group and a heteroarylalkyl groups. A (hetero)alkynyl group comprises an alkynyl group and a heteroalkynyl group. A (hetero)cycloalkynyl group comprises an cycloalkynyl group and a heterocycloalkynyl group.

A (hetero)cycloalkyne compound is herein defined as a compound comprising a (hetero)cycloalkynyl group.

Several of the compounds disclosed in this description and in the claims may be described as fused (hetero)cycloalkyne compounds, i.e. (hetero)cycloalkyne compounds wherein a second ring structure is fused, i.e. annelated, to the (hetero)cycloalkynyl group. For example in a fused (hetero)cyclooctyne compound, a cycloalkyl (e.g. a cyclopropyl) or an arene (e.g. benzene) may be annelated to the (hetero)cyclooctynyl group. The triple bond of the (hetero)cyclooctynyl group in a fused (hetero)cyclooctyne compound may be located on either one of the three possible locations, i.e. on the 2, 3 or 4 position of the cyclooctyne moiety (numbering according to "IUPAC Nomenclature of Organic Chemistry", Rule A31.2). The description of any fused (hetero)cyclooctyne compound in this description and in the claims is meant to include all three individual regioisomers of the cyclooctyne moiety.

When an alkyl group, a (hetero)aryl group, alkyl(hetero) aryl group, a (hetero)arylalkyl group, a (hetero)cycloalkynyl group is optionally substituted, said groups are independently optionally substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S, wherein the silyl groups are represented by the formula $(R^6)_3Si-$, wherein $R^6$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S.

The general term "sugar" is herein used to indicate a monosaccharide, for example glucose (Glc), galactose (Gal), mannose (Man) and fucose (Fuc). The term "sugar derivative" is herein used to indicate a derivative of a monosaccharide sugar, i.e. a monosaccharide sugar comprising substituents and/or functional groups. Examples of a sugar derivative include amino sugars and sugar acids, e.g. glucosamine ($GlcNH_2$), galactosamine ($GalNH_2$)N-acetylglucosamine (GlcNAc), N-acetylgalactosamine (GalNAc), sialic acid (Sia) which is also referred to as N-acetylneuraminic acid (NeuNAc), and N-acetylmuramic acid (MurNAc), glucuronic acid (GlcA) and iduronic acid (IdoA). Examples of a sugar derivative also include compounds herein denoted $Su(A)_x$, wherein Su is a sugar or a sugar derivative, and wherein Su comprises x functional groups A.

The term "nucleotide" is herein used in its normal scientific meaning. The term "nucleotide" refers to a molecule that is composed of a nucleobase, a five-carbon sugar (either ribose or 2-deoxyribose), and one, two or three phosphate groups. Without the phosphate group, the nucleobase and sugar compose a nucleoside. A nucleotide can thus also be called a nucleoside monophosphate, a nucleoside diphosphate or a nucleoside triphosphate. The nucleobase may be adenine, guanine, cytosine, uracil or thymine. Examples of a nucleotide include uridine diphosphate (UDP), guanosine diphosphate (GDP), thymidine diphosphate (TDP), cytidine diphosphate (CDP) and cytidine monophosphate (CMP).

The term "protein" is herein used in its normal scientific meaning. Herein, polypeptides comprising about 10 or more amino acids are considered proteins. A protein may comprise natural, but also unnatural amino acids.

The term "glycoprotein" is herein used in its normal scientific meaning and refers to a protein comprising one or more monosaccharide or oligosaccharide chains ("glycans") covalently bonded to the protein. A glycan may be attached to a hydroxyl group on the protein (O-linked-glycan), e.g. to the hydroxyl group of serine, threonine, tyrosine, hydroxylysine or hydroxyproline, or to an amide function on the protein (N-glycoprotein), e.g. asparagine or arginine, or to a carbon on the protein (C-glycoprotein), e.g. tryptophan. A glycoprotein may comprise more than one glycan, may comprise a combination of one or more monosaccharide and one or more oligosaccharide glycans, and may comprise a combination of N-linked, O-linked and C-linked glycans. It is estimated that more than 50% of all proteins have some form of glycosylation and therefore qualify as glycoprotein. Examples of glycoproteins include PSMA (prostate-specific membrane antigen), CAL (*candida antartica* lipase), gp41, gp120, EPO (erythropoietin), antifreeze protein and antibodies.

The term "glycan" is herein used in its normal scientific meaning and refers to a monosaccharide or oligosaccharide chain that is linked to a protein. The term glycan thus refers to the carbohydrate-part of a glycoprotein. The glycan is attached to a protein via the C-1 carbon of one sugar, which may be without further substitution (monosaccharide) or may be further substituted at one or more of its hydroxyl groups (oligosaccharide). A naturally occurring glycan typically comprises 1 to about 10 saccharide moieties. However, when a longer saccharide chain is linked to a protein, said saccharide chain is herein also considered a glycan.

A glycan of a glycoprotein may be a monosaccharide. Typically, a monosaccharide glycan of a glycoprotein consists of a single N-acetylglucosamine (GlcNAc), glucose (Glc), mannose (Man) or fucose (Fuc) covalently attached to the protein.

A glycan may also be an oligosaccharide. An oligosaccharide chain of a glycoprotein may be linear or branched. In an oligosaccharide, the sugar that is directly attached to the protein is called the core sugar. In an oligosaccharide, a sugar that is not directly attached to the protein and is attached to at least two other sugars is called an internal sugar. In an oligosaccharide, a sugar that is not directly attached to the protein but to a single other sugar, i.e. carrying no further sugar substituents at one or more of its other hydroxyl groups, is called the terminal sugar. For the avoidance of doubt, there may exist multiple terminal sugars in an oligosaccharide of a glycoprotein, but only one core sugar.

A glycan may be an O-linked glycan, an N-linked glycan or a C-linked glycan. In an O-linked glycan a monosaccharide or oligosaccharide glycan is bonded to an O-atom in an amino acid of the protein, typically via a hydroxyl group of serine (Ser) or threonine (Thr). In an N-linked glycan a monosaccharide or oligosaccharide glycan is bonded to the protein via an N-atom in an amino acid of the protein, typically via an amide nitrogen in the side chain of asparagine (Asn) or arginine (Arg). In a C-linked glycan, a monosaccharide or oligosaccharide glycan is bonded to a C-atom in an amino acid of the protein, typically to a C-atom of tryptophan (Trp).

The end of an oligosaccharide that is directly attached to the protein is called the reducing end of a glycan. The other end of the oligosaccharide is called the non-reducing end of a glycan.

For O-linked glycans, a wide diversity of chains exists. Naturally occurring O-linked glycans typically feature a serine or threonine-linked α-O-GalNAc moiety, further substituted with galactose, sialic acid and/or fucose. The hydroxylated amino acid that carries the glycan substitution may be part of any amino acid sequence in the protein.

For N-linked glycans, a wide diversity of chains exists. Naturally occurring N-linked glycans typically feature an asparagine-linked β-N-GlcNAc moiety, in turn further substituted at its 4-OH with β-GlcNAc, in turn further substituted at its 4-OH with β-Man, in turn further substituted at its 3-OH and 6-OH with α-Man, leading to the glycan pentasaccharide $Man_3GlcNAc_2$. The core GlcNAc moiety may be further substituted at its 6-OH by α-Fuc. The pentasaccharide $Man_3GlcNAc_2$ is the common oligosaccharide scaffold of nearly all N-linked glycoproteins and may carry a wide variety of other substituents, including but not limited to Man, GlcNAc, Gal and sialic acid. The asparagine that is substituted with the glycan on its side-chain is typically part of the sequence Asn-X-Ser/Thr, with X being any amino acid but proline and Ser/Thr being either serine or threonine.

The term "antibody" is herein used in its normal scientific meaning. An antibody is a protein generated by the immune system that is capable of recognizing and binding to a specific antigen. An antibody is an example of a glycoprotein. The term antibody herein is used in its broadest sense and specifically includes monoclonal antibodies, polyclonal antibodies, dimers, multimers, multispecific antibodies (e.g. bispecific antibodies), antibody fragments, and double and single chain antibodies. The term "antibody" is herein also meant to include human antibodies, humanized antibodies, chimeric antibodies and antibodies specifically binding cancer antigen. The term "antibody" is meant to include whole antibodies, but also fragments of an antibody, for example an antibody Fab fragment, (Fab')₂, Fv fragment or Fc fragment from a cleaved antibody, a scFv-Fc fragment, a minibody, a diabody or a scFv. Furthermore, the term includes genetically engineered antibodies and derivatives of an antibody. Antibodies, fragments of antibodies and genetically engineered antibodies may be obtained by methods that are known in the art. Suitable marketed antibodies include, amongst others, abciximab, rituximab, basiliximab, palivizumab, infliximab, trastuzumab, alemtuzumab, adalimumab, tositumomab-I131, cetuximab, ibrituximab tiuxetan, omalizumab, bevacizumab, natalizumab, ranibizumab, panitumumab, eculizumab, certolizumab pegol, golimumab, canakinumab, catumaxomab, ustekinumab, tocilizumab, ofatumumab, denosumab, belimumab, ipilimumab and brentuximab.

The terms "treatment," "treating," and the like refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes preventing the disease from occurring in a subject which may be predisposed to the disease but has not yet been diagnosed as having it; inhibiting the disease, i.e., arresting its development; relieving the disease, i.e., causing regression of the disease.

Process for the Preparation of a Modified Glycoprotein

The present invention relates to a process for the preparation of a modified glycoprotein, the process comprising contacting a glycoprotein comprising a glycan comprising a terminal GlcNAc-moiety with $Su(A)_x$-P in the presence of a suitable catalyst; wherein $Su(A)_x$ is a sugar derivative Su comprising x functional groups A wherein x is 1, 2, 3 or 4 and wherein A is independently selected from the group consisting of a thiol group or a precursor thereof, a halogen, a sulfonyloxy group, a halogenated acetamido group, a mercaptoacetamido group and a sulfonated hydroxyacetamido group; wherein P is a nucleotide; wherein a suitable catalyst is defined as a galactosyltransferase or a galactosyltransferase comprising a mutant catalytic domain, wherefore $Su(A)_x$-P is a substrate; and wherein a glycan comprising a terminal GlcNAc-moiety is a glycan according to formula (101) or (102):

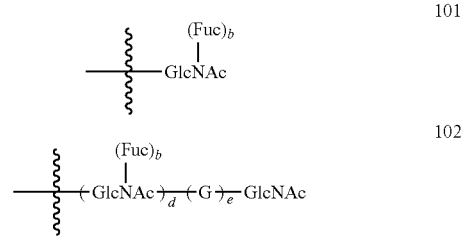

wherein:
b is 0 or 1;
d is 0 or 1;
e is 0 or 1; and
G is a monosaccharide, or a linear or branched oligosaccharide comprising 2 to 20 sugar moieties.

Preferably, the catalyst is selected from the group consisting of β(1,4)-galactosyltransferases, β(1,3)-N-galactosyltransferases, β(1,4)-galactosyltransferases comprising a mutant catalytic domain and β(1,3)-N-galactosyltransferases comprising a mutant catalytic domain. The catalyst is described in more detail below.

The glycoprotein that is to be modified in the process according to the invention comprises a glycan, said glycan comprising a terminal GlcNAc-moiety, i.e. a Glc-NAc moiety that is present at the non-reducing end of the glycan. Said glycan comprises one or more saccharide moieties, and may be linear or branched. Herein, the GlcNAc-moiety of a glycan according to formula (101) wherein b is 1 (i.e. a glycan consisting of a fucosylated GlcNAc), is also considered a terminal GlcNAc-moiety.

In glycan (102) it is preferred that when d is 0 then e is 1, and when e is 0 then d is 1.

G represents a monosaccharide, or a linear or branched oligosaccharide comprising 2 to 20, preferably 2 to 12, more preferably 2 to 10, even more preferably 2 to 8 and most preferably 2 to 6 sugar moieties. Sugar moieties that may be present in a glycan are known to a person skilled in the art, and include e.g. glucose (Glc), galactose (Gal), mannose (Man), fucose (Fuc), N-acetylglucosamine (GlcNAc), N-acetylgalactosamine (GalNAc), N-acetylneuraminic acid (NeuNAc) or sialic acid, xylose (Xyl).

In one embodiment, the glycan comprising a terminal GlcNAc-moiety consists of one GlcNAc-moiety, and the glycan is a glycan according to formula (101), wherein b is 0. In another embodiment, said glycan consists of a fucosylated GlcNAc-moiety, and the glycan is a glycan according to formula (101), wherein b is 1. In yet another embodiment, said glycan is a glycan according to formula (102), wherein the core-GlcNAc, if present, is optionally fucosylated (b is 0 or 1).

When a core-GlcNAc-moiety is fucosylated, fucose is most commonly linked α-1,6 to C6 of the core-GlcNAc substituent. As described above, the GlcNAc-moiety of a glycan according to formula (101) wherein b is 1, is herein also considered a terminal GlcNAc-moiety.

As described above, a preferred glycan comprising a terminal GlcNAc-moiety is a glycan according to formula (101) or (102). In a further preferred embodiment the glycoprotein that is to be modified in the process according to the invention is a glycoprotein according to formula (103) or (104):

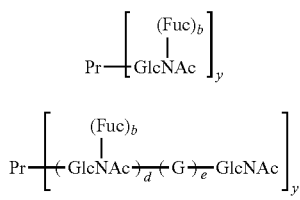

103

$$\text{Pr}\left[\begin{array}{c}(\text{Fuc})_b \\ | \\ \text{GlcNAc}\end{array}\right]_y$$

104

$$\text{Pr}\left[\begin{array}{c}(\text{Fuc})_b \\ | \\ (\text{GlcNAc})_d\text{-}(\text{G})_e\text{-}\text{GlcNAc}\end{array}\right]_y$$

wherein:
Pr represents a protein;
y is 1 to 20; and
b, d, e and G are as defined above.

Preferably, when d is 0 then e is 1, and when e is 0 then d is 1. When G is a linear or branched oligosaccharide, it is preferred that G comprises 2 to 12, more preferably 2 to 10, even more preferably 2 to 8 and most preferably 2 to 6 sugar moieties. In another preferred embodiment, y is 1 to 12, more preferably y is 1, 2, 3, 4, 5, 6, 7 or 8, and even more preferably y is 1, 2, 3 or 4. Most preferably y is 1 or 2. In yet another preferred embodiment, y is 2, 4, 6 or 8, preferably 2 or 4, most preferably 2. This embodiment is particularly preferred when the glycoprotein to be modified is an antibody, i.e. when Pr is Ab.

In the process according to the invention, when the glycoprotein that is to be modified is a glycoprotein according to formula (103) or (104), a glycoprotein mixture may be used as the starting glycoprotein, said mixture comprising glycoproteins comprising one or more fucosylated (b is 1) glycans (101) and/or (102) and/or one or more non-fucosylated (b is 0) glycans (101) and/or (101).

A glycoprotein comprising a glycan comprising a terminal GlcNAc-moiety is herein also referred to as a "terminal non-reducing GlcNAc-protein", and a glycan comprising a terminal GlcNAc-moiety is herein also referred to as a "terminal non-reducing GlcNAc-glycan". It should be noted that the term "terminal non-reducing GlcNAc-protein" includes a protein of formula (103) wherein b is 1, and that the term "terminal non-reducing GlcNAc-glycan" includes a glycan of formula (101) wherein b is 1.

The terminal non-reducing GlcNAc-protein may comprise a linear or a branched terminal non-reducing GlcNAc-glycan. Said glycan is bonded via C1 of the core-sugar-moiety to the protein, and said core-sugar-moiety preferably is a core-GlcNAc-moiety. Consequently, when the terminal non-reducing GlcNAc-glycan bonded to the protein is a glycan according to formula (102), it is preferred that d is 1.

In a preferred embodiment, C1 of the core-sugar moiety of the terminal non-reducing GlcNAc-glycan is bonded to the protein via an N-glycosidic bond to a nitrogen atom in an amino acid residue in said protein, more preferably to an amide nitrogen atom in the side chain of an asparagine (Asn) or an arginine (Arg) amino acid. However, C1 of the core-sugar-moiety of the non-reducing GlcNAc-glycan may also be bonded to the protein via an O-glycosidic bond to an oxygen atom in an amino acid residue in said protein, more preferably to an oxygen atom in the side chain of a serine (Ser) or threonine (Thr) amino acid. In this embodiment, it is preferred that the core-sugar-moiety of said glycan is an O-GlcNAc-moiety or an O-GalNAc moiety, preferably an O-GlcNAc moiety. C1 of the core-sugar-moiety of the non-reducing GlcNAc-glycan may also be bonded to the protein via a C-glycosidic bond to a carbon atom on the protein, e.g. to tryptophan (Trp). As described above, a glycoprotein may comprise more than one glycan, and may comprise a combination of N-linked, O-linked and C-linked glycoproteins.

The terminal non-reducing GlcNAc-glycan may be present at a native glycosylation site of a protein, but may also be introduced on a different site on a protein.

In a preferred embodiment the terminal non-reducing GlcNAc-protein is an antibody (Ab), the antibody comprising a glycan comprising a terminal GlcNAc-moiety. Such an antibody is herein also referred to as a "terminal non-reducing GlcNAc-antibody". A preferred terminal non-reducing GlcNAc-antibody is an antibody according to formula (103) or (104) as defined above, wherein Pr is Ab. In this embodiment, it is further preferred that y is 1, 2, 3, 4, 5, 6, 7 or 8, and even more preferred that y is 2, 4, 6 or 8.

As was defined above, said antibody may be a whole antibody, but also an antibody fragment. When the antibody is a whole antibody, said antibody preferably comprises one or more, more preferably one, terminal non-reducing GlcNAc-glycan on each heavy chain. Said whole antibody thus preferably comprises two or more, preferably two, four, six or eight of said glycans, more preferably two or four, and most preferably two glycans. In other words, when said antibody is a whole antibody, y is preferably 2, 4, 6 or 8, more preferably y is 2 or 4, and most preferably y is 2. When the antibody is an antibody fragment, it is preferred that y is 1, 2, 3 or 4, and more preferably y is 1 or 2.

In a particular preferred embodiment, when said glycoprotein is an antibody, y is 1, 2 or 4.

In a preferred embodiment, said antibody is a monoclonal antibody (mAb). Preferably, said antibody is selected from the group consisting of IgA, IgD, IgE, IgG and IgM antibodies. More preferably, said antibody is an IgG antibody, and most preferably said antibody is an IgG1 antibody.

Figure 13:
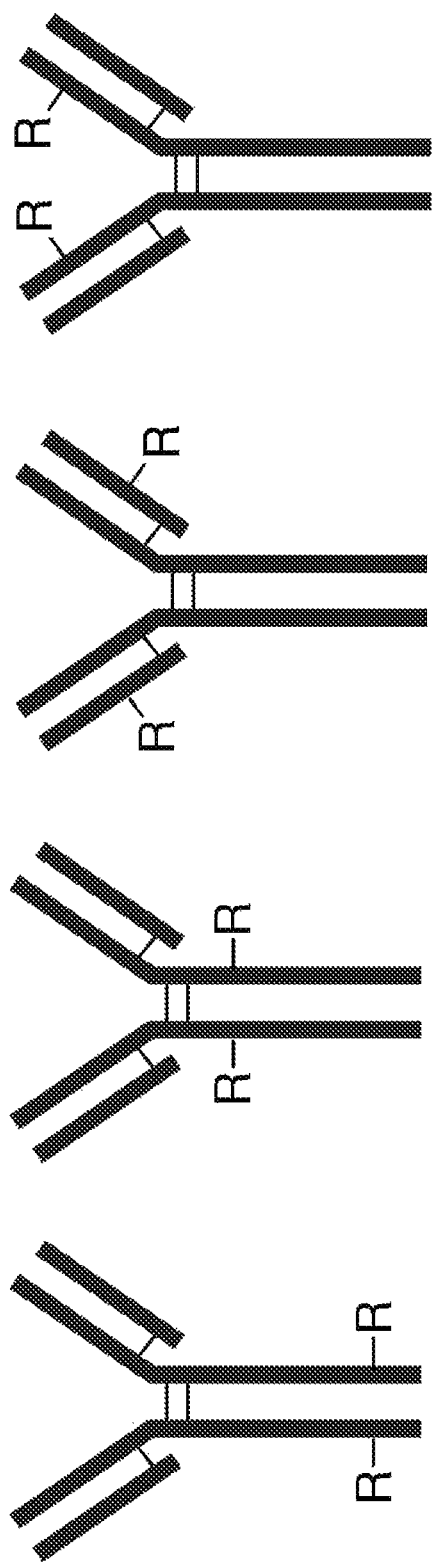
FIG. 13 shows different glycoforms of a monoclonal antibody, e.g. IgG, which can be obtained by removing the native glycosylation site of a mAb and engineering a glycosylation site (based on sequence N—X—S/T, with X is any amino acid except proline) at another position.

In a preferred embodiment, the glycoprotein in an antibody is attached to the conserved N-glycosylation site in the Fc-fragment at asparagine in the region 290-305, typically N297. In another preferred embodiment, the glycoprotein in an antibody is attached to a non-native glycosylation site in the antibody. It is further preferred that said non-native glycosylation site is a non-native N-glycosylation site. A non-native glycosylation site may be introduced into the antibody via glycoengineering techniques. Several examples of the position of a glycosylation site in an antibody are shown in FIG. 13.

Several examples of a terminal non-reducing GlcNAc-protein that may be modified in the process according to the invention are shown in FIG. 1. FIG. 1 (a) shows a glycoprotein comprising a single, optionally fucosylated, GlcNAc-moiety; this GlcNAc-glycan may for example be linked to the protein via an N-glycosidic or an O-glycosidic bond. FIG. 1(b) shows a glycoprotein comprising a branched octasaccharide glycan wherein one of the branches comprises a terminal GlcNAc-moiety (this glycan is also referred to as GnM$_5$) The core-GlcNAc may optionally be fucosylated. FIG. 1(c) shows an antibody comprising a branched heptasaccharide glycan, wherein the core-GlcNAc moiety is optionally fucosylated and wherein all branches comprise a terminal GlcNAc-moiety.

Figure 2:
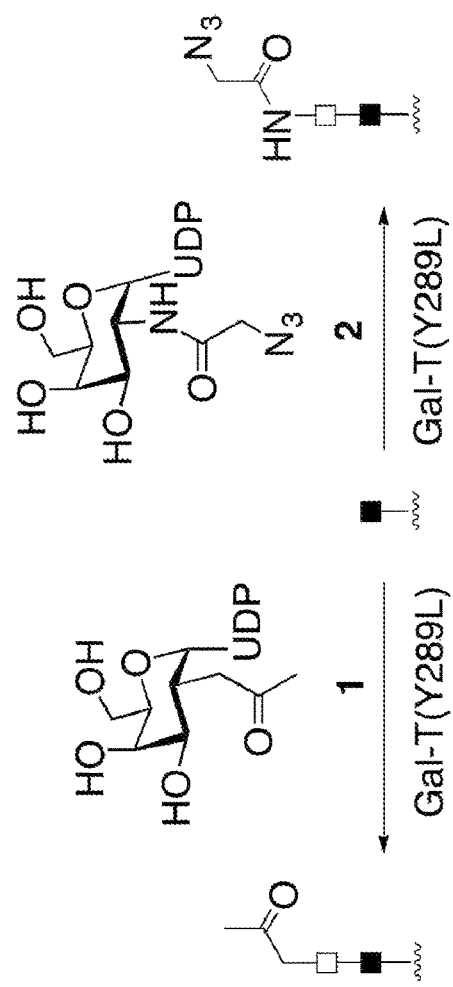
FIG. 2 shows a schematic representation of the enzymatic conversion of a GlcNAc-terminated protein with unnatural UDP-galactose derivative 1 (2-ketogalactose) or 2 (GalNAz), upon the action of galactosyl transferase mutant β(1,4)-Gal-T1(Y298L).

A process for the attachment of an unnatural galactose derivative to a terminal non-reducing GlcNAc-protein under the action of galactosyltransferase mutant Y289L is shown in FIG. 2.

A modified glycoprotein obtainable by the process for the modification of a glycoprotein according to the invention is defined as a glycoprotein comprising a modified glycan, said glycan comprising a GlcNAc-Su(A)$_x$ disaccharide-moiety at the non-reducing end, wherein Su(A)$_x$ is as defined above.

Preferably, the modified glycan is according to the formula (105) or (106), wherein b, d and e, as well as their preferred embodiments, are as defined above, and wherein Su(A)$_x$ is a sugar derivative Su comprising x functional groups A, wherein x is 1, 2, 3 or 4 and wherein A is independently selected from the group consisting of a thiol group or a precursor thereof, a halogen, a sulfonyloxy group, a halogenated acetamido group, a mercaptoacetamido group and a sulfonated hydroxyacetamido group.

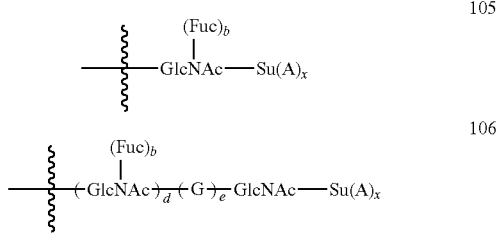

The present invention thus also relates to a process for the preparation of a modified glycoprotein, the process comprising contacting a glycoprotein comprising a glycan comprising a terminal GlcNAc-moiety with Su(A)$_x$-P in the presence of a suitable catalyst; wherein Su(A)$_x$ is a sugar derivative Su comprising x functional groups A wherein x is 1, 2, 3 or 4 and wherein A is independently selected from the group consisting of a thiol group or a precursor thereof, a halogen, a sulfonyloxy group, a halogenated acetamido group, a mercaptoacetamido group and a sulfonated hydroxyacetamido group; wherein P is a nucleotide; wherein a suitable catalyst is defined as a galactosyltransferase or a galactosyltransferase comprising a mutant catalytic domain, wherefore Su(A)$_x$-P is a substrate; wherein a glycan comprising a terminal GlcNAc-moiety is a glycan according to formula (101) or (102), as defined above; and wherein a modified glycoprotein is defined as a glycoprotein comprising a modified glycan according to formula (105) or (106), wherein (105) and (106) are as defined above.

More preferably, the modified glycoprotein obtainable by the here described process is a glycoprotein according to formula (107) or (108), wherein Pr, b, d, e, y and Su(A)$_x$, as well as their preferred embodiments, are as defined above.

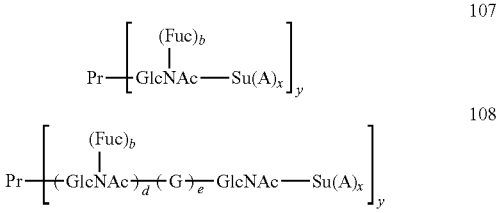

Su(A)$_x$ and preferred embodiments thereof are described in more detail below.

The process for the preparation of a modified glycoprotein according to the invention is performed in the presence of a suitable catalyst. A suitable catalyst is defined as a galactosyltransferase, or a galactosyltransferase comprising a mutant catalytic domain, wherefore Su(A)$_x$-P is a substrate.

When the catalyst is a galactosyltransferase, said galactosyltransferase preferably is a wild-type galactosyltransferase. When the catalyst is a galactosyltransferase comprising a mutant catalytic domain, said mutant GalT domain may be present within a full-length GalT enzyme, but it may also be present in a recombinant molecule comprising a catalytic domain.

Preferably, the catalyst is selected from the group consisting of β(1,4)-galactosyltransferases, β(1,3)-N-galactosyltransferases, β(1,4)-galactosyltransferases comprising a mutant catalytic domain and β(1,3)-N-galactosyltransferases comprising a mutant catalytic domain.

In one embodiment, the catalyst is a wild-type galactosyltransferase, more preferably a wild-type β(1,4)-galactosyltransferase or a wild-type β(1,3)-N-galactosyltransferase, and even more preferably a wild-type β(1,4)-galactosyltransferase I. β(1,4)-Galactosyltransferase I is herein further referred to as GalT. Even more preferably, the β(1,4)-galactosyltransferase I is selected from the group consisting of a bovine β(1,4)-Gal-T1, a human β(1,4)-Gal-T1, a human β(1,4)-Gal-T2, a human β(1,4)-Gal-T3, a human β(1,4)-Gal-T4 and a human β(1,3)-Gal-T5.

This embodiment wherein the catalyst is a wild-type galactosyltransferase is particularly preferred when a functional group A in sugar derivative Su(A)$_x$ is present on C2 or C6, preferably C6, of said sugar derivative. In this embodiment, it is further preferred that Su(A)$_x$ comprises not more than one functional group A, i.e. preferably x is 1. Su(A)$_x$ and Su(A)$_x$-P are described in more detail below.

The invention thus also relates to a process for the preparation of a modified glycoprotein, said process comprising a step of attaching, in the presence of a suitable catalyst, a modified sugar to a terminal GlcNAc-moiety on a glycoprotein; wherein a modified sugar is defined as a sugar comprising a functional group A wherein A is independently selected from the group consisting of a thiol group or a precursor thereof, a halogen, a sulfonyloxy group, a halogenated acetamido group, a mercaptoacetamido group and a sulfonated hydroxyacetamido group; and wherein a suitable catalyst is defined as a wild-type galactosyltransferase or a galactosyltransferase comprising a mutant catalytic domain, wherefore Su(A)$_x$-P is a substrate; with the proviso that when the catalyst is a wild-type galactosyltransferase, said modified sugar comprises not more than one functional group A and said functional group A is present on C6 of said modified sugar.

In a further embodiment, the invention relates to a process for the preparation of a modified glycoprotein, the process comprising contacting a glycoprotein comprising a glycan according to formula (101) or (102) as defined above with Su(A)$_x$-P in the presence of a suitable catalyst; wherein Su(A)$_x$ is a sugar derivative Su comprising x functional groups A wherein x is 1, 2, 3 or 4 and A is independently selected from the group consisting of a thiol group or a precursor thereof, a halogen, a sulfonyloxy group, a halogenated acetamido group, a mercaptoacetamido group and a sulfonated hydroxyacetamido group; wherein P is a nucleotide; and wherein a suitable catalyst is defined as a wild-type galactosyltransferase or a galactosyltransferase comprising a mutant catalytic domain, wherefore Su(A)$_x$-P is a substrate; with the proviso that when the catalyst is a wild-type galactosyltransferase, Su(A)$_x$-P comprises one functional group A (x is 1), and said functional group A is present on C2 or C6 of Su(A)$_x$, preferably C6.

Preferably, the wild-type galactosyltransferase is a β(1,4)-galactosyltransferase or a β(1,3)-N-galactosyltransferase, more preferably a β(1,4)-galactosyltransferase.

In another embodiment the catalyst is a galactosyltransferase comprising a mutant catalytic domain, preferably a β(1,4)-galactosyltransferase comprising a mutant catalytic domain or a β(1,3)-N-galactosyltransferase comprising a mutant catalytic domain, more preferably a β(1,4)-galactosyltransferase comprising a mutant catalytic domain. β(1,4)-Galactosyltransferase I is herein further referred to as GalT.

In another embodiment the catalyst is selected from the group consisting of β(1,4)-galactosyltransferases or β(1,3)-N-galactosyltransferases, more preferably from the group of β(1,4)-galactosyltransferases or β(1,3)-N-galactosyltransferases, all comprising a mutant catalytic domain.

In a preferred embodiment the catalyst is a β(1,3)-N-galactosyltransferase comprising a mutant catalytic domain, and preferably said β(1,3)-N-galactosyltransferase is a human β(1-3)-Gal-T5.

More preferably, the catalyst is a β(1,4)-N-galactosyltransferase comprising a mutant catalytic domain, more preferably, a β(1,4)-galactosyltransferase I comprising a mutant catalytic domain, and even more preferably selected from the group consisting of a bovine β(1,4)-Gal-T1, a human β4-Gal-T1, a human β(1,4)-Gal-T2, a human β(1,4)-Gal-T3 and a human β(1,4)-Gal-T4, all comprising a mutant catalytic domain.

Most preferably the catalyst is a bovine β(1,4)-Gal-T1 comprising a mutant catalytic domain.

Several suitable catalysts for the process according to the invention are known in the art. A suitable catalyst is for example a catalyst that comprises a mutant catalytic domain from a β(1,4)-galactosyltransferase I. A catalytic domain herein refers to an amino acid segment that folds into a domain that is able to catalyze the linkage of the specific sugar derivative nucleotide $Su(A)_x$-P to the terminal non-reducing GlcNAc-glycan in a specific process according to the invention. β(1,4)-galactosyltransferase I is herein further referred to as GalT. Such mutant GalT catalytic domains are for example disclosed in *J. Biol. Chem.* 2002, 277, 20833 and WO 2004/063344 (National Institutes of Health), incorporated by reference herein. *J. Biol. Chem.* 2002, 277, 20833 and WO 2004/063344 disclose Tyr-289 mutants of bovine β(1,4)-Gal-T1, which are referred to as Y289L, Y289N and Y289I. The method of preparation of said mutant catalytic domains Y289L, Y289N and Y289I is disclosed in detail in WO 2004/063344, p. 34, l. 6-p. 36, l. 2, expressly incorporated by reference herein.

Mutant GalT domains that catalyze the formation of a glucose-β(1,4)-N-acetylglucosamine bond are disclosed in WO 2004/063344 on p. 10, 1, 25-p. 12, 1. 4 (expressly incorporated by reference herein). Mutant GalT domains that catalyze the formation of an N-acetylgalactosamine-β(1,4)-N-acetylglucosamine bond are disclosed in WO 2004/063344 on p. 12, 1, 6-p. 13, 1. 2 (expressly incorporated by reference herein). Mutant GalT domains that catalyze the formation of a N-acetylglucosamine-β(1,4)-N-acetylglucosamine bond and a mannose-β(1,4)-N-acetylglucosamine bond are disclosed in WO 2004/063344 on p. 12, 1, 19-p. 14, 1. 6 (expressly incorporated by reference herein).

The disclosed mutant GalT domains may be included within full-length GalT enzymes, or in recombinant molecules containing the catalytic domains, as is disclosed in WO 2004/063344 on p. 14, 1, 31-p. 16, 1. 28, expressly incorporated by reference herein.

Another mutant GalT domain is for example Y284L, disclosed by Bojarová et al., *Glycobiology* 2009, 19, 509, expressly incorporated by reference herein, wherein Tyr284 is replaced by leucine.

Another mutant GalT domain is for example R228K, disclosed by Qasba et al., *Glycobiology* 2002, 12, 691, expressly incorporated by reference herein, wherein Arg228 is replaced by lysine.

The catalyst may also comprise a mutant catalytic domain from a bovine β(1,4)-galactosyltransferase, selected from the group consisting of GalT Y289N, GalT Y289F, GalT Y289M, GalT Y289V, GalT Y289G, GalT Y289I and GalT Y289A, preferably selected from the group consisting of GalT Y289F and GalT Y289M. GalT Y289N, GalT Y289F, GalT Y289M, GalT Y289V, GalT Y289G, GalT Y289I and GalT Y289A may be provided via site-directed mutagenesis processes, in a similar manner as disclosed in WO 2004/063344, in Qasba et al., *Prot. Expr. Pur.* 2003, 30, 219 and in Qasba et al., *J. Biol. Chem.* 2002, 277, 20833 (all incorporated by reference) for Y289L, Y289N and Y289I. In GalT Y289N the tyrosine amino acid (Y) at position 289 is replaced by an asparagine (N) amino acid, in GalT Y289F the tyrosine amino acid (Y) at position 289 is replaced by a phenyl alanine (F) amino acid, in GalT Y289M said tyrosine is replaced by a methionine (M) amino acid, in GalT Y289V by a valine (V) amino acid, in GalT Y289G by a glycine (G) amino acid, in GalT Y289I by an isoleucine (I) amino acid and in Y289A by an analine (A) amino acid.

In a preferred embodiment of the process for the preparation of a modified glycoprotein according to the invention, said catalyst is a catalyst comprising a mutant catalytic domain from a β(1,4)-galactosyltransferase, preferably from a bovine β(1,4)-Gal-T1.

Preferably, the catalyst is a catalyst comprising a mutant catalytic domain from a β(1,4)-galactosyltransferase, preferably selected from the group consisting of bovine β(1,4)-Gal-T1 GalT Y289L, GalT Y289N, GalT Y289I, GalT Y289F, GalT Y289M, GalT Y289V, GalT Y289G and GalT Y289A, more preferably selected from the group consisting of bovine β(1,4)-Gal-T1 GalT Y289L, GalT Y289N and GalT Y289I.

In a further preferred embodiment, said catalyst is a catalyst comprising a GalT mutant catalytic domain selected from the group consisting of Y289L, Y289N, Y289I, Y284L, R228K, Y289F, Y289M, Y289V, Y289G and Y289A, preferably selected from the group consisting of Y289L, Y289N, Y289I, Y284L and R228K. In another preferred embodiment, said catalyst is a catalyst comprising a bovine β(1,4)-Gal-T1 mutant catalytic domain selected from the group consisting of Y289F, Y289M, Y289V, Y289G and Y289A. More preferably said catalyst is a catalyst comprising a GalT mutant catalytic domain selected from the group consisting of Y289L, Y289N and Y289I, and most preferably said catalyst is a catalyst comprising a GalT mutant catalytic domain selected from the group consisting of Y289L.

Another type of suitable catalysts is a catalyst based on α(1,3)-N-galactosyltransferase (further referred to as α3Gal-T), preferably α(1,3)-N-acetylgalactosaminyltransferase (further referred to as α3GalNAc-T), as disclosed in WO 2009/025646, incorporated by reference herein. Mutation of α3Gal-T can broaden donor specificity of the enzyme, and make it an α3GalNAc-T. Mutation of α3GalNAc-T can broaden donor specificity of the enzyme. Polypeptide fragments and catalytic domains of α(1,3)-N-acetylgalactosaminyltransferases are disclosed in WO 2009/025646 on p. 26, 1. 18-p. 47, 1. 15 and p. 77, 1. 21-p. 82, 1. 4 (both expressly incorporated by reference herein).

The process for the preparation of a modified glycoprotein according to the invention is preferably performed in a suitable buffer solution, such as for example phosphate, buffered saline (e.g. phosphate-buffered saline, tris-buffered saline), citrate, HEPES, tris and glycine. Suitable buffers are known in the art. Preferably, the buffer solution is phosphate-buffered saline (PBS) or tris buffer.

The process is preferably performed at a temperature in the range of about 4 to about 50° C., more preferably in the range of about 10 to about 45° C., even more preferably in the range of about 20 to about 40° C., and most preferably in the range of about 30 to about 37° C.

The process is preferably performed a pH in the range of about 5 to about 9, preferably in the range of about 5.5 to about 8.5, more preferably in the range of about 6 to about 8. Most preferably, the process is performed at a pH in the range of about 7 to about 8.

$Su(A)_x$ is defined as a sugar derivative Su comprising x functional groups A, wherein A is independently selected from the group consisting of a thiol group or a precursor thereof, a halogen, a sulfonyloxy group, a halogenated acetamido group, a mercaptoacetamido group and a sulfonated hydroxyacetamido group, and wherein x is 1, 2, 3 or 4.

A $Su(A)_x$-moiety may also be referred to as a "modified sugar". A modified sugar is herein defined as a sugar or a sugar derivative, said sugar or sugar derivative comprising 1, 2, 3 or 4 functional groups A, wherein A is selected from the group consisting of a thiol group or a precursor thereof, a halogen, a sulfonyloxy group, a halogenated acetamido group, a mercaptoacetamido group and a sulfonated hydroxyacetamido group. When a modified sugar or sugar derivative comprises e.g. a thiol group, said sugar or sugar derivative may be referred to as a thiol-modified sugar or sugar derivative. When a modified sugar or sugar derivative comprises e.g. a thiol-precursor group, said sugar or sugar derivative may be referred to as a thiol-precursor-modified sugar or sugar derivative. When a modified sugar or sugar derivative comprises e.g. a halogen, said sugar or sugar derivative may be referred to as a halogen-modified sugar or sugar derivative. When a modified sugar or sugar derivative comprises e.g. a sulfonyloxy group, said sugar or sugar derivative may be referred to as a sulfonyloxy-modified sugar or sugar derivative.

A thiol group is herein defined as a $-[C(R^7)_2]_oSH$ group, wherein $R^7$ is independently selected from the group consisting of hydrogen, halogen and an (optionally substituted) $C_1$-$C_{24}$ alkyl group, and o is 0-24. Preferably $R^7$ is hydrogen or a $C_1$, $C_2$, $C_3$ or $C_4$ alkyl group, more preferably $R^7$ is hydrogen or $-CH_3$. Preferably o is 0-10, more preferably 0, 1, 2, 3, 4, 5 or 6. More preferably, $R^7$ is hydrogen, $-CH_3$ or a $C_2$ alkyl group and/or o is 0, 1, 2, 3 or 4. Even more preferably $R^7$ is hydrogen and o is 0, 1, 2 or 3, more preferably o is 1 or 2, most preferably o is 0 or 1. Most preferably o is 0. Most preferably, said thiol group is $-CH_2CH_2CH_2SH$, $-CH_2CH_2SH$, $-CH_2SH$ or $-SH$, preferably $-SH$.

A precursor of a thiol group is herein defined as a $-[C(R^7)_2]_oSC(O)CH_3$ group, wherein $R^7$ and o, as well as their preferred embodiments, are as defined above for a thiol group. Most preferably, said thiol-precursor is $-CH_2CH_2CH_2SC(O)CH_3$, $-CH_2CH_2SC(O)CH_3$, $-CH_2SC(O)CH_3$ or $-SC(O)CH_3$, preferably $-SC(O)CH_3$. In the process for the preparation of a modified glycoprotein according to the invention, a sugar derivative $Su(A)_x$ wherein A is a precursor of a thiol group may be used. During said process, the thiol-precursor is converted to a thiol group.

A halogen is herein defined as F, Cl, Br or I. Preferably, said halogen is Cl or Br, more preferably Cl.

A sulfonyloxy group is herein defined as a $-[C(R^7)_2]_oOS(O)_2R^8$ group, wherein $R^7$ and o are as defined above for a thiol group, and $R^8$ is selected from the group consisting of $C_1$-$C_{24}$ alkyl groups, $C_6$-$C_{24}$ aryl groups, $C_7$-$C_{24}$ alkylaryl groups and $C_7$-$C_{24}$ arylalkyl groups. $R^8$ is preferably a $C_1$-$C_4$ alkyl group, a $C_6$-$C_{12}$ aryl group, a $C_7$-$C_{12}$ alkylaryl group or a $C_7$-$C_{12}$ arylalkyl group, more preferably a $C_1$-$C_4$ alkyl group, a $C_7$-$C_{12}$ alkylaryl group or a $C_7$-$C_{12}$ arylalkyl group, even more preferably $-CH_3$, $-C_2H_5$, a $C_3$ linear or branched alkyl group, a phenyl group or a $C_7$ alkylaryl group. $R^8$ is most preferably a methyl group, an ethyl group, a phenyl group or a p-tolyl group. Preferably $R^7$ is hydrogen or a $C_1$, $C_2$, $C_3$ or $C_4$ alkyl group, more preferably $R^7$ is hydrogen or $-CH_3$. Preferably o is 0-10, more preferably 0, 1, 2, 3, 4, 5 or 6. More preferably, $R^7$ is hydrogen, $-CH_3$ or a $C_2$ alkyl group and/or o is 0, 1, 2, 3 or 4. Even more preferably $R^7$ is hydrogen and o is 1 or 2, most preferably o is 0. $R^8$ is preferably a $C_1$-$C_4$ alkyl group, a $C_7$-$C_{12}$ alkylaryl group or a $C_7$-$C_{12}$ arylalkyl group, more preferably $-CH_3$, $-C_2H_5$, a $C_3$ linear or branched alkyl group or a $C_7$ alkylaryl group. Most preferably the sulfonyloxy group is a mesylate group, $-OS(O)_2CH_3$, a benzenesulfonate group ($-OS(O)_2(C_6H_5)$) or a tosylate group ($-OS(O)_2(C_6H_4CH_3)$).

A halogenated acetamido group is herein defined as an $-NHC(O)[C(R^7)_2]_oX$ group, wherein $R^7$ is independently selected from the group consisting of hydrogen, halogen and an (optionally substituted) $C_1$-$C_{24}$ alkyl group, X is F, Cl, Br or I, and o is 0-24. Preferably $R^7$ is hydrogen or a $C_1$, $C_2$, $C_3$ or $C_4$ alkyl group, more preferably $R^7$ is hydrogen or $-CH_3$, most preferably hydrogen. Preferably o is 0 to 10, more preferably 1, 2, 3, 4, 5 or 6, even more preferably 1, 2, 3 or 4 and most preferably o is 1. More preferably, $R^7$ is hydrogen, $-CH_3$ or a $C_2$ alkyl group and/or o is 1, 2, 3 or 4 and most preferably $R^7$ is hydrogen and o is 1. Preferably, X is Cl or Br, more preferably X is Cl. Most preferably, $R^7$ is hydrogen, X is Cl and o is 1.

A mercaptoacetamido group is herein defined as an $-NHC(O)[C(R^7)_2]_oSH$ group, wherein $R^7$ is independently selected from the group consisting of hydrogen, halogen and an (optionally substituted) $C_1$-$C_{24}$ alkyl group and o is 0-24. Preferably $R^7$ is hydrogen or a $C_1$, $C_2$, $C_3$ or $C_4$ alkyl group, more preferably $R^7$ is hydrogen or $-CH_3$, most preferably hydrogen. Preferably o is 0 to 10, more preferably 1, 2, 3, 4, 5 or 6, even more preferably 1, 2, 3 or 4 and most preferably o is 2, 3 or 4. More preferably, $R^7$ is hydrogen, $-CH_3$ or a $C_2$ alkyl group and/or o is 1, 2, 3 or 4. More preferably, $R^7$ is hydrogen and o is 1, 2, 3 or 4. Most preferably, $R^7$ is hydrogen and o is 1, 2 or 3, preferably 1. Preferred examples include a mercaptoethanoylamido group, a mercaptopropanoylamido group, a mercaptobutanoylamido group and a mercapto-pentanoylamido group, preferably a mercaptopropanoylamido group.

A sulfonated hydroxyacetamido group is herein defined as a $-NHC(O)[C(R^7)_2]_oOS(O)_2R^8$ group, wherein $R^7$ is independently selected from the group consisting of hydrogen, halogen and an (optionally substituted) $C_1$-$C_{24}$ alkyl group, $R^8$ is selected from the group consisting of $C_1$-$C_{24}$ alkyl groups, $C_6$-$C_{24}$ aryl groups, $C_7$-$C_{24}$ alkylaryl groups and $C_7$-$C_{24}$ arylalkyl groups, and o is 0-24. $R^8$ is preferably a $C_1$-$C_4$ alkyl group, a $C_6$-$C_{12}$ aryl group, a $C_7$-$C_{12}$ alkylaryl group or a $C_7$-$C_{12}$ arylalkyl group, more preferably $-CH_3$, $-C_2H_5$, a $C_3$ linear or branched alkyl group, a $C_6$-$C_9$ aryl group or a $C_7$ alkylaryl group. Most preferably the sulfonyloxy group is a mesylate group $-OS(O)_2CH_3$, a benzenesulfonate group $-OS(O)_2(C_6H_5)$ or a tosylate group $-OS(O)_2(C_6H_4CH_3)$. Preferably $R^7$ is hydrogen or a $C_1$, $C_2$, $C_3$ or C$_4$ alkyl group, more preferably R$^7$ is hydrogen or —CH$_3$, most preferably hydrogen. Preferably o is 0 to 10, more preferably 1, 2, 3, 4, 5 or 6, even more preferably 1, 2, 3 or 4 and most preferably o is 1. More preferably, R$^7$ is hydrogen, —CH$_3$ or a C$_2$ alkyl group and/or o is 1, 2, 3 or 4. Even more preferably R$^7$ is hydrogen and o is 1, 2 or 3. Yet even more preferably, R$^7$ is H, o is 1 and R$^8$ is a mesylate group, a benzenesulfonate group or a tosylate group. Most preferably, R$^7$ is hydrogen, R$^8$ is —CH$_3$ and o is 1.

The sugar derivative Su(A)$_x$ may comprise one or more functional groups A. When Su(A)$_x$ comprises two or more functional groups A, each functional group A is independently selected, i.e. one Su(A)$_x$ may comprise different functional groups A, e.g. a thiol group and a halogen, etc. In a preferred embodiment, x is 1 or 2, more preferably x is 1. In another preferred embodiment, functional group A is a thiol or a halogen, more preferably a halogen.

Sugar derivative Su(A)$_x$ is derived from a sugar or a sugar derivative Su, e.g. an amino sugar or an otherwise derivatized sugar. Examples of sugars and sugar derivatives include galactose (Gal), mannose (Man), glucose (Glc), N-acetylneuraminic acid or sialic acid (Sial) and fucose (Fuc).

An aminosugar is a sugar wherein a hydroxyl (OH) group is replaced by an amine group and examples include glucosamine (GlcNH$_2$) and galactosamine (GalNH$_2$). Examples of an otherwise derivatized sugar include N-acetylneuraminic acid (sialic acid, Sia or NeuNAc) or fucose (Fuc).

Sugar derivative Su(A)$_x$ is preferably derived from galactose (Gal), mannose (Man), N-acetylglucosamine (GlcNAc), glucose (Glc), N-acetylgalactosamine (GalNAc), fucose (Fuc) and N-acetylneuraminic acid (sialic acid Sia or NeuNAc), preferably from the group consisting of GlcNAc, Glc, Gal and GalNAc. More preferably Su(A)$_x$ is derived from Gal or GalNAc, and most preferably Su(A)$_x$ is derived from GalNAc.

The one or more functional groups A in Su(A)$_x$ may be linked to the sugar or sugar derivative Su in several ways. The one or more functional groups A may be bonded to C2, C3, C4 and/or C6 of the sugar or sugar derivative, instead of a hydroxyl (OH) group. It should be noted that, since fucose lacks an OH-group on C6, if A is bonded to C6 of Fuc, then A takes the place of an H-atom. Preferably, the one or more functional groups A in Su(A)$_x$ may be present on C2 and/or C6 of the sugar or sugar derivative Su. When a functional group A is present instead of an OH-group on C2 of a sugar or sugar derivative, A is preferably selected from the group consisting of a halogenated acetamido group, a mercaptoacetamido group and a sulfonated hydroxyacetamido group. However, when A is present on C2 of a 2-aminosugar derivative, e.g. GalNAc or GlcNAc, A is preferably selected from the group consisting of a halogen, a thiol group and a sulfonyloxy group.

When A is a thiol group, it is preferred that said thiol group is present on the 6-position of a sugar derivative or on a 2-aminosugar derivative. An example of Su(A)x wherein A is a thiol group is 2-(mercaptoacetamido)-2-deoxy-galactose (2-GalNAcSH). Another example of Su(A)x wherein A is a thiol group is 6-mercapto-6-deoxy-galactose.

When A is a halogen, it is preferred that said halogen is present on the 6-position of a sugar derivative or on a 2-amino sugar derivative. An example of Su(A)x wherein A is a halogen is 2-(chloroacetamido)-2-deoxy-galactose (2-GalNAcCl). Another example of Su(A)x wherein A is a halogen is 6-iodo-6-deoxy-galactose. Another example of Su(A)x wherein A is a halogen is 6-(chloroacetamido)-6-deoxy-galactose.

When A is a sulfonyloxy group, it is preferred that said sulfonyloxy group is present on the 6-position of a sugar derivative or on a 2-amino sugar derivative. An example of Su(A)x wherein A is a sulfonyloxy group is 2-(methylsulfonyloxyacetamido)-2-deoxy-galactose (2-GalNAcOMs). Another example of Su(A)x wherein A is a sulfonyloxy group is 2-(benzenesulfonyloxyacetamido)-2-deoxy-galactose (2-GalNAcOMs. Another example of Su(A)x wherein A is a sulfonyloxy group is 6-(methyl sulfonyl)-galactose.

When A is a halogenated acetamido group, a mercaptoacetamido group or a sulfonated hydroxyacetamido group it is preferred that said groups are present on the 6-position of a sugar derivative.

Further examples of Su(A)$_x$-P include 6-A-6-deoxygalactose-UDP (6-A-Gal-UDP), such as 6-chloro-6-deoxygalactose-UDP (6-ClGal-UDP), 6-thio-6-deoxygalactose-UDP (6-HSGal-UDP) or 2-A-2-deoxygalactose-UDP (2-A-Gal-UDP), such as 2-chloro-2-deoxygalactose-UDP (2-ClGal-UDP), 2-thio-2-deoxygalactose-UDP (2-HSGal-UDP). Alternatively, A may be indirectly substituted to the sugar derivative as part of an acetamido group that in turn is substituting a hydroxyl group. Examples include 6-A-acetamido-6-deoxygalactose-UDP (6-GalNAcA-UDP), such as 6-chloroacetamido-6-deoxygalactose-UDP (6-GalNAcCl-UDP, (23) with X=Cl), 6-thioacetamido-6-deoxygalactose-UDP (6-GalNAcSH-UDP, (20) with 1 CH$_2$ and R=H) or 2-A-acetamido-2-deoxygalactose-UDP (2-GalNAcA-UDP), such as 2-chloroacetamido-2-deoxygalactose-UDP (2-GalNAcCl-UDP, (21) with X=Cl), 2-thioacetamido-2-deoxy-galactose-UDP (2-GalNAcSH-UDP, (18) with 1 CH$_2$ and R=H). Alternatively, A may be indirectly substituted to the sugar derivative as part of another functional group that in turn is substituting a hydroxyl group or is attached to a hydroxyl group. Examples of such other functional group include an (hetero)alkyl chain or a (hetero)aryl chain.

P is herein defined as a nucleotide. P is preferably selected from the group consisting of a nucleoside monophosphate and a nucleoside diphosphate, more preferably from the group consisting of uridine diphosphate (UDP), guanosine diphosphate (GDP), thymidine diphosphate (TDP), cytidine diphosphate (CDP) and cytidine monophosphate (CMP), more preferably from the group consisting of uridine diphosphate (UDP), guanosine diphosphate (GDP), cytidine diphosphate and (CDP). Most preferably, P is UDP.

Several compounds of formula Su(A)$_x$-P, wherein a nucleoside monophosphate or a nucleoside diphosphate P is linked to a sugar derivative Su(A)x, are known in the art. For example Wang et al., Chem. Eur. J, 2010, 16, 13343-13345, Piller et al., ACS Chem. Biol. 2012, 7, 753, Piller et al., Bioorg. Med. Chem. Lett. 2005, 15, 5459-5462 and WO 2009/102820 (Qasba et al.), all incorporated by reference herein, disclose a number of compounds Su(A)x-P and their syntheses.

Several examples (18-23) of uridine diphosphates linked to thiol-, halo- and mesityloxy-substitued sugars and sugar derivatives, Su(A)$_x$-UDP, are shown below. Also an example of Su(A)$_x$-P wherein A is a thiol precursor (18-20, with R=Ac), is shown. As described above, in 18-20 it is preferred that o is 1, 2, 3, 4, 5 or 6, preferably 1, 2, 3 or 4, more preferably 1, 2 or 3. Furthermore, R is H or Ac.

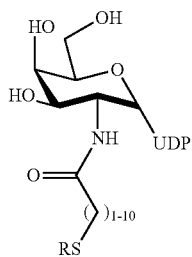

18

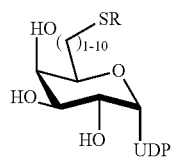

19

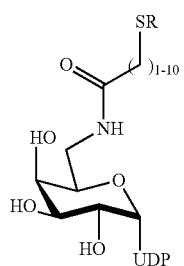

R = H, Ac

21

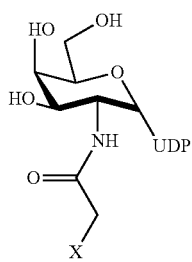

22

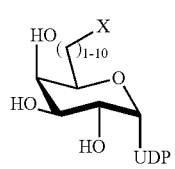

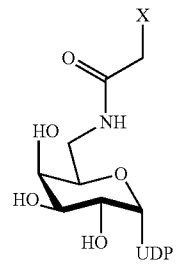

23

X = Cl, Br, I, OMs
UDP =

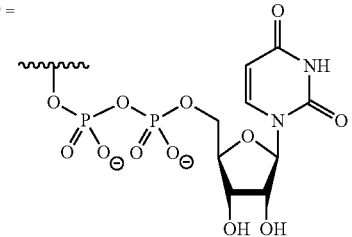

20

Figure 3:
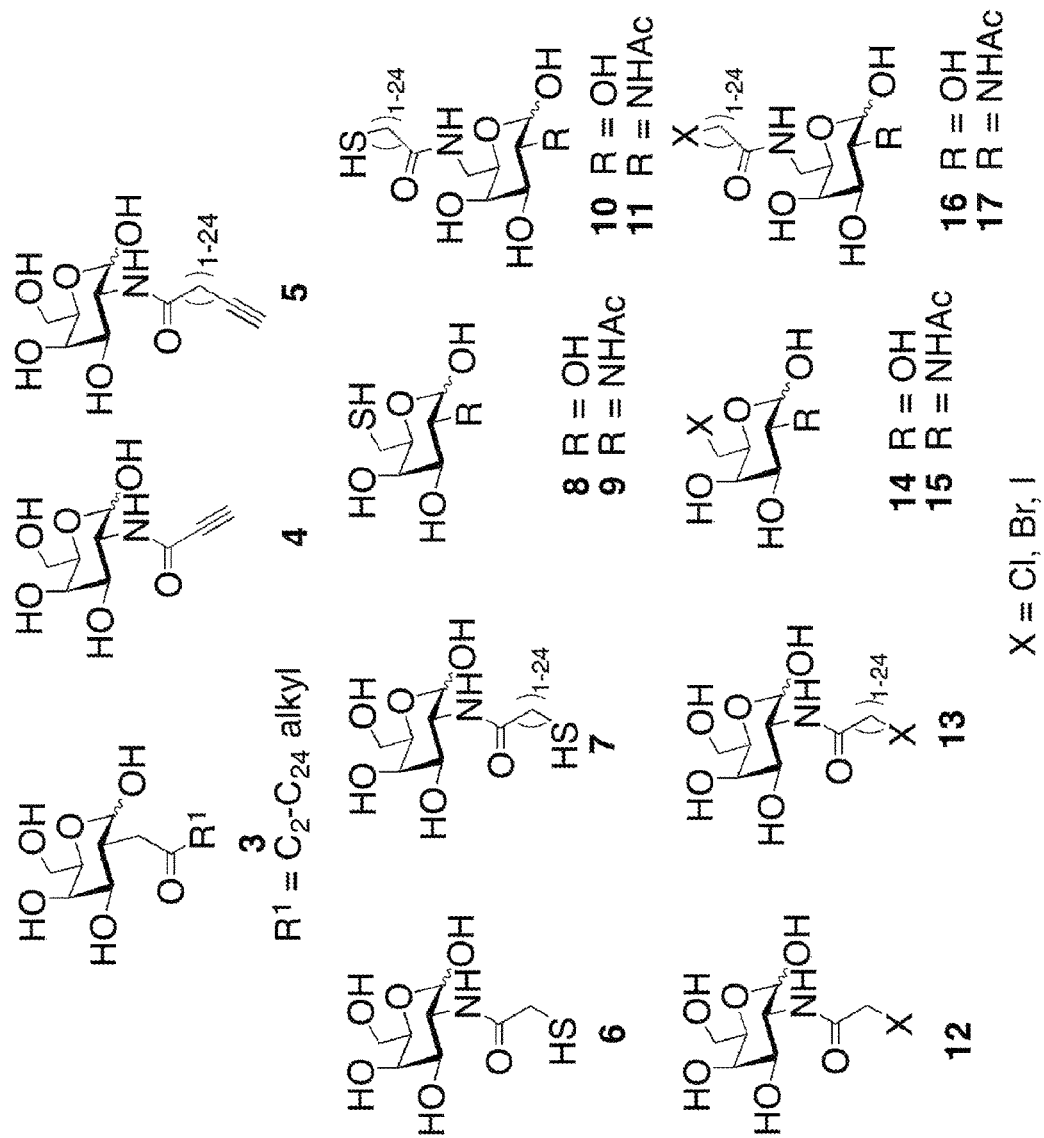
FIG. 3 shows the structures of modified galactose derivatives (3-17) for transfer onto a GlcNAc-terminated sugar under the action of a galactosyl transferase (or a mutant thereof).
Figure 4:
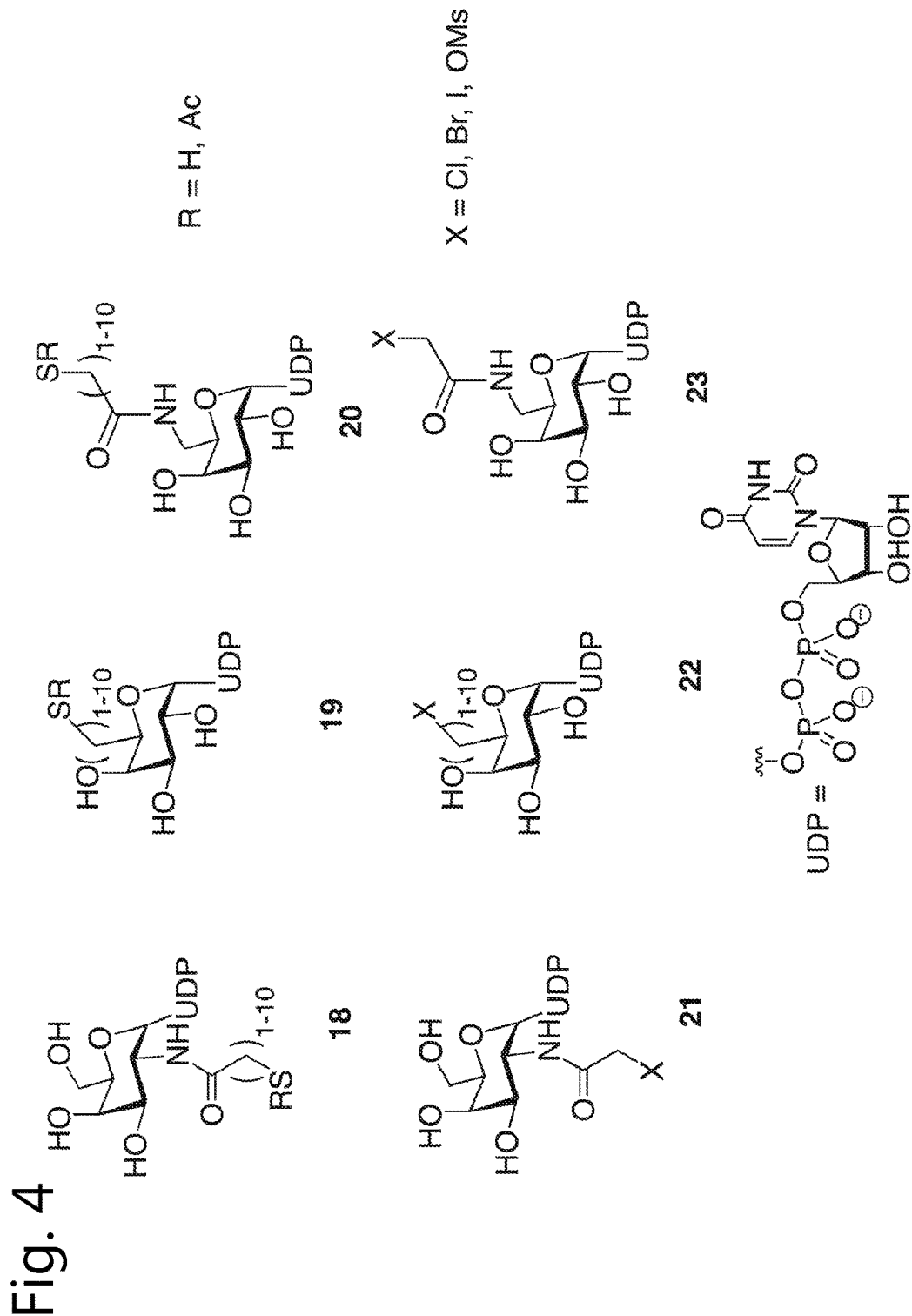
FIG. 4 shows a range of thiol-derivatives or halogen derivatives of UDP-galactose (18-23) that may be transferred onto a GlcNAc-terminated sugar under the action of a galactosyl transferase (or a mutant thereof).
Figure 5:
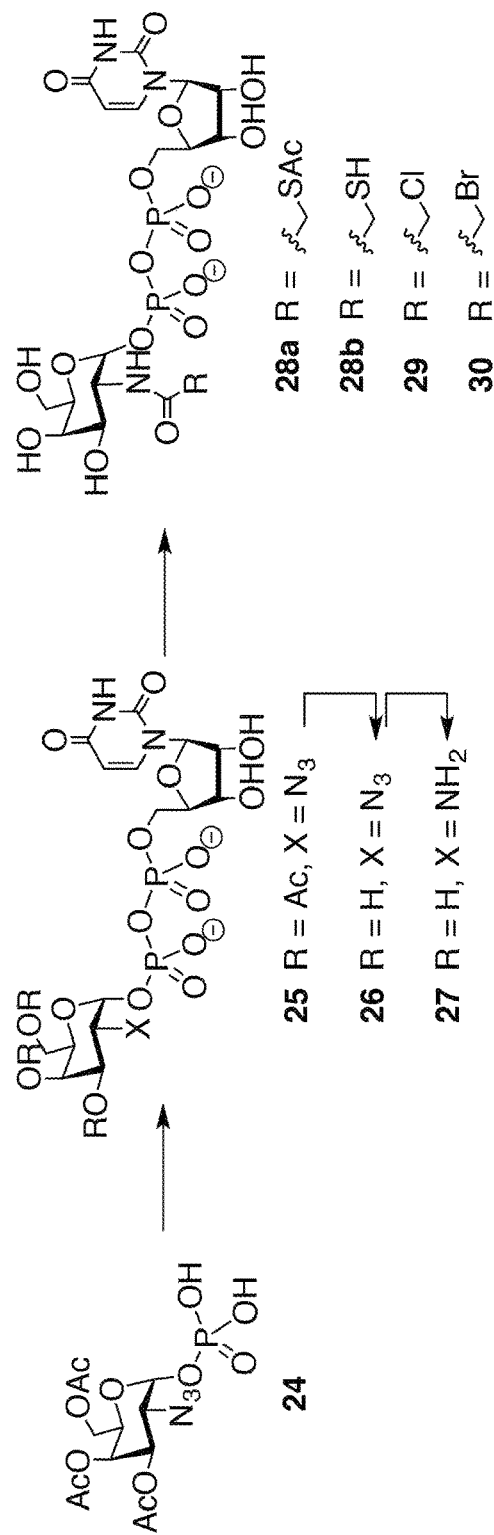
FIG. 5 shows the scheme for the synthetic preparation of an acetyl-protected thiol variant (28a) or the deacetylated thiol variant (28b) or halogen variants (29+30) of UDP-GalNAc, substituted on the 2-NHAc moiety.

Additional examples (3-17) of keto-, alkynyl-, halogen, thiol, thiolated acetamido- and halogenated acetamido-substituted sugars and sugar derivatives are shown in FIG. 3, all of which may be converted into their corresponding UDP sugars Su(A)$_x$-UDP, some of which are depicted in FIG. 4. The synthesis of some of the thiol derivatives or halogenated acetamide derivatives, all of which can be readily prepared from the common precursor 27, is depicted in FIG. 5.

As was described above, several of the sugar derivative nucleotides Su(A)$_x$-P that may be employed in the process for the preparation of a modified glycoprotein according to the invention are a substrate for a wild type galactosyltransferase. For these sugar derivative nucleotides Su(A)$_x$-P, the process according to the invention may be performed in the presence of a wild type galactosyltransferase, preferably a wild type β(1,4)-galactosyltransferase, more preferably a β(1,4)-galactosyltransferase I, as a catalyst.

When a wild type galactosyltransferase is used as a catalyst, it is preferred that Su(A)$_x$-P is selected from the group consisting of Su(A)$_x$-P wherein x is 1 and wherein A is present on C6 of the sugar or sugar derivative, and wherein A is as defined above. A may be directly substituted to the sugar derivative instead of an hydroxyl group. Examples include 6-A-6-deoxygalactose-UDP (6-A-Gal-UDP), 6-chloro-6-deoxygalactose-UDP (6-ClGal-UDP, (22) with 1 CH$_2$ and X=6-thio-6-deoxygalactose-UDP (6-HSGal-UDP, (19) with 1 CH$_2$ and R=H)

Alternatively, A may be indirectly substituted to the sugar derivative as part of an acetamido group that in turn is substituting a hydroxyl group. Examples include 6-A-acetamido-6-deoxygalactose-UDP (6-GalNAcA-UDP), such as 6-chloroacetamido-6-deoxygalactose-UDP (6-GalNAcCl-UDP, (23) with X=6-thioacetamido-6-deoxygalactose-UDP (6-GalNAcSH-UDP, (20) with 1 CH$_2$ and R=H). Alternatively, A may be indirectly substituted to the sugar derivative as part of another functional group that in turn is substituting a hydroxyl group or is attached to a hydroxyl group. Examples of such other functional group include an (hetero) alkyl chain or a (hetero)aryl chain.

In a preferred embodiment of the process for the preparation of a modified glycoprotein, Su(A)$_x$ comprises 1 or 2 functional groups A, i.e. preferably x is 1 or 2. More preferably, x is 1. In a preferred embodiment, Su is galactose (Gal). In a further preferred embodiment, x is 1 or 2 and Su is Gal, and most preferably, x is 1 and Su is Gal.

In a preferred embodiment, Su(A)$_x$ is selected from the group consisting of 6-GalNAcCl, 6-GalNAcSH, 2-GalNAcCl, 2-GalNAcSH, 6-ClGal, 2-ClGal, 2-HSGal and 6-HSGal, more preferably form the group consisting of 6-GalNAcCl, 6-GalNAcSH, GalNAcCl, 2-GalNAcSH, 6-ClGal- and 2-ClGal.

In a further preferred embodiment, x is 1 and Su(A)$_x$ is selected from the group consisting of 6-GalNAcCl, 6-GalNAcSH, 2-GalNAcCl, 2-GalNAcSH, 6-ClGal, 2-ClGal, 2-HSGal and 6-HSGal, more preferably from the group consisting of 6-GalNAcCl, 6-GalNAcSH, 2-GalNAcCl, 2-GalNAcSH, 6-ClGal- and 2-ClGal.

In a preferred embodiment, A is a thiol group or a halogen.

In a particularly preferred embodiment of the process for the modification of a modified glycoprotein according to the invention, Su(A)$_x$ is selected from the group consisting of 2-GalNAcSH, 2-GalNAcX, 2-GalNAcOS(O)$_2$R$^8$, 6-GalNAcSH, 6-GalNAcX and 6-GalNAcOS(O)$_2$R$^8$. In an even more preferred embodiment, x is 1 or 2 and Su(A)$_x$ is selected from the group consisting of 2-GalNAcSH, 2-GalNAcX, 2-GalNAcOS(O)$_2$R$^8$, 6-GalNAcSH, 6-GalNAcX and 6-GalNAcOS(O)$_2$R$^8$. In a most preferred embodiment, x is 1 and Su(A)$_x$ is selected from the group consisting of 2-GalNAcSH, 2-GalNAcX, 2-GalNAcOS(O)$_2$R$^8$, 6-GalNAcSH, 6-GalNAcX and 6-GalNAcOS(O)$_2$R$^8$, wherein X is Cl or Br, preferably Cl.

In a particularly preferred embodiment of the process for the preparation of a modified glycoprotein according to the invention, Su(A)$_x$-P is selected from the group consisting of 2-GalNAcSH-UDP ((18) with 1 CH$_2$ and R=H), 2-GalNAcX-UDP (21), 2-GalNAcOS(O)$_2$R$^8$-UDP, 6-GalNAcSH-UDP ((20) with 1 CH$_2$ and R=H), 6-GalNAcX-UDP (23) and 6-GalNAcOS(O)$_2$R$^8$-UDP, and the catalyst is bovine β(1,4)-Gal-T1 comprising a mutant catalytic domain GalT (Y289L); wherein X is Cl, Br or I; and wherein R$^8$ is a methyl group, an ethyl group, a phenyl group or a p-tolyl group.

In a further preferred embodiment 2-GalNAcX-UDP is 2-GalNAcCl-UDP or 2-GalNAcBr-UDP, more preferably 2-GalNAcCl-UDP, and 6-GalNAcX-UDP is 6-GalNAcCl-UDP or 6-GalNAcBr-UDP, more preferably 6-GalNAcCl-UDP. In another preferred embodiment, R$^8$ in 2-GalNAcOS(O)$_2$R$^8$-UDP is methyl, phenyl or p-tolyl, most preferably methyl, and R$^8$ in 6-GalNAcOS(O)$_2$R$^8$-UDP is methyl, phenyl or p-tolyl, most preferably R$^8$ is methyl.

In another particularly preferred embodiment of the process for the preparation of a modified glycoprotein according to the invention, Su(A)$_x$-P is selected from the group consisting of 6-HSGal-UDP, 6-XGal-UDP, 6-R$^8$S(O)$_2$OGal-UDP, and the catalyst is a wild-type human GalT; wherein X is Cl, Br or I; and wherein R$^8$ is a methyl group, an ethyl group, a phenyl group or a p-tolyl group. X is more preferably Cl or Br, most preferably Cl. R$^8$ is more preferably methyl, phenyl or p-tolyl, most preferably methyl. The human GalT is preferably a human β4-Gal-T1, a human β(1,4)-Gal-T2, a human β(1,4)-Gal-T3 and a human β(1,4)-Gal-T4.

The process for the preparation of a modified glycoprotein according to the invention may further comprise a step comprising providing a glycoprotein comprising a glycan comprising a terminal GlcNAc-moiety at the non-reducing end. The invention thus also relates to a process for the preparation of a modified glycoprotein, the process comprising the steps of:

(i) providing a glycoprotein comprising a glycan comprising a terminal GlcNAc-moiety at the non-reducing end; and (ii) contacting a glycoprotein comprising a glycan comprising a terminal GlcNAc-moiety with Su(A)$_x$-P in the presence of a suitable catalyst; wherein Su(A)$_x$ is a sugar derivative Su comprising x functional groups A wherein x is 1, 2, 3 or 4 and wherein A is independently selected from the group consisting of a thiol group or a precursor thereof, a halogen, a sulfonyloxy group, a halogenated acetamido group, a mercaptoacetamido group and a sulfonated hydroxy acetamido group; wherein P is a nucleotide; wherein a suitable catalyst is defined as a galactosyltransferase or a galactosyltransferase comprising a mutant catalytic domain, wherefore Su(A)$_x$-P is a substrate; and wherein a glycan comprising a terminal GlcNAc-moiety is a glycan according to formula (101) or (102):

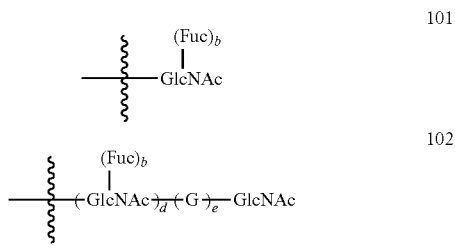

wherein b, d, e and G are as defined above.

Preferably, the catalyst in step(ii) is selected from the group consisting of β(1,4)-galactosyltransferases, β(1,3)-N-galactosyltransferases, β(1,4)-galactosyltransferases comprising a mutant catalytic domain and β(1,3)-N-galactosyltransferases comprising a mutant catalytic domain. The catalyst is described in more detail above.

A glycoprotein comprising a glycan comprising a terminal GlcNAc-moiety at the non-reducing end, i.e. a terminal non-reducing GlcNAc protein, may be provided in several ways, for example by (a) trimming of N-glycoprotein with an endo-glycosidase as described in *EMBO J.* 2001, 12, 3046 (incorporated by reference) or (b) expression of hybrid N-glycoprotein in the presence of swainsonine as for example described by Satoh et al. in *Glycobiology* 2006, 17, 104-118, incorporated by reference (followed by sialidase/galactosidase treatment).

In a particular embodiment, the invention also relates to a process for the preparation of a modified glycoprotein, the process comprising the steps of:

(i) providing a glycoprotein comprising a glycan comprising a terminal GlcNAc-moiety at the non-reducing end by trimming a glycoprotein comprising an oligosaccharide glycan by the action of an endo-glycosidase; and (ii) contacting a glycoprotein comprising a glycan comprising a terminal GlcNAc-moiety with Su(A)$_x$-P in the presence of a suitable catalyst; wherein Su(A)$_x$ is a sugar derivative Su comprising x functional groups A wherein x is 1, 2, 3 or 4 and wherein A is independently selected from the group consisting of a thiol group or a precursor thereof, a halogen, a sulfonyloxy group, a halogenated acetamido group, a mercaptoacetamido group and a sulfonated hydroxy acetamido group; wherein P is a nucleotide; wherein a suitable catalyst is defined as a galactosyltransferase or a galactosyltransferase comprising a mutant catalytic domain, wherefore Su(A)$_x$-P is a substrate; and wherein a glycan comprising a terminal GlcNAc-moiety is a glycan according to formula (101) or (102):

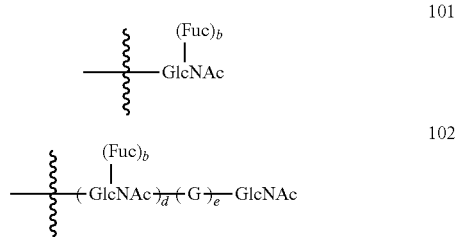

wherein b, d, e and G are as defined above.

Preferably, the catalyst is selected from the group consisting of β(1,4)-galactosyltransferases, β(1,3)-N-galactosyltransferases, β(1,4)-galactosyltransferases comprising a mutant catalytic domain and β(1,3)-N-galactosyltransferases comprising a mutant catalytic domain. The catalyst is described in more detail above.

A glycan may be attached to glycoprotein via C1 of a GlcNAc-residue, that is bonded to the amide side chain of an asparagine amino acid that is part of the glycoprotein. The oligosaccharide may be attached via an N-glycosidic bond, in most cases to an asparagine (Asn) or arginine (Arg) amino acid side chain.

Numerous different types of glycans exist. For example the Fc regions of Ig antibodies bear a highly conserved N-glycosylation site. The N-glycans attached to this site are predominantly core-fucosylated diantennary structures of the complex type. Another type of glycan is the class of high mannose glycans. High-mannose typically comprises two N-acetylglucosamines and a varying number of mannose residues.

As described above, a glycan may be bonded to the glycoprotein via a GlcNAc-residue, and this GlcNAc residue may be fucosylated. In FIG. 1, this is denoted by b: when b is 0, said GlcNAc-residue is non-fucosylated and when b is 1, said GlcNAc is fucosylated.

In a large number of glycans, a second GlcNAc-residue is bonded to the GlcNac-residue that is directly bonded to the glycoprotein, as is also seen in FIG. 1, (b) and (c). A glycan wherein a second GlcNAc-residue is bonded to the GlcNac-residue that is directly bonded to the glycoprotein (e.g. FIGS. 1(b) and (c)), can be trimmed in order to obtain a glycoprotein comprising a glycan comprising a terminal GlcNAc-moiety according to formula (101) at the non-reducing end. Trimming occurs in between said two GlcNAc-residues. Trimming of a glycan provides a glycan according to formula (101), as shown in FIG. 1 (a). Such a GlcNAc-residue that is covalently bonded to an N-glycosylation site, preferably via an N-glycosidic bond via C1 of said GlcNAc and an amide present in an amino acid side chain of the antibody, is herein referred to as a "terminal GlcNAc-moiety", and also "core-GlcNAc-moiety". Said terminal GlcNAc-moiety or core-GlcNAc-moiety is optionally fucosylated.

The trimming of a glycan occurs by the action of a suitable enzyme, and after trimming the oligosaccharide (also referred to as glycan) a terminal GlcNAc-moiety is obtained. By trimming, a glycan comprising a terminal GlcNAc-moiety according to formula (101) is obtained. This terminal GlcNAc-moiety may be fucosylated (b in FIG. 1(a) is 1) or non-fucosylated (b is 0).

A "suitable enzyme" is defined as an enzyme wherefore the oligosaccharide that is to be trimmed is a substrate. The preferred type of enzyme that is to be used in step (i) of this particular embodiment of the process according to the invention depends on the specific glycan or glycans that is or are trimmed. In a preferred embodiment of this particular embodiment of the process according to the invention, the enzyme in step (i) of this particular embodiment of the process is selected from the group of endo-glycosidases.

Endo-glycosidases are capable of cleaving internal glycosidic linkages in glycan structures, which provides a benefit to remodeling and synthetic endeavors. For example, endo-glycosidases can be employed for facile homogenization of heterogeneous glycan populations, when they cleave at predictable sites within conserved glycan regions. One of the most significant classes of endoglycosidases in this respect comprises the endo-β-N-acetylglucosaminidases (EC 3.2.1.96, commonly known as Endos and ENGases), a class of hydrolytic enzymes that remove N-glycans from glycoproteins by hydrolyzing the β-1,4-glycosidic bond in the N,N'-diacetylchitobiose core (reviewed by Wong et al. *Chem. Rev.* 2011, 111, 4259, incorporated by reference herein), leaving a single core N-linked GlcNAc residue. Endo-β-N-acetylglucosaminidases are found widely distributed through nature with common chemoenzymatic variants including Endo D, which is specific for pauci mannose; Endo A and Endo H, which are specific for high mannose; Endo F subtypes, which range from high mannose to biantennary complex; and Endo M, which can cleave most N-glycan structures (high mannose/complex-type/hybrid-type), except fucosylated glycans, and the hydrolytic activity for the high-mannose type oligosaccharides is significantly higher than that for the complex- and hybrid-type oligosaccharides. These ENGases show specificity toward the distal N-glycan structure and not the protein displaying it, making them useful for cleaving most N-linked glycans from glycoproteins under native conditions.

Endoglycosidases F1, F2, and F3 are most suitable for deglycosylation of native proteins. The linkage specificities of endo F1, F2, and F3 suggest a general strategy for deglycosylation of proteins that may remove all classes of N-linked oligosaccharides without denaturing the protein. Biantennary and triantennary structures can be immediately removed by endoglycosidases F2 and F3, respectively. Oligo-mannose and hybrid structures can be removed by Endo F1.

Endo F3 is unique in that its cleavage is sensitive to the state of peptide linkage of the oligosaccharide, as well as the state of core fucosylation. Endoglycosidase F3 cleaves asparagine-linked biantennary and triantennary complex oligosaccharides. It will cleave non-fucosylated biantennary and triantennary structures at a slow rate, but only if peptide-linked. Core fucosylated biantennary structures are efficient substrates for Endo F3, which activity up to 400-fold. There is no activity on oligomannose and hybrid molecules. See for example Tarentino et al. *Glycobiology* 1995, 5, 599, incorporated by reference herein.

Endo S is a secreted endoglycosidase from *Streptococcus pyogenes*, and also belongs to the glycoside hydrolase family 18, as disclosed by Collin et al. (*EMBO J.* 2001, 20, 3046, incorporated by reference herein). In contrast to the ENGases mentioned above, however, the endo S has a more defined specificity and is specific for cleaving only the conserved N-glycan in the Fc domain of human IgGs (no other substrate has been identified to date), suggesting that a protein-protein interaction between the enzyme and IgG provides this specificity.

Endo S49 is described in WO 2013/037824 (Genovis AB), incorporated by reference herein. Endo S49 is isolated from *Streptococcus pyogenes* NZ131 and is a homologue of Endo S. Endo S49 has a specific endoglycosidase activity on native IgG and cleaves a larger variety of Fc glycans than Endo S.

In a preferred embodiment, the enzyme in step (i) of this embodiment is an endo-β-N-acetylglucosaminidase. In a further preferred embodiment, the endo-β-N-acetylglucosaminidase is selected from the group consisting of Endo S, Endo S49, Endo F1, Endo F2, Endo F3, Endo H, Endo M, Endo A, and any combination thereof.

When the glycan to be trimmed is a diantennary structure of the complex type, the endo-β-N-acetylglucosaminidase is preferably selected from the group consisting of Endo S, Endo S49, Endo F1, Endo F2, Endo F3, and a combination thereof.

When the oligosaccharide to be trimmed is a diantennary structure of the complex type (i.e. according to FIG. 1(c), and it is present at the IgG conserved N-glycosylation site at N297, the endo-β-N-acetylglucosaminidase is preferably selected from the group consisting of Endo S, Endo S49, Endo F, 1, Endo F2, Endo F3, and a combination thereof, more preferably from the group consisting of Endo S, Endo S49, and a combination thereof.

When the glycan to be trimmed is a diantennary structure of the complex type, and it is not present at the IgG conserved N-glycosylation site at N297, the endo-β-N-acetylglucosaminidase is preferably selected from the group consisting of Endo F1, Endo F2, Endo F3, and a combination thereof.

When the glycan to be trimmed is a high mannose, the endo-β-N-acetylglucosaminidase is preferably selected from the group consisting of Endo H, Endo M, Endo A and Endo F1.

The present invention thus also relates to a process for the preparation of a modified glycoprotein, the process comprising the steps of:
(i) trimming a glycan of a glycoprotein comprising an oligosaccharide glycan by the action of an endo-β-N-acetylglucosaminidase, in order to provide a glycoprotein comprising a glycan comprising a terminal GlcNAc-moiety according to formula (101); and
(ii) contacting said glycoprotein comprising a glycan according to formula (101) with $Su(A)_x$-P in the presence of a suitable catalyst; wherein $Su(A)_x$ is a sugar derivative Su comprising x functional groups A wherein x is 1, 2, 3 or 4 and wherein A is independently selected from the group consisting of a thiol group or a precursor thereof, a halogen, a sulfonyloxy group, a halogenated acetamido group, a mercaptoacetamido group and a sulfonated hydroxy acetamido group; wherein P is a nucleotide; wherein a suitable catalyst is defined as a galactosyltransferase or a galactosyltransferase comprising a mutant catalytic domain, wherefore $Su(A)_x$-P is a substrate; and wherein a glycan comprising a terminal GlcNAc-moiety is a glycan according to formula (101) or (102):

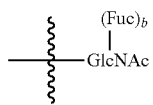
101

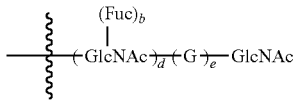
102 wherein b, d, e and G are as defined above.

Preferably, the catalyst in step(ii) is selected from the group consisting of β(1,4)-galactosyltransferases, β(1,3)-N-galactosyltransferases, β(1,4)-galactosyltransferases comprising a mutant catalytic domain and β(1,3)-N-galactosyltransferases comprising a mutant catalytic domain. Galactosyltransferases are described in more detail above.

In a further preferred embodiment, the endo-β-N-acetylglucosaminidase is selected from the group consisting of Endo S, Endo S49, Endo F1, Endo F2, Endo F3, Endo H, Endo M, Endo A, and any combination thereof more preferably, the endo-β-N-acetylglucosaminidase is selected from the group consisting of Endo S, Endo S 49, Endo F1, Endo F2, Endo F3 and any combination thereof. Most preferably, the endo-β-N-acetylglucosaminidase is Endo S or Endo S49.

The trimming step (2) of the process according to the invention is preferably performed in a suitable buffer solution, such as for example phosphate, buffered saline (e.g. phosphate-buffered saline, tris-buffered saline), citrate, HEPES, tris and glycine. Suitable buffers are known in the art. Preferably, the buffer solution is phosphate-buffered saline (PBS) or tris buffer.

The process is preferably performed at a temperature in the range of about 4 to about 50° C., more preferably in the range of about 10 to about 45° C., even more preferably in the range of about 20 to about 40° C., and most preferably in the range of about 30 to about 37° C.

The process is preferably performed a pH in the range of about 5 to about 9, preferably in the range of about 5.5 to about 8.5, more preferably in the range of about 6 to about 8. Most preferably, the process is performed at a pH in the range of about 7 to about 8.

Modified Glycoprotein

The present invention also relates to a glycoprotein, obtainable by the process for the preparation of a modified glycoprotein according to the invention.

A modified glycoprotein is defined as a glycoprotein comprising a modified glycan, said glycan comprising a GlcNAc-$Su(A)_x$ disaccharide-moiety at the non-reducing end, wherein $Su(A)_x$ is as defined above. In a preferred embodiment, the glycoprotein is an antibody.

In a preferred embodiment, the glycoprotein comprises a glycan according to formula (105) or (106):

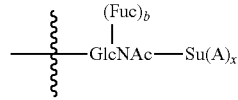
105

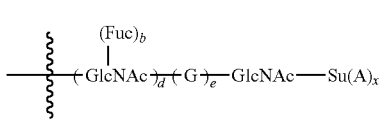
106 wherein:
b is 0 or 1;
d is 0 or 1;
e is 0 or 1;

G is a monosaccharide, or a linear or branched oligosaccharide comprising 2 to 20 sugar moieties; and
$Su(A)_x$ is a sugar derivative Su comprising x functional groups A wherein x is 1, 2, 3 or 4 and wherein A is independently selected from the group consisting of a thiol group, a halogen, a sulfonyloxy group, a halogenated acetamido group, a mercaptoacetamido group and a sulfonated hydroxyacetamido group.

As described above, when in the process for the preparation of a modified glycoprotein according the invention, functional group A is a precursor for a thiol group, said precursor is transformed into a thiol group during said process. As a consequence, when the process is performed with a sugar derivative $Su(A)_x$ comprising a precursor for a thiol group as a functional group A, a modified glycoprotein comprising a thiol group as a functional group A is obtained.

Preferably, when d is 0 then e is 1, and when e is 0 then d is 1.

G represents a monosaccharide, or a linear or branched oligosaccharide comprising 2 to 20, preferably 2 to 12, more preferably 2 to 10, even more preferably 2 to 8 and most preferably 2 to 6 sugar moieties. Sugar moieties that may be present in a glycan are known to a person skilled in the art, and include e.g. glucose (Glc), galactose (Gal), mannose (Man), fucose (Fuc), N-acetylglucosamine (GlcNAc), N-acetylgalactosamine (GalNAc), N-acetylneuraminic acid (NeuNAc) or sialic acid, or xylose (Xyl).

More preferably, the modified glycoprotein obtainable by the process described above is a glycoprotein according to formula (107) or (108):

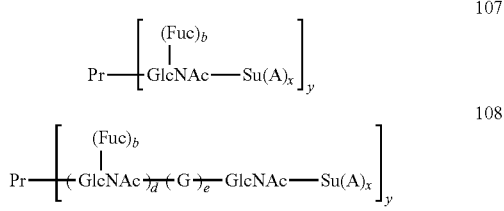

wherein:
Pr represents a protein;
y is 1 to 20; and
$Su(A)_x$, b, d, e and G are as defined above.

In a preferred embodiment y is 1 to 12, more preferably y is 1, 2, 3, 4, 5, 6, 7 or 8, and even more preferably y is 1, 2, 3 or 4. Most preferably y is 1 or 2. In yet another preferred embodiment, y is 2, 4, 6 or 8. This embodiment is particularly preferred when the glycoprotein to be modified is an antibody, i.e. when Pr is Ab.

In a preferred embodiment, C1 of the core-sugar moiety of the modified glycan, said glycan comprising a GlcNAc-$Su(A)_x$ disaccharide-moiety at the non-reducing end, is bonded to the protein via an N-glycosidic bond to a nitrogen atom in an amino acid residue in said protein, more preferably to an amide nitrogen atom in the side chain of an asparagine (Asn) or an arginine (Arg) amino acid. However, C1 of the core-sugar-moiety of said modified glycan may also be bonded to the protein via an O-glycosidic bond to an oxygen atom in an amino acid residue in said protein, more preferably to an oxygen atom in the side chain of a serine (Ser) or threonine (Thr) amino acid. In this embodiment, it is preferred that the core-sugar-moiety of said glycan is an O-GlcNAc-moiety or an O-GalNAc moiety, preferably an O-GlcNAc moiety. C1 of the core-sugar-moiety of said modified glycan may also be bonded to the protein via a C-glycosidic bond to a carbon atom on the protein, e.g. to tryptophan (Trp). As described above, a glycoprotein may comprise more than one oligosaccharide chains, and may constitute of a combination of N-linked, O-linked and C-linked glycoproteins.

Said modified glycan may be present at a native glycosylation site of a protein, but may also be introduced on a different site on a protein.

In a preferred embodiment the modified glycoprotein is a modified antibody. Said antibody (Ab) comprises a glycan comprising a GlcNAc-$Su(A)_x$ disaccharide-moiety at the non-reducing end. Such an antibody is herein also referred to as a modified antibody. A preferred modified antibody is an antibody according to formula (107) or (108) as defined above, wherein Pr is Ab. In this embodiment, it is further preferred that y is 1, 2, 3, 4, 5, 6, 7 or 8, and even more preferred that y is 1, 2, 3 or 4.

As was defined above, said antibody may be a whole antibody, but also an antibody fragment. When the antibody is a whole antibody, said antibody preferably comprises one or more, more preferably one, modified glycans on each heavy chain. Said whole antibody thus preferably comprises two or more, preferably two, four, six or eight of said glycans, more preferably two or four, and most preferably two glycans. In other words, when said antibody is a whole antibody, y is preferably 2, 4, 6 or 8, more preferably y is 2 or 4, and most preferably y is 2. When the antibody is an antibody fragment, it is preferred that y is 1, 2, 3 or 4, and more preferably y is 1 or 2.

In a preferred embodiment, said antibody is a monoclonal antibody (mAb). Preferably, said antibody is selected from the group consisting of IgA, IgD, IgE, IgG and IgM antibodies. More preferably, said antibody is an IgG antibody, and most preferably said antibody is an IgG1 antibody.

In a preferred embodiment, the glycoprotein in the modified antibody is attached to the conserved N-glycosylation site in the Fc-fragment at asparagine in the region 290-305, typically N297. As described above, said modified glycan may be present at a native glycosylation site of a protein, in this case an antibody, but may also be present on a different site. FIG. 13 shows different glycoforms of a monoclonal antibody, e.g.

IgG. The modified glycan may be on any position in the heavy or light chain.

The sugar derivative $Su(A)_x$ and preferred embodiments thereof are described in detail above. The definitions of the groups A and preferred embodiments thereof, and preferred embodiments of the process for the preparation of a modified glycoprotein also hold for the modified glycoprotein obtainable by said process. Thus, in a preferred embodiment, x is 1 or 2, more preferably x is 1. In another preferred embodiment, functional group A is a thiol group, a halogen, or a halogenated acetamido group, more preferably a halogen.

Further examples of $Su(A)_x$ present in a modified glycoprotein and in a modified antibody according to the invention include 6-A-6-deoxygalactose (6-A-Gal), such as 6-chloro-6-deoxygalactose (6-ClGal), 6-thio-6-deoxygalactose (6-HSGal) or 2-A-2-deoxygalactose (2-A-Gal), such as 2-chloro-2-deoxygalactose (2-ClGal), 2-thio-2-deoxygalactose (2-HSGal). Alternatively, A may be indirectly substituted to the sugar derivative as part of an acetamido group that in turn is substituting a hydroxyl group. Examples include 6-A-acetamido-6-deoxygalactose (6-GalNAcA), such as 6-chloroacetamido-6-deoxygalactose (6-GalNAcCl), 6-thioacetamido-6-deoxygalactose (6-GalNAcSH)

or 2-A-acetamido-2-deoxygalactose (2-GalNAcA), such as 2-chloroacetamido-2-deoxygalactose (2-GalNAcCl), 2-thioacetamido-2-deoxygalactose (2-GalNAcSH). Alternatively, A may be indirectly substituted to the sugar derivative as part of another functional group that in turn is substituting a hydroxyl group or is attached to a hydroxyl group. Examples of such other functional group include an (hetero)alkyl chain or a (hetero)aryl chain.

In a preferred embodiment, $Su(A)_x$ is selected from the group consisting of 6-GalNAcCl, 6-GALNAcSH, 2-GalNAcCl and 2-GalNAcSH.

In a preferred embodiment, $Su(A)_x$ comprises 1 or 2 functional groups A, i.e. preferably x is 1 or 2. More preferably, x is 1. In another preferred embodiment, Su is galactose (Gal). In a further preferred embodiment, x is 1 or 2 and Su is Gal, and most preferably, x is 1 and Su is Gal.

In a preferred embodiment, $Su(A)_x$ is selected from the group consisting of 6-GalNAcCl, 6-GalNAcSH, 2-GalNAcCl, 2-GalNAcSH, 6-ClGal, 2-ClGal, 2-HSGal and 6-HSGal, more preferably form the group consisting of 6-GalNAcCl, 6-GalNAcSH, 2-GalNAcCl, 2-GalNAcSH, 6-ClGal- and 2-ClGal.

In a further preferred embodiment, x is 1 and $Su(A)_x$ is selected from the group consisting of 6-GalNAcCl, 6-GalNAcSH, 2-GalNAcCl, 2-GalNAcSH, 6-ClGal, 2-ClGal, 2-HSGal and 6-HSGal, more preferably from the group consisting of 6-GalNAcCl, 6-GalNAcSH, 2-GalNAcCl, 2-GalNAcSH, 6-ClGal- and 2-ClGal.

In a preferred embodiment of the modified glycoprotein according to the invention, A is a thiol group or a halogen. The modified glycoprotein is preferably a thiol-modified glycoprotein or a halogen-modified glycoprotein. When the glycoprotein is a halogen-modified glycoprotein, it is preferably a chloride-modified glycoprotein, a bromide-modified glycoprotein or an iodide-modified glycoprotein, more preferably a chloride-modified glycoprotein or a bromide-modified glycoprotein, and most preferably a chloride-modified glycoprotein. More preferably, x is 1 and the modified glycoprotein is preferably a thiol-modified glycoprotein or a halogen-modified glycoprotein (preferably a chloride- or a bromide-modified glycoprotein, most preferably a chloride-modified glycoprotein).

In a particularly preferred embodiment of the modified glycoprotein according to the invention, $Su(A)_x$ is selected from the group consisting of 2-GalNAcSH, 2-GalNAcX, 2-GalNAcOS(O)$_2$R$^8$, 6-GalNAcSH, 6-GalNAcX and 6-GalNAcOS(O)$_2$R$^8$. In an even more preferred embodiment, x is 1 or 2 and $Su(A)_x$ is selected from the group consisting of 2-GalNAcSH, 2-GalNAcX, 2-GalNAcOS(O)$_2$R$^8$, 6-GalNAcSH, 6-GalNAcX and 6-GalNAcOS(O)$_2$R$^8$. In a most preferred embodiment, x is 1 and $Su(A)_x$ is selected from the group consisting of 2-GalNAcSH, 2-GalNAcX, 2-GalNAcOS(O)$_2$R$^8$, 6-GalNAcSH, 6-GalNAcX and 6-GalNAcOS(O)$_2$R$^8$. R$^8$, and preferred embodiments of R$^8$, are as defined above.

When the modified glycoprotein according to the invention comprises a thiol group, said modified glycoprotein may be referred to as a thiol-modified glycoprotein. When a modified glycoprotein comprises a halogen, said glycoprotein may be referred to as a halogen-modified glycoprotein. When a modified glycoprotein comprises a sulfonyloxy group, said glycoprotein may be referred to as a sulfonyloxy-modified glycoprotein. When a modified glycoprotein comprises a mercaptoacetamido group, said glycoprotein may be referred to as a mercaptoacetamido-modified glycoprotein. When a modified glycoprotein comprises a halogenated acetamido group, said glycoprotein may be referred to as a halogenated acetamido-modified glycoprotein. When a modified glycoprotein comprises a sulfonated hydroxyacetamido group, said glycoprotein may be referred to as a sulfonated hydroxyacetamido-modified glycoprotein.

The invention also relates to the use of a modified glycoprotein according to the invention in the preparation of a glycoprotein-conjugate, wherein a glycoprotein-conjugate is defined as a glycoprotein that is conjugated to a molecule of interest D via a linker L.

Process for the Preparation of a Glycoprotein-Conjugate

The present invention also relates to the use of a modified glycoprotein according to the invention in the preparation of a protein-conjugate. A protein-conjugate is herein defined as a protein that is conjugated to a molecule of interest (D) via a linker (L). The protein-conjugate according to the invention may be conjugated to one or to more than one molecule of interest (D) via a linker (L).

The invention also relates to the use of a modified antibody according to the invention in the preparation of an antibody-conjugate, wherein an antibody-conjugate is defined as an antibody that is conjugated to a molecule of interest (D) via a linker (L).

A molecule of interest may for example be a reporter molecule, a diagnostic molecule, an active substance, an enzyme, an amino acid (including an unnatural amino acid), a (non-catalytic) protein, a peptide, a polypeptide, an oligonucleotide, a glycan, a (poly)ethylene glycol diamine (e.g. 1,8-diamino-3,6-dioxaoctane or equivalents comprising longer ethylene glycol chains), a polyethylene glycol chain, a polyethylene oxide chain, a polypropylene glycol chain, a polypropylene oxide chain, 1,x-diaminoalkane (wherein x is the number of carbon atoms in the alkane), an azide or a (hetero)cycloalkynyl moiety, preferably a bivalent or bifunctional (hetero)cycloalkynyl moiety. In a preferred embodiment, the molecule of interest is selected from the group consisting of an amino acid (in particular lysine), an active substance, a reporter molecule, an azide and a (hetero)cycloalkynyl moiety.

An active substance is a pharmacological and/or biological substance, i.e. a substance that is biologically and/or pharmaceutically active, for example a drug or a prodrug, a diagnostic agent, an amino acid, a protein, a peptide, a polypeptide, a glycan, a lipid, a vitamin, a steroid, a nucleotide, a nucleoside, a polynucleotide, RNA or DNA. Examples of suitable peptide tags include cell-penetrating peptides like human lactoferrin or polyarginine. An example of a suitable glycan is oligomannose.

In a preferred embodiment, the active substance is selected from the group consisting of drugs and prodrugs. More preferably, the active substance is selected from the group consisting of pharmaceutically active compounds, in particular low to medium molecular weight compounds (e.g. about 200 to about 1500 Da, preferably about 300 to about 1000 Da), such as for example cytotoxins, antiviral agents, antibacterial agents, peptides and oligonucleotides. Examples of cytotoxins include camptothecins, doxorubicin, daunorubicin, taxanes, calicheamycins, duocarmycins, maytansines, auristatins and pyrrolobenzodiazepines (PBDs). Preferably, the cytotoxin is selected from the group consisting of colchicine, vinca alkaloids, camptothecins, doxorubicin, daunorubicin, taxanes, calicheamycins, tubulysins, irinotecans, an inhibitory peptide, amanitin, deBouganin, duocarmycins, maytansines, auristatins and pyrrolobenzodiazepines (PBDs). In a preferred embodiment, the cytotoxin is selected from the group consisting of camptothecins, doxorubicin, daunorubicin, taxanes, calicheamycins, duocarmycins, maytansines, auristatins and pyrrolobenzodiazepines (PBDs). In another preferred embodiment, the cytotoxin is selected from the group consisting of colchicine, vinca alkaloids, tubulysins, irinotecans, an inhibitory peptide, amanitin and deBouganin.

A reporter molecule is a molecule whose presence is readily detected, for example a diagnostic agent, a dye, a fluorophore, a radioactive isotope label, a contrast agent, a magnetic resonance imaging agent or a mass label. Examples of a fluorophore include all kinds of Alexa Fluor (e.g. Alexa Fluor 555), cyanine dyes (e.g. Cy3 or Cy5), coumarin derivatives, fluorescein, rhodamine, allophycocyanin and chromomycin.

Examples of radioactive isotope label include $^{99m}$Tc, $^{111}$In, $^{18}$F, $^{14}$C, $^{64}$Cu, $^{131}$I or $^{123}$I, which may or may not be connected via a chelating moiety such as DTPA, DOTA, NOTA or HYNIC.

In the protein-conjugate according to the invention, the molecule of interest (D) is conjugated to the antibody via a linker (L). Linkers or linking units are well known in the art, and are described in more detail below. A linker-conjugate is herein defined as a linker (L) that is conjugated to a molecule of interest (D). The linker-conjugate according to the invention may comprise one or more than one molecule of interest (D). The linker-conjugate preferably is of the formula B-L (D)$_r$, wherein D is as defined above, and B and L are as defined below, and r is 1 to 20. Preferably r is 1 to 10, more preferably r is 1 to 8, even more preferably r is 1, 2, 3, 4, 5 or 6, even more preferably r is 1, 2, 3 or 4, even more preferably r is 1 or 2 and most preferably r is 1.

The invention also relates to a process for the preparation of a glycoprotein-conjugate, said process comprising reacting a modified glycoprotein according to the invention with a linker-conjugate, wherein said linker-conjugate comprises a functional group B and one or more molecules of interest, wherein said functional group B is a functional group that is capable of reacting with a functional group A on a glycan of the modified glycoprotein, and wherein functional group A is as defined above.

The invention relates to a process for the preparation of a glycoprotein-conjugate, the process comprising the steps of:
(a) contacting a glycoprotein comprising a glycan comprising a terminal GlcNAc-moiety with Su(A)$_x$-P in the presence of a suitable catalyst; wherein Su(A)$_x$ is a sugar derivative Su comprising x functional groups A wherein x is 1, 2, 3 or 4 and wherein A is independently selected from the group consisting of a thiol group or a precursor thereof, a halogen, a sulfonyloxy group, a halogenated acetamido group, a mercaptoacetamido group and a sulfonated hydroxyacetamido group; wherein P is a nucleotide; wherein a suitable catalyst is defined as a galactosyltransferase or a galactosyltransferase comprising a mutant catalytic domain, wherefore Su(A)$_x$-P is a substrate; and wherein a glycan comprising a terminal GlcNAc-moiety is a glycan according to formula (101) or (102):

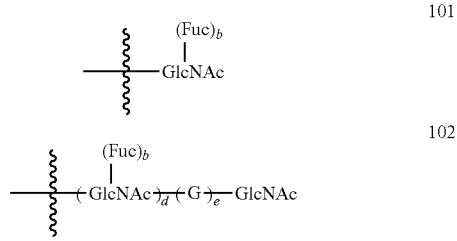

wherein:
b is 0 or 1;
d is 0 or 1;
e is 0 or 1; and
G is a monosaccharide, or a linear or branched oligosaccharide comprising 2 to 20 sugar moieties;
to obtain a modified glycoprotein; and
(b) reacting the modified glycoprotein with a linker-conjugate, wherein said linker-conjugate comprises a functional group B and one or more molecules of interest (D), wherein said functional group B is a functional group that is capable of reacting with a functional group A on a glycan of the modified glycoprotein, and wherein functional group A is independently selected from the group consisting of a thiol group, a halogen, a sulfonyloxy group, a halogenated acetamido group, a mercaptoacetamido group and a sulfonated hydroxyacetamido group.

In a preferred embodiment of the process for the preparation of an glycoprotein-conjugate, Su(A)$_x$ comprises 1 or 2 functional groups A, i.e. preferably x is 1 or 2. More preferably, x is 1. In another preferred embodiment, Su is galactose (Gal). In a further preferred embodiment, x is 1 or 2 and Su is Gal, and most preferably, x is 1 and Su is Gal. In these preferred embodiments it is further preferred that the linker-conjugate comprises 1 or 2, and most preferably 1, molecules of interest.

In a preferred embodiment, Su(A)$_x$ is selected from the group consisting of 6-GalNAcCl, 6-GalNAcSH, 2-GalNAcCl, 2-GalNAcSH, 6-ClGal, 2-ClGal, 2-HSGal and 6-HSGal, more preferably form the group consisting of 6-GalNAcCl, 6-GalNAcSH, 2-GalNAcCl, 2-GalNAcSH, 6-ClGal- and 2-ClGal. In these preferred embodiments it is further preferred that the linker-conjugate comprises 1 or 2, and most preferably 1, molecules of interest.

In a further preferred embodiment, x is 1 and Su(A)$_x$ is selected from the group consisting of 6-GalNAcCl, 6-GalNAcSH, 2-GalNAcCl, 2-GalNAcSH, 6-ClGal, 2-ClGal, 2-HSGal and 6-HSGal, more preferably from the group consisting of 6-GalNAcCl, 6-GalNAcSH, 2-GalNAcCl, 2-GalNAcSH, 6-ClGal- and 2-ClGal. In these preferred embodiments it is further preferred that the linker-conjugate comprises 1 or 2, and most preferably 1, molecules of interest.

In a particularly preferred embodiment of the modified antibody according to the invention, Su(A)$_x$ is selected from the group consisting of 2-GalNAcSH, 2-GalNAcX, 2-GalNAcOS(O)$_2$R$^8$, 6-GalNAcSH, 6-GalNAcX and 6-GalNAcOS(O)$_2$R$^8$. In an even more preferred embodiment, x is 1 or 2 and Su(A)$_x$ is selected from the group consisting of 2-GalNAcSH, 2-GalNAcX, 2-GalNAcOS(O)$_2$R$^8$, 6-GalNAcSH, 6-GalNAcX and 6-GalNAcOS(O)$_2$R$^8$. In a most preferred embodiment, x is 1 and Su(A)$_x$ is selected from the group consisting of 2-GalNAcSH, 2-GalNAcX, 2-GalNAcOS(O)$_2$R$^8$, 6-GalNAcSH, 6-GalNAcX and 6-GalNAcOS(O)$_2$R$^8$. In these preferred embodiments it is further preferred that the linker-conjugate comprises 1 or 2, and most preferably 1, molecules of interest. X and R$^8$, and preferred embodiments thereof, are as defined above. Preferably X is Cl.

The invention further relates to a process for the preparation of a glycoprotein-conjugate, said process comprising reacting a modified glycoprotein according to the invention with a linker-conjugate, wherein said linker-conjugate comprises a functional group B and one or more molecules of interest, wherein said functional group B is a functional group that is capable of reacting with a functional group A on a glycan of the modified glycoprotein, and wherein functional group A is independently selected from the group consisting of a thiol group, a halogen, a sulfonyloxy group, a halogenated acetamido group, a mercaptoacetamido group and a sulfonated hydroxyacetamido group.

A suitable linker-conjugate for the preparation of a protein-conjugate according to the invention is a linker-conjugate comprising a functional group B and a molecule of interest. Linkers (L), also referred to as linking units, are well known in the art. In a linker-conjugate as described herein, L is linked to a molecule of interest (D) as well as to a functional group (B), as was described above. Numerous methods for linking said functional group (B) and said molecule of interest (D) to L are known in the art. As will be clear to a person skilled in the art, the choice of a suitable method for linking a functional group (B) to one end and a molecule of interest (D) to another end of a linker depends on the exact nature of the functional group (B), the linker (L) and the molecule of interest (D).

A linker may have the general structure $F^1$-L($F^2$)$_r$, wherein $F^1$ represents either a functional group B or a functional group that is able to react with a functional group F on the functional group B as described above, e.g. a (hetero)cycloalkynyl group, a terminal alkynyl group, a primary amine, an aminooxy group, a hydrazyl group, an azido group, an N-maleimidyl group, an acetamido group or a thiol group. $F^2$ represents a functional group that is able to react with a functional group F on the molecule of interest. Since more than one molecule of interest may be bonded to a linker, more than one functional group $F^2$ may be present on L. As was described above, r is 1 to 20, preferably 1 to 10, more preferably 1 to 8, even more preferably 1, 2, 3, 4, 5 or 6, even more preferably 1, 2, 3 or 4 and most preferably, r is 1 or 2.

L may for example be selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups, $C_9$-$C_{200}$ arylalkynylene groups. Optionally the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups may be substituted, and optionally said groups may be interrupted by one or more heteroatoms, preferably 1 to 100 heteroatoms, said heteroatoms preferably being selected from the group consisting of O, S and $NR^5$, wherein $R^5$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups. Most preferably, the heteroatom is O.

F, $F^1$ and $F^2$ may for example be independently selected from the group consisting of hydrogen, halogen, $R^5$, $C_4$-$C_{10}$ (hetero)cycloalkyne groups, —CH=C($R^5$)$_2$, —C≡C$R^5$, —[C($R^5$)$_2$C($R^5$)$_2$O]$_q$—$R^5$, wherein q is in the range of 1 to 200, —CN, —N$_3$, —NCX, —XCN, —X$R^5$, —N($R^5$)$_2$, —$^+$N($R^5$)$_3$, —C(X)N($R^5$)$_2$, —C($R^5$)$_2$X$R^5$, —C(X)$R^5$, —C(X)X$R^5$, —S(O)$R^5$, —S(O)$_2$$R^5$, —S(O)O$R^5$, —S(O)$_2$O$R^5$, —S(O)N($R^5$)$_2$, —S(O)$_2$N($R^5$)$_2$, —OS(O)$R^5$, —OS(O)$_2$$R^5$, —OS(O)O$R^5$, —OS(O)$_2$O$R^5$, -P(O)($R^5$)(O$R^5$), -P(O)(O$R^5$)$_2$, —OP(O)(O$R^5$)$_2$, —Si($R^5$)$_3$, —XC(X)$R^5$, —XC(X)X$R^5$, —XC(X)N($R^5$)$_2$, —N($R^5$)C(X)$R^5$, —N($R^5$)C(X)X$R^5$ and —N($R^5$)C(X)N($R^5$)$_2$, wherein X is oxygen or sulphur and wherein $R^5$ is as defined above.

Examples of suitable linking units include (poly)ethylene glycol diamines (e.g. 1,8-diamino-3,6-dioxaoctane or equivalents comprising longer ethylene glycol chains), polyethylene glycol or polyethylene oxide chains, polypropylene glycol or polypropylene oxide chains and 1,x-diaminoalkanes wherein x is the number of carbon atoms in the alkane.

Another class of suitable linkers comprises cleavable linkers. Cleavable linkers are well known in the art. For example Shabat et al., Soft Matter 2012, 6, 1073, incorporated by reference herein, discloses cleavable linkers comprising self-immolative moieties that are released upon a biological trigger, e.g. an enzymatic cleavage or an oxidation event. Some examples of suitable cleavable linkers are peptide-linkers that are cleaved upon specific recognition by a protease, e.g. cathepsin, plasmin or metalloproteases, or glycoside-based linkers that are cleaved upon specific recognition by a glycosidase, e.g. glucoronidase, or nitroaromatics that are reduced in oxygen-poor, hypoxic areas.

When A is a thiol group, linking of the thiol-modified glycoprotein with the linker-conjugate preferably takes place via a Michael-type addition reaction or a nucleophilic substitution reaction or a thiol-ene reaction. Functional group B is then preferably an N-maleimidyl group for the Michael-type addition, a halogenated acetamido group for the nucleophilic substitution reaction, or a terminal alkene for the thiol-ene reaction. The linker-conjugate is then preferably X—CH$_2$C(O)NHL(D)$_r$ or X—CH$_2$C(O)N[L(D)$_r$]$_2$ wherein X is F, Cl, Br or I, or a maleimide-linker-conjugate (120) as illustrated below.

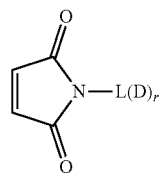

When A is a halogen-modified glycoprotein, a halogenated acetamide-modified glycoprotein, a sulfonyloxy-modified glycoprotein or a sulfonated hydroxy acetamide-modified glycoprotein, linking of the modified glycoprotein with the linker-conjugate preferably takes place via reaction with a thiol to form a thioether. When A is a halogen, a halogenated acetamido group, a sulfonyloxy group or a sulfonated hydroxy acetamido group, linking of the modified glycoprotein with the linker-conjugate preferably takes place via reaction with a thiol to form a thioether. In other words, when the modified glycoprotein is a halogen-modified glycoprotein, a halogenated acetamido-modified glycoprotein, a sulfonyloxy-modified glycoprotein or a sulfonated hydroxy acetamide-modified glycoprotein, linking of the modified glycoprotein with the linker-conjugate preferably takes place via reaction with a thiol to form a thioether.

Functional group B comprises then preferably a thiol group, and a preferred linker-conjugate is HS-L(D)$_r$. However, functional group B may also comprise an alcohol group or an amine group.

In particular, the invention relates to a process for the preparation of a glycoprotein-conjugate, wherein:
(a) when said modified glycoprotein is a halogen-modified glycoprotein or a halogenated acetamido-modified glycoprotein, functional group B comprises a thiol group, an alcohol group or an amine group; or (b) when said modified glycoprotein is a thiol-modified glycoprotein or a mercaptoacetamido-modified glycoprotein, functional group B comprises an N-maleimide group or a halogenated acetamido group or an alkene; or (c) when said modified glycoprotein is a sulfonyloxy-modified glycoprotein or a sulfonated hydroxyacetamido-modified glycoprotein, functional group B comprises thiol group, an alcohol group or an amine group.

When said modified glycoprotein is a halogen-modified glycoprotein and functional group B comprises a thiol group, said thiol group may be an aliphatic or an aromatic thiol group. In a preferred embodiment said thiol group is an aromatic thiol group.

In a preferred embodiment, the modified glycoprotein is a thiol-modified glycoprotein and functional group B comprises an N-maleimide group or a halogenated acetamido group.

In another preferred embodiment, the modified glycoprotein is a thiol-modified glycoprotein and functional group B comprises an allenamide group. The invention therefore also relates to a process for the preparation of a glycoprotein-conjugate, wherein said modified glycoprotein is a thiol-modified glycoprotein and functional group B comprises an allenamide group.

The present invention further relates to the use of the glycoprotein according to the invention in the preparation of a glycoprotein-conjugate, wherein a glycoprotein-conjugate is defined as a glycoprotein that is conjugated to a molecule of interest D via a linker L.

Glycoprotein-Conjugate

The invention also relates to a glycoprotein-conjugate obtainable by the process for the preparation of a glycoprotein-conjugate according to the invention.

In a preferred embodiment, the glycoprotein-conjugate according to the invention is an antibody-conjugate.

In another preferred embodiment, the molecule of interest D is selected from the group consisting of a reporter molecule, an active substance, an enzyme, an amino acid, a protein, a peptide, a polypeptide, an oligonucleotide, a glycan, a (poly)ethylene glycol diamine, a polyethylene glycol chain, a polyethylene oxide chain, a polypropylene glycol chain, a polypropylene oxide chain and 1,x-diaminoalkane, wherein x is the number of carbon atoms in the alkane and x is 1-200, an azide or a (hetero)cycloalkynyl moiety, preferably a bivalent or bifunctional (hetero)cycloalkynyl moiety.

In particular, the invention relates to a glycoprotein-conjugate obtainable by a process comprising the steps of:
(a) contacting a glycoprotein comprising a glycan comprising a terminal GlcNAc-moiety with $Su(A)_x$-P in the presence of a suitable catalyst; wherein $Su(A)_x$ is a sugar derivative Su comprising x functional groups A wherein x is 1, 2, 3 or 4 and wherein A is independently selected from the group consisting of a thiol group or a precursor thereof, a halogen, a sulfonyloxy group, a halogenated acetamido group, a mercaptoacetamido group and a sulfonated hydroxyacetamido group; wherein P is a nucleotide; wherein a suitable catalyst is defined as a galactosyltransferase or a galactosyltransferase comprising a mutant catalytic domain, wherefore $Su(A)_x$-P is a substrate; and wherein a glycan comprising a terminal GlcNAc-moiety is a glycan according to formula (101) or (102):

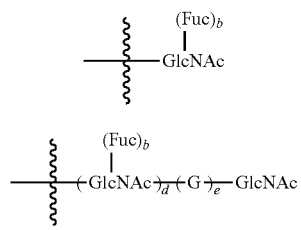

wherein:
b is 0 or 1;
d is 0 or 1;
e is 0 or 1; and
G is a monosaccharide, or a linear or branched oligosaccharide comprising 2 to 20 sugar moieties;

to obtain a modified glycoprotein; and
(b) reacting the modified glycoprotein with a linker-conjugate, wherein said linker-conjugate comprises a functional group B and one or more molecules of interest (D), wherein said functional group B is a functional group that is capable of reacting with a functional group A on a glycan of the modified glycoprotein, and wherein functional group A is independently selected from the group consisting of a thiol group, a halogen, a sulfonyloxy group, a halogenated acetamido group, a mercaptoacetamido group and a sulfonated hydroxyacetamido group.

The processes of step (a) and (b) as well as their preferred embodiments are described in detail above.

When a thiol-modified glycoprotein is reacted with a linker-conjugate comprising a functional group B that comprises an N-maleimide group, preferably the glycoprotein-conjugate according to the invention is according to formula (121) or (122):

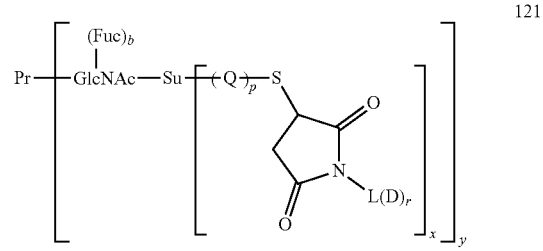

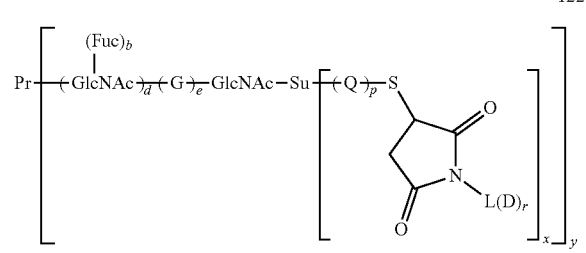

wherein:
Pr represents a protein;
L is a Linker;
D is a molecule of interest;
r is 1 to 20;
x is 1, 2, 3 or 4;

y is 1 to 20; and
b is 0 or 1;
d is 0 or 1;
e is 0 or 1;
p is 0 or 1;
Q is —N(H)C(O)CH$_2$— or CH$_2$;
Su is a sugar or sugar derivative; and
G is a monosaccharide, or a linear or branched oligosaccharide comprising 2 to 20 sugar moieties.

The value of p and the nature of Q depend on the nature of the modified sugar or sugar derivative Su(A)$_x$ that is used for the preparation of the glycoprotein-conjugate according to the process of the invention. If in Su(A)$_x$ a thiol group is present on the C2, C3, or C4 position of the sugar or the sugar derivative (instead of a sugar OH-group), then p is 0. If the Su(A)$_x$ is a 2-(mercaptoacetamido)-2-deoxy sugar derivative (i.e. a mercaptoacetamido group is present on C2 of said sugar or sugar derivative), Su(A)$_x$ is e.g. GalNAcSH or GlcNAcSH, then p is 1 and Q is —N(H)C(O)CH$_2$—. If the thiol in Su(A)$_x$ is present on the C6 position of the sugar or the sugar derivative, then p is 1 and Q is —CH$_2$—.

When a thiol-modified glycoprotein is reacted with a linker-conjugate comprising a functional group B that comprises a halogenated acetamido group, preferably the glycoprotein-conjugate according to the invention is according to formula (123) or (124):

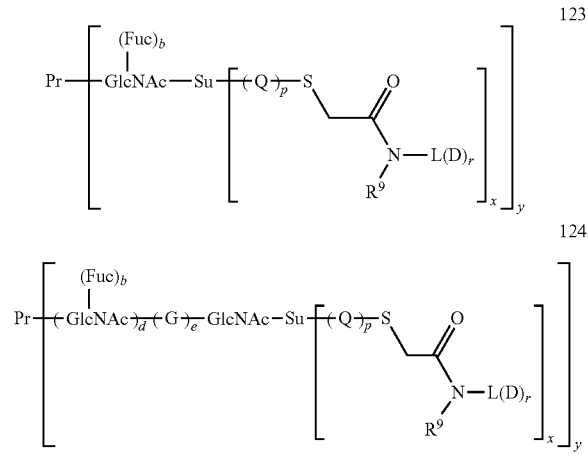

wherein Pr, L, D, r, x, y, b, d, e, p, Q, Su and G are as defined above for (121) and (122), and R$^9$ is selected from the group consisting of L(D)$_r$, hydrogen, C$_1$-C$_{24}$ alkyl groups, C$_6$-C$_{24}$ aryl groups C$_7$-C$_{24}$ alkylaryl groups and C$_7$-C$_{24}$ arylalkyl groups, the C$_1$-C$_{24}$ alkyl groups, C$_6$-C$_{24}$ aryl groups C$_7$-C$_{24}$ alkylaryl groups and C$_7$-C$_{24}$ arylalkyl groups optionally being substituted. Preferably, R$^9$ is selected from the group consisting of L(D)$_r$, hydrogen, C$_1$-C$_{12}$ alkyl groups, C$_6$-C$_{12}$ aryl groups C$_7$-C$_{12}$ alkylaryl groups and C$_7$-C$_{122}$ arylalkyl groups, the C$_1$-C$_{12}$ alkyl groups, C$_6$-C$_{12}$ aryl groups C$_7$-C$_{12}$ alkylaryl groups and C$_7$-C$_{12}$ arylalkyl groups optionally being substituted. More preferably, R$^9$ is selected from the group consisting of L(D)$_r$, hydrogen, C$_1$-C$_6$ alkyl groups, C$_6$-C$_{12}$ aryl groups C$_7$-C$_{12}$ alkylaryl groups and C$_7$-C$_{12}$ arylalkyl groups, the C$_1$-C$_6$ alkyl groups, C$_6$-C$_{12}$ aryl groups C$_7$-C$_{12}$ alkylaryl groups and C$_7$-C$_{12}$ arylalkyl groups optionally being substituted. Even more preferably, R$^9$ is H, C$_1$, C$_2$, C$_4$ or C$_4$ alkyl or C$_6$-C$_{12}$ aryl. Most preferably, R$^9$ is H or methyl.

Also in this embodiment the value of p and the nature of Q depend on the nature of the modified sugar or sugar derivative Su(A)$_x$ that is used for the preparation of the glycoprotein-conjugate according to the process of the invention. If in Su(A)$_x$ a halogen is present on the C2, C3, or C4 position of the sugar or the sugar derivative (instead of a sugar OH-group), then p is 0. If the Su(A)$_x$ is a 2-(chloroacetamido)-2-deoxy sugar derivative (i.e. a halogenated acetamido group is present on C2 of said sugar or sugar derivative), Su(A)$_x$ is e.g. GalNAcCl or GlcNAcCl, then p is 1 and Q is —N(H)C(O)CH$_2$—. If the halogen in Su(A)$_x$ is present on the C6 position of the sugar or the sugar derivative, then p is 1 and Q is —CH$_2$—.

When a thiol-modified glycoprotein is reacted with a linker-conjugate comprising a functional group B that comprises an allenamide group, preferably the glycoprotein-conjugate according to the invention is according to formula (125) or (126):

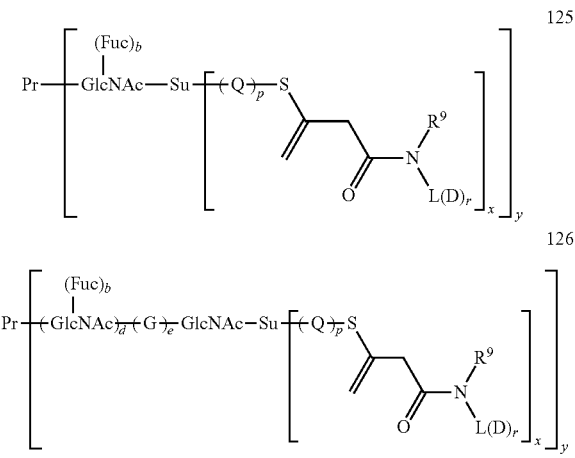

wherein Pr, L, D, r, x, y, b, d, e, p, Q, Su, G and R$^9$ are as defined above.

Also in (125) and (126), the value of p and the nature of Q depend on the nature of the modified sugar or sugar derivative Su(A)$_x$ that is used for the preparation of the glycoprotein-conjugate according to the process of the invention. If in Su(A)$_x$ a thiol group is present on the C2, C3, or C4 position of the sugar or the sugar derivative (instead of a sugar OH-group), then p is 0. If the Su(A)$_x$ is a 2-(mercaptoacetamido)-2-deoxy sugar derivative (i.e. a mercaptoacetamido group is present on C2 of said sugar or sugar derivative instead of an OH-group), Su(A)$_x$ is e.g. GalNAcSH or GlcNAcSH, then p is 1 and Q is —N(H)C(O)CH$_2$—. If the thiol in Su(A)$_x$ is present on the C6 position of the sugar or the sugar derivative, then p is 1 and Q is —CH$_2$—.

When G is a linear or branched oligosaccharide, it is preferred that G comprises 2 to 12, more preferably 2 to 10, even more preferably 2 to 8 and most preferably 2 to 6 sugar moieties. In another preferred embodiment, y is 1 to 12, more preferably y is 1, 2, 3, 4, 5, 6, 7 or 8, and even more preferably y is 1, 2, 3 or 4. Most preferably y is 1 or 2. In yet another preferred embodiment, y is 2, 4, 6 or 8. This embodiment is particularly preferred when the glycoprotein to be modified is an antibody, i.e. when Pr is Ab.

Preferably, r is 1 to 10, more preferably 1, 2, 3, 4, 5, 6, 7, or 8, even more preferably 1, 2, 3 or 4, even more preferably 1 or 2, and most preferably r is 1.

In a preferred embodiment y is 1 to 12, more preferably y is 1, 2, 3, 4, 5, 6, 7 or 8, and even more preferably y is 1, 2, 3 or 4. Most preferably y is 1 or 2. In yet another preferred embodiment, y is 2, 4, 6 or 8. This embodiment is particularly preferred when the glycoprotein to be modified is an antibody, i.e. when Pr is Ab.

In a preferred embodiment, C1 of the core-sugar moiety of the glycoprotein-glycan, is bonded to the protein via an N-glycosidic bond to a nitrogen atom in an amino acid residue in said protein, more preferably to an amide nitrogen atom in the side chain of an asparagine (Asn) or an arginine (Arg) amino acid. However, C1 of the core-sugar-moiety of said glycan may also be bonded to the protein via an O-glycosidic bond to an oxygen atom in an amino acid residue in said protein, more preferably to an oxygen atom in the side chain of a serine (Ser) or threonine (Thr) amino acid. In this embodiment, it is preferred that the core-sugar-moiety of said glycan is an O-GlcNAc-moiety or an O-GalNAc moiety, preferably an O-GlcNAc moiety. C1 of the core-sugar-moiety of said glycan may also be bonded to the protein via a C-glycosidic bond to a carbon atom on the protein, e.g. to tryptophan (Trp). As described above, a glycoprotein may comprise more than one oligosaccharide chains, and may constitute of a combination of N-linked, O-linked and C-linked glycoproteins.

Said modified glycan may be present at a native glycosylation site of a protein, but may also be introduced on a different site on a protein.

In a preferred embodiment the glycoprotein-conjugate is an antibody-conjugate, said antibody comprising a glycan comprising a GlcNAc-Su(A)$_x$ disaccharide-moiety at the non-reducing end. Such an antibody is herein also referred to as a modified antibody. A preferred modified antibody is an antibody according to formula (107) or (108) as defined above, wherein Pr is Ab. In this embodiment, it is further preferred that y is 1, 2, 3, 4, 5, 6, 7 or 8, and even more preferred that y is 1, 2, 3 or 4.

As was defined above, said antibody may be a whole antibody, but also an antibody fragment. When the antibody is a whole antibody, said antibody preferably comprises one or more, more preferably one, modified glycans on each heavy chain. Said whole antibody thus preferably comprises two or more, preferably two, four, six or eight of said glycans, more preferably two or four, and most preferably two glycans. In other words, when said antibody is a whole antibody, y is preferably 2, 4, 6 or 8, more preferably y is 2 or 4, and most preferably y is 2. When the antibody is an antibody fragment, it is preferred that y is 1, 2, 3 or 4, and more preferably y is 1 or 2.

In a preferred embodiment, said antibody is a monoclonal antibody (mAb). Preferably, said antibody is selected from the group consisting of IgA, IgD, IgE, IgG and IgM antibodies. More preferably, said antibody is an IgG antibody, and most preferably said antibody is an IgG1 antibody.

In a preferred embodiment, the glycoprotein in the modified antibody is attached to the conserved N-glycosylation site in the Fc-fragment at asparagine in the region 290-305, typically N297.

The sugar derivative Su(A)$_x$ and preferred embodiments thereof are described in detail above. The preferred embodiments of the process for the preparation of a modified glycoprotein also hold for the modified glycoprotein obtainable by said process. Thus, in a preferred embodiment, x is 1 or 2, more preferably x is 1. In another preferred embodiment, functional group A is a thiol group, a halogen, or a halogenated acetamido group, more preferably a halogen.

Further examples of Su(A)$_x$ present in a modified antibody according to the invention include 6-A-6-deoxygalactose (6-A-Gal), such as 6-chloro-6-deoxygalactose (6-Cl-Gal), 6-thio-6-deoxygalactose (6-HSGal) or 2-A-2-deoxygalactose (2-A-Gal), such as 2-chloro-2-deoxygalactose (2-ClGal), 2-thio-2-deoxygalactose (2-HSGal). Alternatively, A may be indirectly substituted to the sugar derivative as part of an acetamido group that in turn is substituting a hydroxyl group. Examples include 6-A-acetamido-6-deoxygalactose (6-GalNAcA), such as 6-chloroacetamido-6-deoxygalactose (6-GalNAcCl), 6-thioacetamido-6-deoxygalactose (6-GalNAcSH) or 2-A-acetamido-2-deoxygalactose (2-GalNAcA), such as 2-chloroacetamido-2-deoxygalactose (2-GalNAcCl), 2-thioacetamido-2-deoxygalactose (2-GalNAcSH). Alternatively, A may be indirectly substituted to the sugar derivative as part of another functional group that in turn is substituting a hydroxyl group or is attached to a hydroxyl group. Examples of such other functional group include an (hetero)alkyl chain or a (hetero)aryl chain.

In a preferred embodiment of the glycoprotein-conjugate according to the invention, y is 1, 2, 3 or 4 (preferably 2 or 4) and/or x is 1 or 2 (preferably 1).

In a preferred embodiment y is 1 to 12, more preferably y is 1, 2, 3, 4, 5, 6, 7 or 8, and even more preferably y is 1, 2, 3 or 4. Most preferably y is 1 or 2. In yet another preferred embodiment, y is 2, 4, 6 or 8. This embodiment is particularly preferred when the glycoprotein to be modified is an antibody, i.e. when Pr is Ab.

In a further preferred embodiment y is 1, 2, 3 or 4 (preferably 2 or 4) and/or x is 1 or 2 (preferably 1), more preferably y is 1 or 2 and x is 1 or 2 (preferably 1), even more preferably y is 1 or 2 and x is 1.

In a preferred embodiment, C1 of the core-sugar moiety of the modified glycan, said glycan comprising a GlcNAc-Su(A)$_x$ disaccharide-moiety at the non-reducing end, is bonded to the protein via an N-glycosidic bond to a nitrogen atom in an amino acid residue in said protein, more preferably to an amide nitrogen atom in the side chain of an asparagine (Asn) or an arginine (Arg) amino acid. However, C1 of the core-sugar-moiety of said modified glycan may also be bonded to the protein via an O-glycosidic bond to an oxygen atom in an amino acid residue in said protein, more preferably to an oxygen atom in the side chain of a serine (Ser) or threonine (Thr) amino acid. In this embodiment, it is preferred that the core-sugar-moiety of said glycan is an O-GlcNAc-moiety or an O-GalNAc moiety, preferably an O-GlcNAc moiety. C1 of the core-sugar-moiety of said modified glycan may also be bonded to the protein via a C-glycosidic bond to a carbon atom on the protein, e.g. to tryptophan (Trp). As described above, a glycoprotein may comprise more than one oligosaccharide chains, and may constitute of a combination of N-linked, O-linked and C-linked glycoproteins.

Said modified glycan may be present at a native glycosylation site of a protein, but may also be introduced on a different site on a protein.

In a preferred embodiment the modified glycoprotein is a modified antibody (Ab), said antibody comprising a glycan comprising a GlcNAc-Su(A)$_x$ disaccharide-moiety at the non-reducing end. Such an antibody is herein also referred to as a modified antibody. A preferred modified antibody is an antibody according to formula (107) or (108) as defined above, wherein Pr is Ab. In this embodiment, it is further preferred that y is 1, 2, 3, 4, 5, 6, 7 or 8, and even more preferred that y is 1, 2, 3 or 4.

As was defined above, said antibody may be a whole antibody, but also an antibody fragment. When the antibody is a whole antibody, said antibody preferably comprises one or more, more preferably one, modified glycans on each heavy chain. Said whole antibody thus preferably comprises two or more, preferably two, four, six or eight of said glycans, more preferably two or four, and most preferably two glycans. In other words, when said antibody is a whole antibody, y is preferably 2, 4, 6 or 8, more preferably y is 2 or 4, and most preferably y is 2. When the antibody is an antibody fragment, it is preferred that y is 1, 2, 3 or 4, and more preferably y is 1 or 2.

It is further preferred that y is 1, 2, 3 or 4 and x is 1 or 2, and it is further preferred that y is 2 or 4 and x is 1.

In a preferred embodiment, said antibody is a monoclonal antibody (mAb). Preferably, said antibody is selected from the group consisting of IgA, IgD, IgE, IgG and IgM antibodies. More preferably, said antibody is an IgG antibody, and most preferably said antibody is an IgG1 antibody.

In a preferred embodiment, the glycoprotein in the modified antibody is attached to the conserved N-glycosylation site in the Fc-fragment at asparagine in the region 290-305, typically N297.

The sugar derivative $Su(A)_x$ and preferred embodiments thereof are described in detail above. The preferred embodiments of the process for the preparation of a modified glycoprotein also hold for the modified glycoprotein obtainable by said process. Thus, in a preferred embodiment, x is 1 or 2, more preferably x is 1. In another preferred embodiment, functional group A is a thiol group, a halogen, or a halogenated acetamido group, more preferably a halogen.

Antibody-Drug Conjugate

The present invention particularly relates to a glycoprotein-conjugate obtainable by the process for the preparation of an glycoprotein, wherein the glycoprotein-conjugate is an antibody-conjugate. An antibody-conjugate is herein defined as a an antibody that is conjugated to a molecule of interest (D) via a linker (L). The antibody-conjugate according to the invention may be conjugated to one or to more than one molecule of interest (D) via a linker (L). The preferred embodiments disclosed above for a glycoprotein-conjugate also apply to an antibody-conjugate.

In a further preferred embodiment, the antibody-conjugate according to the invention is an antibody-drug conjugate (ADC). An antibody-drug conjugate is herein defined as an antibody that is conjugated to a molecule of interest (D) via a linker (L), wherein D is selected from the group consisting of pharmaceutically active substances, and more preferably D is selected from the group consisting of drugs and prodrugs.

More preferably, the active substance is selected from the group consisting of pharmaceutically active compounds, in particular low to medium molecular weight compounds (e.g. about 200 to about 1500 Da, preferably about 300 to about 1000 Da), such as for example cytotoxins, antiviral agents, antibacterial agents, peptides and oligonucleotides. Examples of cytotoxins include colchicine, vinca alkaloids, camptothecins, doxorubicin, daunorubicin, taxanes, calicheamycins, tubulysins, irinotecans, an inhibitory peptide, amanitin, deBouganin, duocarmycins, maytansines, auristatins and pyrrolobenzodiazepines (PBDs). In a preferred embodiment, the cytotoxin is selected from the group consisting of camptothecins, doxorubicin, daunorubicin, taxanes, calicheamycins, duocarmycins, maytansines, auristatins and pyrrolobenzodiazepines (PBDs). In another preferred embodiment, the cytotoxin is selected from the group consisting of colchicine, vinca alkaloids, tubulysins, irinotecans, an inhibitory peptide, amanitin and deBouganin.

The invention thus also relates to an antibody-conjugate obtainable by the process for the preparation of an antibody-conjugate according to the invention.

The invention further relates to an antibody-conjugate according to the invention, wherein the molecule of interest D is an active substance, for use as a medicament.

The invention also relates to the use of an antibody-conjugate according to the invention, wherein the molecule of interest D is an active substance, for use in the treatment of cancer.

The invention further relates to an antibody-conjugate according to the invention, wherein the molecule of interest D is an active substance, for use in the treatment of breast cancer, more preferably for use in the treatment of HER2-positive breast cancer.

The invention also relates to a method for the treatment of cancer, comprising administering an antibody-drug conjugate according to the invention, in a therapeutically effective amount to a subject in need thereof.

The invention also relates to a method for the treatment of breast cancer, comprising administering an antibody-drug conjugate according to the invention, in a therapeutically effective amount to a subject in need thereof.

The invention also relates to a method for the treatment of HER2-positive breast cancer, comprising administering an antibody-drug conjugate according to the invention, in a therapeutically effective amount to a subject in need thereof.

The modified antibody, the antibody-conjugate and the processes for the preparation thereof according to the invention have several advantages over the processes, modified antibodies and antibody-conjugates known in the art.

As was described above, the processes known in the art for conjugation of a linker-toxin to antibodies still need to be improved, in terms of control of both site-specificity and stoichiometry. Despite the ability of ADCs to home in on their targets, the amount of drug estimated to get inside tumor cells is typically <2% of an administered dose. This problem is amplified by the unpredictable conjugation results of ADCs known in the art. It is important to avoid underconjugated antibodies, which decrease the potency, as well as highly conjugated species, which may have markedly decreased circulating half-lives, impaired binding to the target protein, and increased toxicity.

For antibody-drug conjugates, a measure for the loading of molecules of interest (e.g. drugs, active substances) onto the antibody is the so-called Drug to Antibody Ratio (DAR), which gives the average number of active substance molecules per antibody, calculated from a statistical distribution. The theoretical maximum value of DAR for a certain type of ADC is equal to the number of anchoring sites. As was described above, processes for the preparation of ADCs known from the prior art generally result in a product comprising a mixture of antibody-conjugates with a varying number of molecules of interest present in each antibody-conjugate, and in a DAR with a high standard deviation.

Figure 9:
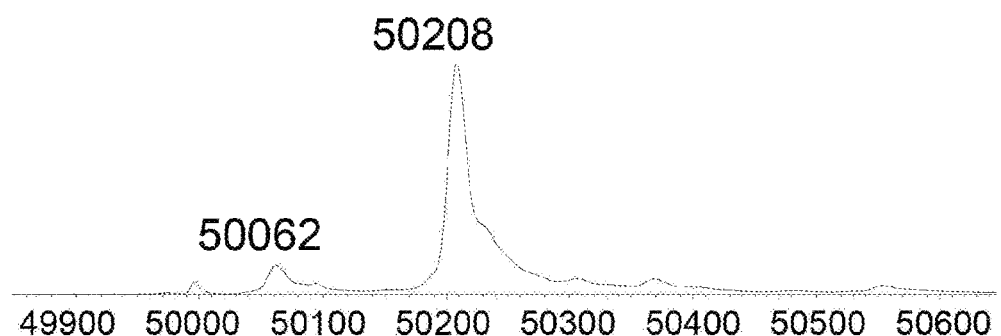
FIG. 9 shows the MS profile of conjugate 40, crude after treatment of 37 (X=Cl) with 32.

One of the advantages of the modified antibodies and the antibody-conjugates according to the invention is that these antibodies and antibody-conjugates are homogeneous, both in site-specificity and stoichiometry. Said modified antibodies and antibody-conjugates are obtained with a DAR very near to the theoretical value, and with a very low standard deviation. This also means that the antibody-conjugates according to the invention result in a more consistent product for preclinical testing. The homogeneity of the antibody-conjugate prepared by the process described herein becomes for example clear from the MS profile given in FIG. 9.

Another advantage of the processes and antibodies according to the invention involves the reduction of waste in manufacturing, thereby enhancing companies' cost-of-goods.

Figure 6:
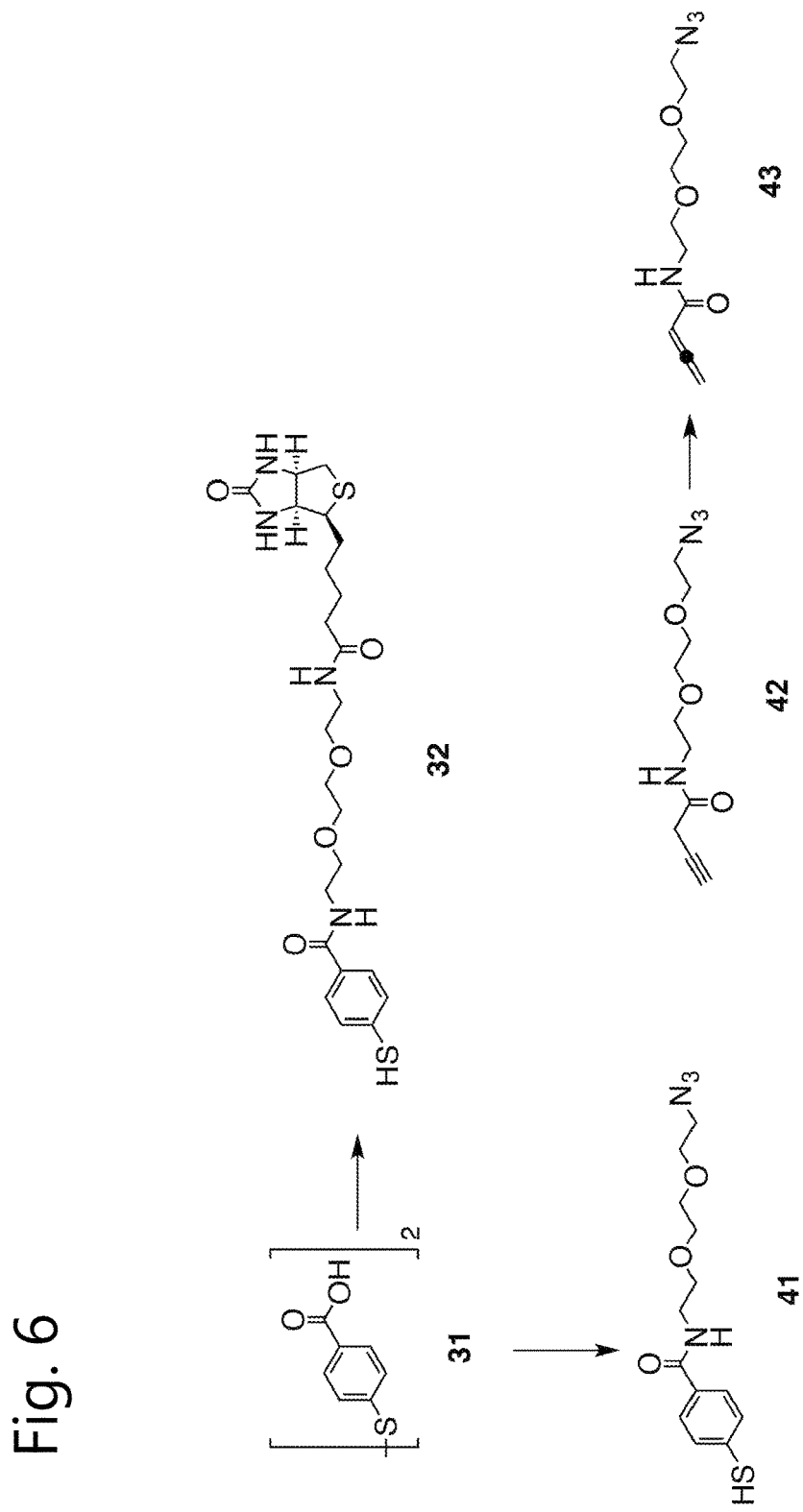
FIG. 6 shows the scheme for the synthetic preparation of a biotin-substituted thiophenol (32), of azide-substituted thiophenol (41) and of azide-allenamide construct 43 from propionic amide precursos 42.
Figure 7:
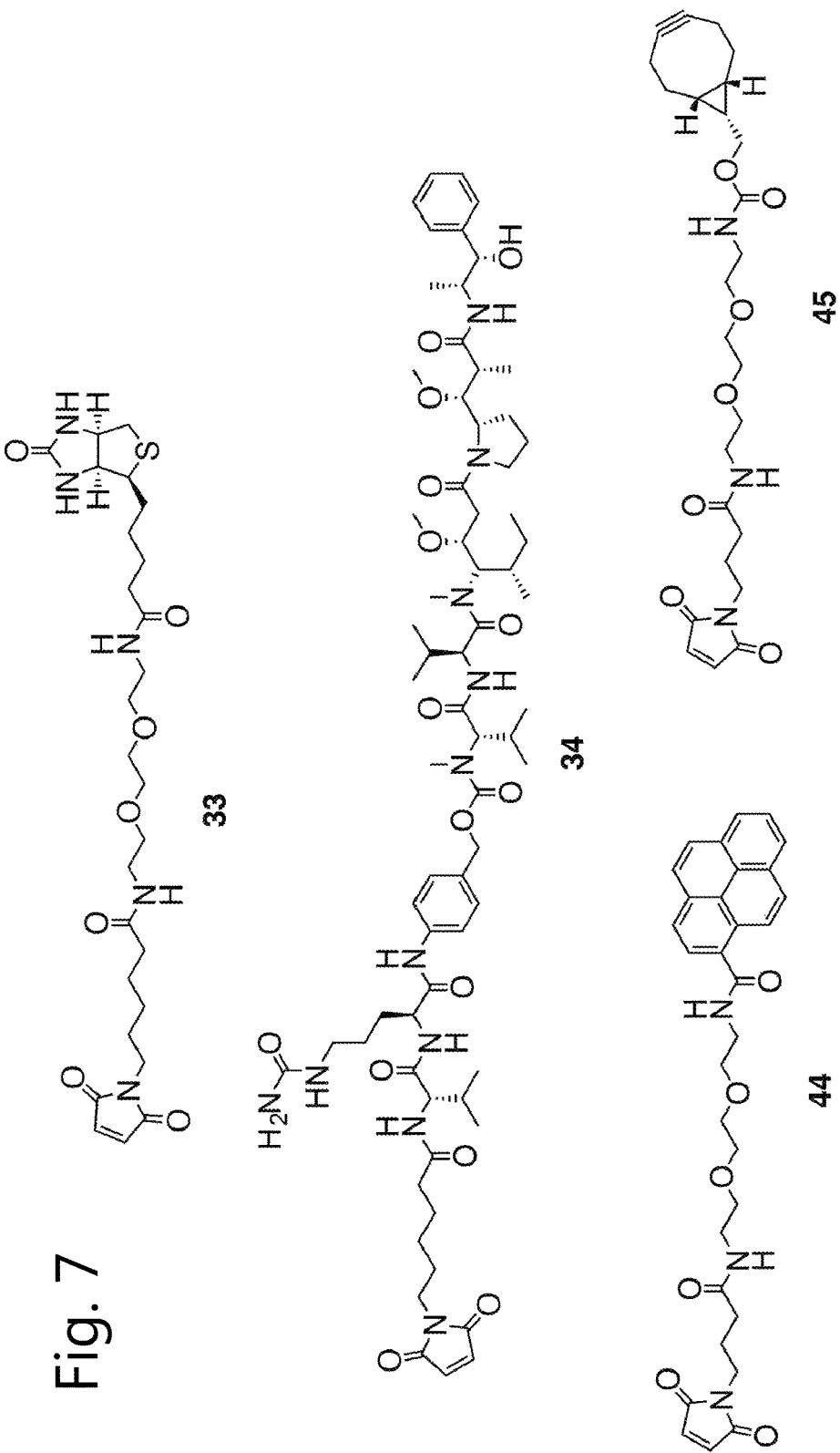
FIG. 7 shows the structures of maleimide derivatives of biotin (33), MMAF (34), pyrene (44) and BCN (45).
Figure 8:
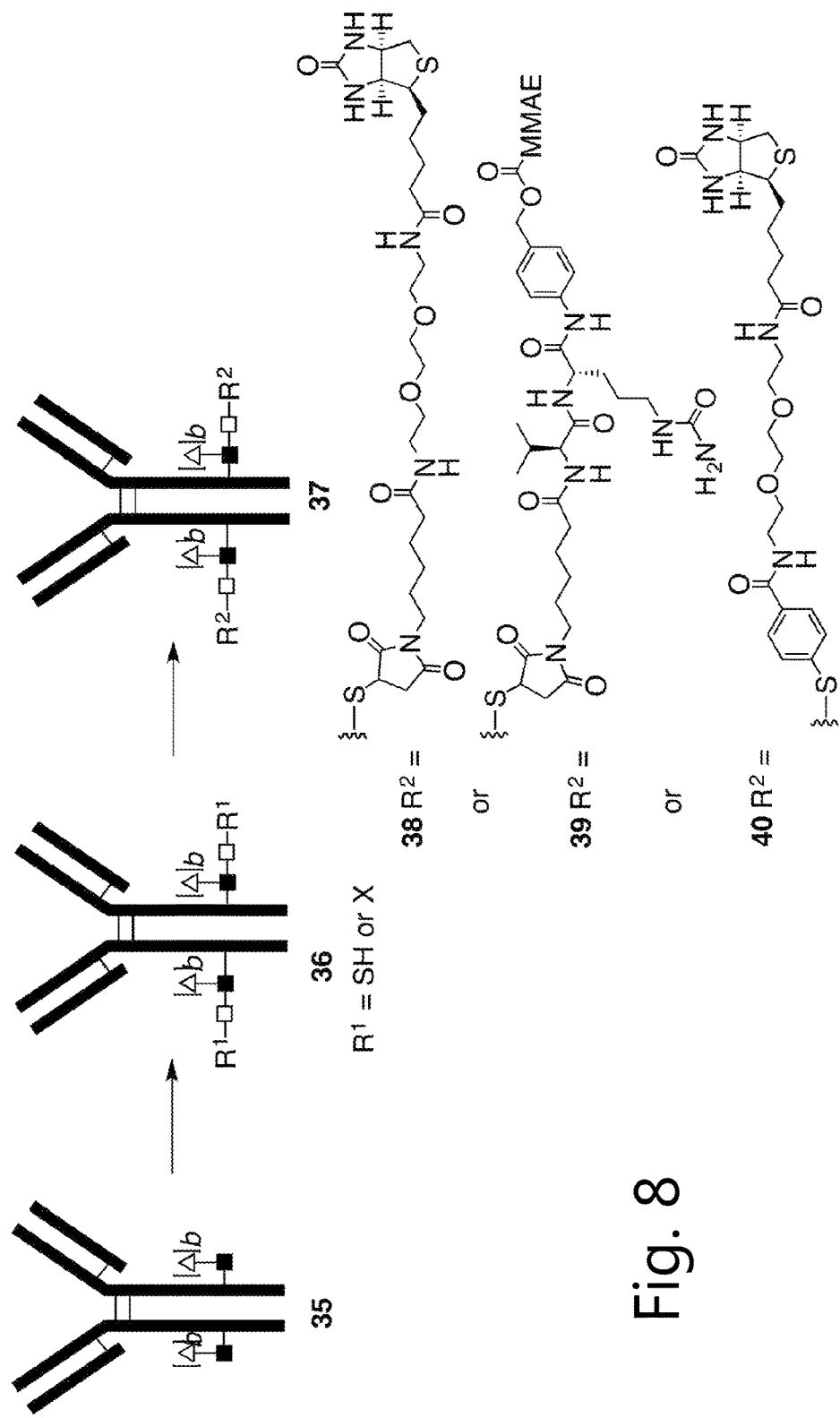
FIG. 8 shows a strategy for conversion of a trimmed monoclonal antibody 35 (comprising a core GlcNAc only). Upon the action of Gal-T1(Y289L) on 35, UDP-GalNAc derivatives 28-30 can be selectively introduced onto the GlcNAc to give 36 (R=SH after deacetylation, or halogen). Thiol-containing 36 can be reacted with maleimide derivatives 33 or 34, leading to conjugates 38 or 39, respectively. Alternatively, halogenated derivative 36 can be conjugated by nucleophilic substitution of the halogen with a nucleophilic reagent such as DTT, MeOPhSH or $NO_2PhSH$, or compound 32, leading to 40.

When a thiol-modified antibody according to the invention is coupled to a linker-conjugate comprising a maleimide, the process is well-known in the art, highly robust and validated. Some examples of maleimide conjugates are provided in FIGS. 8 and 11. Many maleimide-functionalized toxins have been described, because currently the preferred methodology for antibody-drug conjugation involves the combination of a cysteine mutant of a mAb (THIOmAb) and a maleimide derivative of a toxin. It is well known that such thiol-maleimide conjugates can be prepared with a highly beneficial stoichiometry of reagents (small excess of maleimide component). It is also well known that the resulting thiol-maleimide conjugates may have limited stability, but in case the thiol is present on fucose, the stability is significantly enhanced. When a thiol-modified antibody according to the invention is coupled to a linker-conjugate comprising a halogenated acetamide derivative of a toxin, the efficiency of the process may be somewhat compromised with respect to maleimide conjugation and more undesired alternative conjugation may take place (e.g. on lysine side chains), but the desired product is an irreversibly formed (highly stable) thio-ether conjugate. When a thiol-modified antibody according to the invention is coupled to a linker-conjugate comprising a allenamide derivative of a toxin, the efficiency of the process may be somewhat compromised with respect to maleimide conjugation, and no undesired alternative conjugation is likely to take place (e.g. on lysine side chains), while the desired product is an irreversibly formed (highly stable) thio-ether conjugate. An example of an allenamide structure is provided in FIG. 6. When a halogen-modified antibody according to the invention is coupled to a linker-conjugate comprising a derivative of a toxin containing a nucleophilic group (thiol, alcohol, amine), such as the thiol-comprising structures represented in FIG. 6, the resulting conjugate is a thio-ether, such as the structures represented in FIGS. 8 and 10, a regular ether or an amino-ether, all of which are formed irreversibly. In contrast to the use of halogenated acetamides for conjugation to proteins containing free thiols (as in THIOmAbs or in a thiofucose-containing mAb), the enzymatic incorporation of a halogenated sugar substrate is not compromised by competitive aspecific reaction with nucleophilic side chains of other amino acids (e.g. lysine). The lack of aspecific reactions also pertains to the subsequent conjugation step where in this case excess of a nucleophilic derivative of a functional group is applied to the halogenated mAb.

Figure 10:
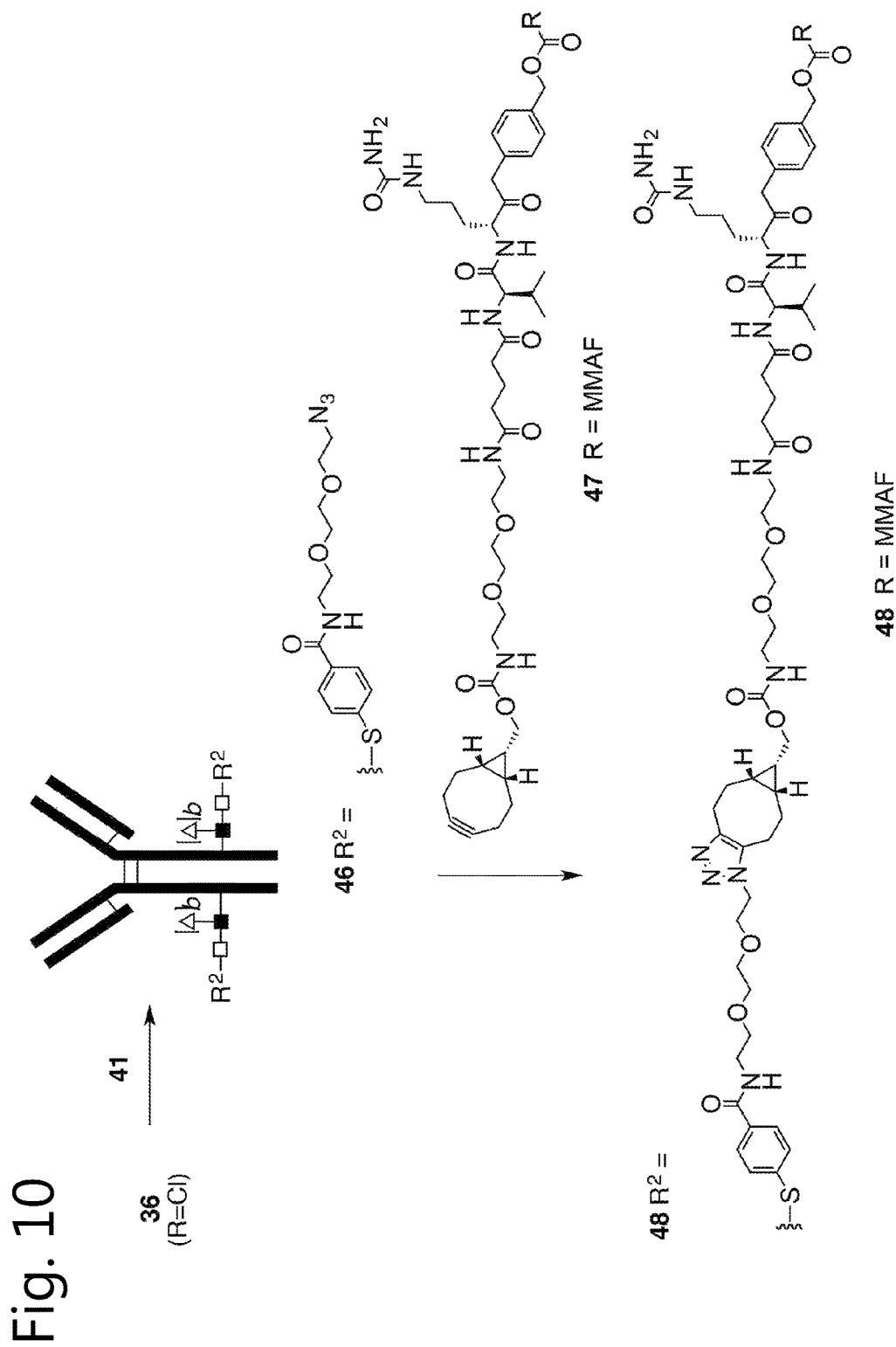
FIG. 10 shows a strategy for conversion of chlorinated antibody 36 with R=Cl (comprising a core GlcNAc substituted with a GalNAcCl). Upon conjugation of chlorinated derivative 36 by substitution with azido-bearing 41, an azido-derivative of the antibody is formed (46). The latter azide can be further conjugated with a BCN-toxin construct such as 47, leading to the antibody-drug conjugate 48.

One particular advantage of the use of a halogenated antibody is that it provides the opportunity to perform two-stage conjugation of a toxic payload. For example as illustrated in FIG. 10, reaction of the halogenated antibody with a thiophenol derivative bearing a pendant azide, provides an intermediate that can serve as the starting point for introduction of the toxic payload by means of copper-free click chemistry. By applying such a two-stage process, the stoichiometry of the (cheap and non-toxic) thiophenol derivative can be high, while the stoichiometry of the (expensive and highly toxic) payload can be kept low.

Figure 11:
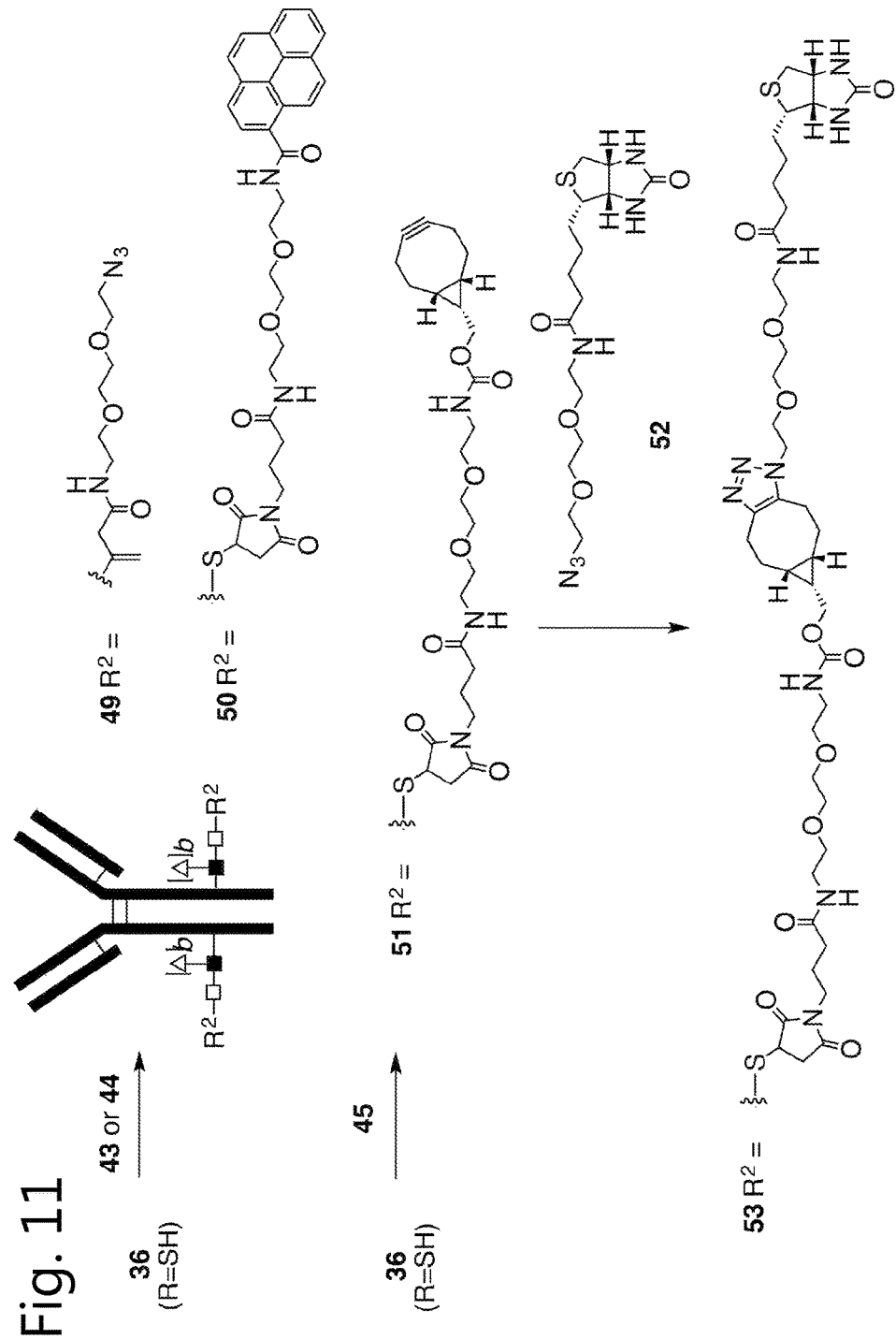
FIG. 11 shows a strategy for conversion of a thiolated monoclonal antibody 36 (comprising a core GlcNAc substituted with thiolated galactose derivative). Thiol-containing 36 can be reacted with maleimide derivatives 43, 44 or 45 leading to conjugates 49, 50 or 51 respectively. The latter conjugate 51, bearing the BCN-moiety can be further conjugated with an azide-biotin construct such as 52, leading to the antibody-biotin conjugate 53.

One particular advantage of the use of a thiol-comprising antibody is that it provides the opportunity to perform two-stage conjugation of a toxic payload. For example as illustrated in FIG. 11, reaction of the thiol-comprising antibody with an allenamide derivative bearing a pendant azide, provides a stable intermediate that can serve as the starting point for introduction of the toxic payload by means of copper-free click chemistry (in the example biotin is used as a representative for a toxic payload). By applying such a two-stage process, the stoichiometry of the (cheap and non-toxic) allenamide derivative can be high, while the stoichiometry of the (expensive and highly toxic) payload can be kept low.

Additional advantages are thus the stability of antibody-conjugates according to the invention, as well as the straightforward and generally applicable process for the introduction of a thiol group, a halogen, a sulfonyloxy group, a halogenated acetamido group, a mercaptoacetamido group and a sulfonated hydroxyacetamido group into an antibody.

Figure 12:
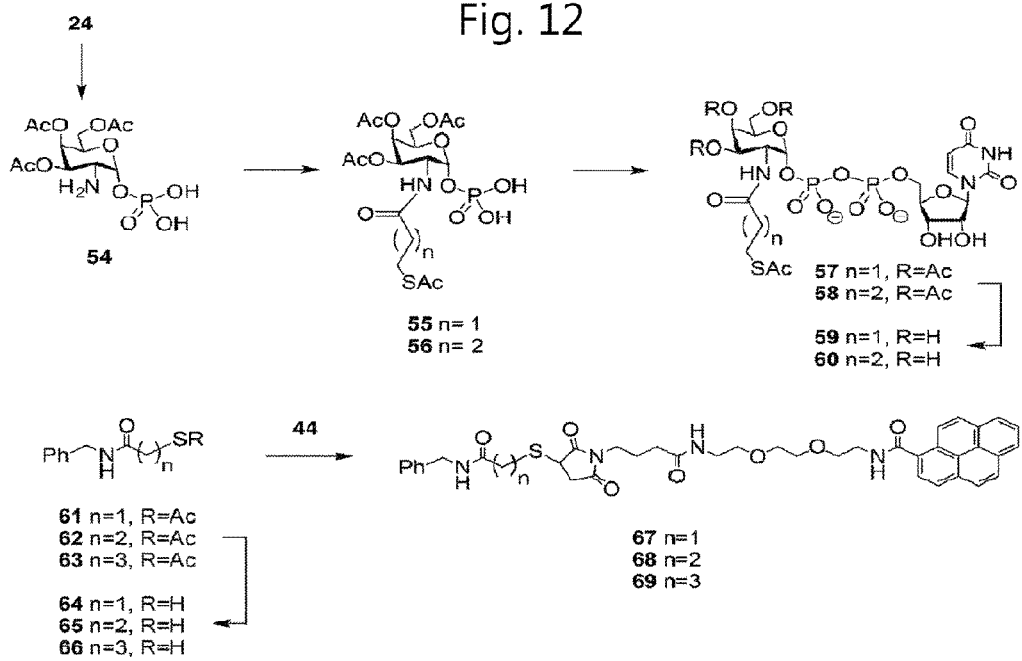
FIG. 12 shows the synthetic route for the preparation of the acetyl-protected GalNAc derivatives UDP-GalNProSAc (57) and UDP-GalNBuSAc (58) and the thiol-containing GalNAc derivatives UDP-GalNProSH (59) and UDP-GalNBuSH (60). Also shown is the synthetic route for preparation of the maleimide conjugates of compounds 64-66, model compounds for conjugates of GalNAcSH, GalNProSH and GalNBuSH, respectively.

One additional advantage for the preparation of thiol-comprising antibodies by the process described herein is that the starting UDP-sugars can be readily synthesized, as exemplified in FIG. 12.

Finally, an advantage preparing antibody conjugates by connecting via the glycan chain provides the opportunity to prepare a large number of isomers by means of engineering of glycomutants of the native antibody. Examples of different glycoforms (with R=glycan) of the native antibody are depicted in FIG. 13.

EXAMPLES

Synthesis

Examples 1-5: Synthesis of UDP-GalNAc Derivatives 28-31

The reaction scheme of the synthesis of UDP-GalNAc derivatives 28-31, starting from 24, as performed in Examples 1-4, is shown in Figure Y.

Example 1. Synthesis of UDP-GalNH$_2$

Compound 24 was prepared from D-galactosamine according to the procedure described for D-glucosamine in Linhardt et al., *J. Org. Chem.* 2012, 77, 1449-1456.

$^1$H-NMR (300 MHz, CD$_3$OD): δ 5.69 (dd, J=6.84, 6.84 Hz, 1H), 5.43-5.41 (m, 1H), 5.35 (dd, J=10.9, 3.4 Hz, 1H), 4.54 (t, J=6.48 Hz, 1H), 4.23-4.12 (m, 1H), 4.04 (dd, J=10.9, 6.1 Hz, 1H), 3.82 (dt, J=11.1, 2.7 Hz, 1H), 2.12 (s, 3H), 2.00 (s, 3H), 1.99 (s, 3H). LRMS (ESI−) calcd for C$_{12}$H$_{18}$N$_3$O$_{11}$ (M−H$^+$) 410.06. found 410.1.

Next, compound 24 was coupled to UMP according to Baisch et al. *Bioorg. Med. Chem.*, 1997, 5, 383-391).

Thus, a solution of D-uridine-5'-monophosphate disodium salt (1.49 g, 4.05 mmol) in H$_2$O (15 mL) was treated with DOWEX 50W×8 (H$^+$ form) for 30 minutes and filtered. The filtrate was stirred vigorously at rt while tributylamine (0.966 mL, 4.05 mmol) was added dropwise. After 30 minutes of further stirring, the reaction mixture was lyophilized and further dried over P$_2$O$_5$ under vacuum for 5 h.

The resulting tributylammonium uridine-5'-monophosphate was dissolved in dry DMF (25 mL) in an argon atmosphere. Carbonyldiimidazole (1.38 g, 8.51 mmol) was added and the reaction mixture was stirred at r.t. for 30 min. Next, dry MeOH (180 μL) was added and stirred for 15 min to remove the excess CDI. The leftover MeOH was removed under high vacuum for 15 min. Subsequently, compound 24 (2.0 g, 4.86 mmol) was dissolved in dry DMF (25 mL) and added dropwise to the reaction mixture. The reaction was allowed to stir at rt for 2 d before concentration in vacuo. The consumption of the imidazole-UMP intermediate was monitored by MS. Flash chromatography (7:2:1-5:2:1 EtOAc:MeOH:H$_2$O) afforded product 25 (1.08 g, 1.51 mmol, 37%).

$^1$H-NMR (300 MHz, D$_2$O): δ 7.96 (d, J=8.0 Hz, 1H), 5.98-5.94 (m, 2H), 5.81-5.79 (m, 1H), 5.70 (dd, J=7.1, 3.3 Hz, 1H), 5.49 (dd, J=15.2, 2.6 Hz, 1H), 5.30 (ddd, J=18.5, 11.0, 3.2 Hz, 2H), 4.57 (q, J=6.0 Hz, 2H), 4.35-4.16 (m, 9H), 4.07-3.95 (m, 2H), 2.17 (s, 3H), 2.08 (s, 3H), 2.07 (s, 3H). LRMS (ESI-) calcd for C$_{21}$H$_{29}$N$_5$O$_{19}$P$_2$ (M-H$^+$) 716.09. found 716.3.

Compound 25 was deacetylated according to Kiso et al., *Glycoconj. J.*, 2006, 23, 565-573).

Thus, compound 25 (222 mg, 0.309 mmol) was dissolved in H$_2$O (2.5 mL) and triethylamine (2.5 mL) and MeOH (6 mL) were added. The reaction mixture was stirred for 3 h and then concentrated in vacuo to afford crude UDP-2-azido-2-deoxy-D-galactose (26). $^1$H-NMR (300 MHz, D$_2$O): δ 7.99 (d, J=8.2 Hz, 1H), 6.02-5.98 (m, 2H), 5.73 (dd, J=7.4, 3.4 Hz, 1H), 4.42-4.37 (m, 2H), 4.30-4.18 (m, 4H), 4.14-4.04 (m, 2H), 3.80-3.70 (m, 2H), 3.65-3.58 (m, 1H). LRMS (ESI-) calcd for C$_{15}$H$_{23}$N$_5$O$_{16}$P$_2$ (M-H$^+$) 590.05. found 590.2.

Finally, to a solution of compound 26 in H$_2$O:MeOH 1:1 (4 mL) was added Lindlar's catalyst (mg). The reaction was stirred under a hydrogen atmosphere for 5 h and filtered over celite. The filter was rinsed with H$_2$O (10 ml) and the filtrate was concentrated in vacuo to afford the UDP-D-galactosamine (UDP-GalNH$_2$, 27) (169 mg, 0.286 mmol, 92% yield). $^1$H-NMR (300 MHz, D$_2$O): δ 7.93 (d, J=8.1 Hz, 1H), 5.99-5.90 (m, 2H), 5.76-5.69 (m, 1H), 4.39-4.34 (m, 2H), 4.31-4.17 (m, 5H), 4.05-4.01 (m, 1H), 3.94-3.86 (m, 1H), 3.82-3.70 (m, 3H), 3.30-3.16 (m, 1H). LRMS (ESI-) calcd for C$_{15}$H$_{25}$N$_3$O$_{16}$P$_2$ (M-H$^+$) 564.06. found 564.1.

Example 2. Synthesis of UDP-GalNAcSAc (28a)

UDP-D-galactosamine (27) (45 mg, 0.0796 mmol) was dissolved in buffer pH 7 (0.5 M K$_2$HPO$_4$) (2 mL). N-Succinimidyl-S-acetylthioacetate (37 mg, 0.159 mmol) and DMF (2 mL) were added and the reaction was stirred overnight at rt. Another 36 mg of N-succinimidyl-S-acetylthioacetate were added and after 3 h the reaction was concentrated in vacuo. Flash chromatography (7:2:1-5:2:1 EtOAc:MeOH:H$_2$O) afforded UDP-GalNAcSAc (28a) (28 mg, 0.041 mmol, 52%).

$^1$H-NMR (300 MHz, D$_2$O): δ 7.84 (d, J=8.1 Hz, 1H), 5.90-5.82 (m, 2H), 5.48-5.41 (m, 1H), 4.29-4.22 (m, 2H), 4.20-4.00 (m, 5H), 3.98-3.82 (m, 2H), 3.79-3.59 (m, 4H), 2.30 (s, 3H). LRMS (ESI-) calcd for C$_{19}$H$_{29}$N$_3$O$_{18}$P$_2$S (M-H$^+$) 680.06. found 680.1.

Example 3. Synthesis of UDP-GalNAcCl (29)

UDP-D-galactosamine (27) (42 mg, 0.074 mmol) was dissolved in 0.1 M NaHCO$_3$ (1 mL) and N-(Chloroacetoxy)succinimide (29 mg, 0.149 mmol) (prepared according to Hosztafi et al., *Helv. Chim. Acta*, 1996, 79, 133-136) and DIVIF (1 mL) were added. The reaction was stirred overnight at r.t., another 10 mg of N-(Chloroacetoxy)succinimide was added and stirring was continued overnight. The reaction was concentrated in vacuo and purified by flash chromatography (7:2:1-5:2:1 EtOAc:MeOH:H$_2$O) afforded UDP-GalNAcCl (29) (25 mg, 0.039 mmol, 53%).

$^1$H-NMR (300 MHz, D$_2$O): δ 7.84 (d, J=8.1 Hz, 1H), 5.89-5.84 (m, 2H), 5.53-5.46 (m, 1H), 4.33-4.00 (m, 9H), 3.99-3.88 (m, 2H), 3.77-3.59 (m, 2H), 1.83 (s, 1H). LRMS (ESI-) calcd for C$_{17}$H$_{26}$ClN$_3$O$_{17}$P$_2$ (M-H$^+$) 640.03 (100%), 642.03 (32%), found 640.1 (100%), 642.2 (35%).

Example 4. Synthesis of UDP-GalNAcBr (30)

UDP-D-galactosamine (27) (42 mg, 0.088 mmol) was dissolved in 0.1 M NaHCO$_3$ (3 mL) and N-(bromoacetoxy)succinimide 63 mg, 0.265 mmol) (prepared according to Hosztafi et al., *Helv. Chim. Acta*, 1996, 79, 133-136) and DMF (2 mL) were added. The reaction was stirred overnight at r.t. and concentrated in vacuo. The compound was purified by flash chromatography (7:2:1-5:2:1 EtOAc:MeOH:H$_2$O) afforded UDP-GalNAcBr (30) (28 mg, 0.048 mmol, 65%).

$^1$H-NMR (300 MHz, D$_2$O): δ 7.86 (d, J=3.2 Hz, 1H), 5.97-5.84 (m, 2H), 5.54-5.46 (m, 1H), 4.33-4.04 (m, 6H), 3.99-3.85 (m, 2H), 3.79-3.60 (m, 2H), 2.75-2.68 (m, 3H). LRMS (ESI-) calcd for C$_{17}$H$_{26}$BrN$_3$O$_{17}$P$_2$ (M-H$^+$) 683.98 (100%), 685.98 (98%), found 687.1 (100%), 688.0 (92%), 686.0 (85%), 689.0 (72%).

Example 6. Synthesis of 4,4'-Disulfanediyldibenzoic Acid (31)

To a solution of 4-mercaptobenzoic acid (0.20 g, 1.30 mmol) in EtOH (10 mL) was added I$_2$ (0.20 g, 0.65 mmol) and Et$_3$N (0.54 mL, 395 mg, 3.90 mmol). The resulting mixture was stirred for 16 h. After addition of 10% aqueous Na$_2$S$_2$O$_3$ and 0.01 M aqueous HCl (25 mL), the mixture was partially concentrated and 1M aqueous HCl was added (1 mL). EtOAc (20 mL), DCM (50 mL) and water (10 mL) were added and the product was filtered off and dried in vacuo. The desired product (4,4'-disulfanediyldibenzoic acid) was obtained as white solid (180 mg, 0.59 mmol, 90%) and used without further purification (see below). $^1$H NMR (300 MHz, DMSO) δ (ppm) 7.96-7.88 (m, 4H), 7.68-7.59 (m, 4H).

Example 7. Synthesis of Mercapto-D-Biotin Conjugate (32)

A solution of tert-butyl (2-(2-(2-aminoethoxy)ethoxy)ethyl)carbamate (451 mg, 1.82 mmol) in anhydrous DMF (5 mL) was placed under an argon atmosphere. D-Biotin (445 mg, 1.82 mmol), EDCI (418 mg, 2.18 mmol), HOBt (343 mg, 2.54 mmol), diisopropylethylamine (317 μL, 235 mg, 1.82 mmol) and anhydrous DMF (2 mL) were added. The resulting mixture was stirred for 24 h and concentrated. The residue was purified via column chromatography (2%→10% MeOH in DCM). After concentration of the product containing fractions, the residue was dissolved in a mixture of EtOAc/DCM/MeOH (100 mL/20 mL/20 mL) and washed with aqueous saturated NH$_4$Cl (2×100 mL). The organic mixture was dried (Na$_2$SO$_4$) and concentrated to 20 mL. The desired product (biotin-PEG$_2$-NHBoc) precipitated as a colorless glass (228 mg, 0.48 mmol, 26%) and used in the next step. $^1$H NMR (300 MHz, CD$_3$OD) δ (ppm) 4.49 (dd, J=7.4, 4.5 Hz, 1H), 4.30 (dd, J=7.9, 4.4 Hz, 1H), 3.62 (s, 4H), 3.55 (t, J=5.5 Hz, 2H), 3.52 (t, J=5.6 Hz, 2H) 3.40-3.15 (m, 5H), 2.93 (dd, J=12.7, 5.0 Hz, 1H)f, 2.71 (d, J=12.8 Hz, 1H), 2.22 (t, J=7.4 Hz, 2H), 1.81-1.40 (m, 6H), 1.44 (s, 9H).

A solution of biotin-PEG$_2$-NHBoc (208 mg, 0.44 mmol) was dissolved in MeOH (5 mL). After addition of acetyl chloride (250 μL, 275 mg, 3.5 mmol), the mixture was stirred for 17 h and concentrated. The residue was co-evaporated with EtOAc (5 mL), which quantitatively yielded the product as a yellow solid. The product (biotin-PEG$_2$-NH$_2$) was used in the next step without further purification.

To a solution of 4,4'-disulfanediyldibenzoic acid (31, 20 mg, 0.065 mmol) in DMF (1 mL) were added HATU (55 mg, 0.144 mmol) and diisopropylamine (70 µL, 50 mg, 0.39 mmol). Biotin-PEG$_2$-NH$_2$ (53 mg, 0.130 mmol) was added as a solution in DMF. The resulting mixture was stirred for 19 h and poured out in a mixture of DCM (20 mL) and saturated aqueous NH$_4$Cl (20 mL). After separation, the organic phase was dried (Na$_2$SO$_4$). The residue was purified via column chromatography (5%→20% MeOH in DCM). The desired product (biotin-PEG$_2$-SS-PEG$_2$-Biotin) was obtained as a white solid (21 mg, 0.021 mmol, 32%). LRMS (ESI+) calcd for C$_{46}$H$_{66}$N$_8$O$_{10}$S$_4$ (M+H$^+$) 1019.39. found 1020.1.

To a cooled (0° C.) solution of biotin-PEG$_2$-SS-PEG$_2$-biotin (3.5 mg; 3.4 µmol) in a mixture of THF (0.5 mL) and EtOH (0.5 mL) was added NaBH$_4$ (0.5 mg, 12 µmol). While warming up to rt, the mixture was stirred for 2 h and concentrated. The residue was taken up in water (1 mL) and 10 µL 1 M aqueous HCl was added. The desired product was extracted with DCM (2×2 mL). The combined organic layers were dried (Na$_2$SO$_4$) and concentrated to yield the title compound (32) (2.7 mg, 78%). LRMS (ESI+) calcd for C$_{23}$H$_{35}$N$_4$O$_5$S$_2$ (M+H$^+$) 511.20. found 511.2.

Example 8. Synthesis of Maleimide-Biotin Conjugate 33

To a solution of N-succinimidyl 6-maleimidocaproate (10 mg, 0.032 mmol) in 1 mL DMF was added a solution of biotin-PEG$_2$-NH$_2$ (13 mg, 0.032 mmol) and Et$_3$N (9 µL, 6.5 mg, 0.064 mmol) in DMF (1 mL). The mixture was stirred for 1 h and poured out in a mixture of DCM (10 mL) and aqueous saturated NaHCO$_3$ (10 mL). After separation, the organic layer was dried (Na$_2$SO$_4$) and concentrated, Column chromatography (2→20% MeOH in DCM) afforded the desired product 33 according to LRMS analysis. LRMS (ESI+) calcd for C$_{26}$H$_{42}$N$_5$O$_7$S (M+H$^+$) 568.28. found 568.2.

Conjugations
Antibody Glycosylation Mutant

Specific mutants of trastuzumab were derived from literature (Qu et al., *J. Immunol. Methods* 1998, 213, 131), in particular L196N and G164S or de novo designed, in particular V363T. In all three cases, asparagine 297 was mutated to glutamine (N297Q) to remove the native glycosylation site.

Both native trastuzumab and mutant antibodies were transiently expressed by Evitria (Zurich, Switzerland).
General Protocol for Mass Spectral Analysis of IgG A solution of 50 µg (modified) IgG, 1 M Tris-HCl pH 8.0, 1 mM EDTA and 30 mM DTT with a total volume of approximately 70 µL it was incubated for 20 minutes at 37° C. to reduce the disulfide bridges allowing to analyze both light and heavy chain. If present, azide-functionalities are reduced to amines under these conditions. Reduced samples were washed trice with milliQ using an Amicon Ultra-0.5, Ultracel-10 Membrane (Millipore) and concentrated to 10 µM (modified) IgG. The reduced IgG was analyzed by electrospray ionization time-of-flight (ESI-TOF) on a JEOL AccuTOF. Deconvoluted spectra were obtained using Magtran software.

Examples 9-12: General Protocol for Trimming of IgG Glycans

Trimming of IgG glycans was performed using endo S from *Streptococcus pyogenes* (commercially available from Genovis, Sweden). The IgG (10 mg/mL) was incubated with endo S (40 U/mL final concentration) in 25 mM Tris pH 8.0 for 16 hours at 37° C.

Example 9. Trimming of Native Trastuzumab

Trastuzumab with base MS peak 50591 Da was subjected to the trimming protocol above. After deconvolution of peaks, the mass spectrum showed one peak of the light chain and two peaks of the heavy chain. The two peaks of heavy chain belonged to one major product (49495 Da, 90% of total heavy chain), resulting from core GlcNAc(Fuc)-substituted trastuzumab, and a minor product (49351 Da, ±10% of total heavy chain), resulting from core GlcNAc-substituted trastuzumab.

Example 12. Trimming of Trastuzumab-Mutant N297Q, V363T

Trastuzumab-(N297Q, V363T) mutant (10 mg/mL) with major base MS peaks at 50934, 51227 and 51517 Da, corresponding to G2F, G2FS1 and G2FS2 glycosylation isoforms, was incubated with Endoglycosidase F3 (EndoF3, 25 mU/mg IgG) from *Elizabethkingia meningosepticum* (commercially available from QA-Bio) in 100 mM sodium citrate pH 4.5 for 16 hrs, which led to complete deglycosylation (major heavy chain product of 49515 Da resulting from N297Q, V363T heavy chain with core GlNAc(Fuc) attached).

General Protocol for Glycosyltransfer of Modified Sugar to IgG

Enzymatic introduction of modified sugar onto IgG was effected with a mutant of bovine β1,4-galactosyltransferase (β1,4-Gal-T1-Y289L). The deglycosylated IgG (prepared as described above, 10 mg/mL) was incubated with a modified UDP-sugar derivative (0.4 mM) and β(1,4)-Gal-T1-Y289L (1 mg/mL) in 10 mM MnCl$_2$ and 25 mM Tris-HCl pH 8.0 for 15 hours at 30° C.

The modified IgG was incubated with protein A agarose (40 µL per mg IgG) for 2 hours at 4° C. The protein A agarose was washed three times with PBS and the IgG was eluted with 100 mM glycine-HCl pH 2.7. The eluted IgG was neutralized with 1 M Tris-HCl pH 8.0 and concentrated and washed with PBS using an Amicon Ultra-0.5, Ultracel-10 Membrane (Millipore) to a concentration of 10 mg/mL.

Example 13. Glycosyltransfer of UDP-Sugar 28a (UDP-GalNAcSAc) to Deglycosylated Trastuzumab Trimmed trastuzumab (250 µL, 10 mg/mL, 16.5 nmol) was incubated with UDP-GalNAcSAc (28a) (18.5 µL, 10 mM) and β(1,4)-Gal-T1(Y289L) (12.5 µL, 2 mg/mL) in 10 mM MnCl$_2$ and 25 mM Tris-HCl pH 6.0 for 16 hours at 30° C. The crude mixture was purified with ProtA and in order to maintain the low pH the column was washed with 25 mM Tris-HCl pH 6.0 and after elution with glycine.HCl buffer (pH 2.7, 0.1 M), the elution buffer was neutralized with Tris-HCl (pH 7.2, 1 M).

Via this protocol 1.1 mg of an IgG was obtained, AccuTOF analysis of which showed the 95% conversion of trast-(GalNAcSH)$_2$ into a single desired product (GalNAc SAc minus the acetate group, probably due to in situ deprotection with DTT (mass 49729, expected mass 49730). The other 5% was remaining starting material (mass 49494).

Example 14. Glycosyltransfer of UDP-Sugar 28a (GalNAcSAc) to Deglycosylated Trastuzumab (N297Q, V363T)

Trimmed trastuzumab(N297Q, V363T) (100 μL, 10 mg/mL, 6.6 nmol) was incubated with UDP-GalNAcSAc (28a) (14 μL, 10 mM) and β(1,4)-Gal-T1(Y289L) (10 μL, 2 mg/mL) in 10 mM $MnCl_2$ and 25 mM Tris-HCl pH 6.0 for 16 hours at 30° C. The crude mixture was purified with ProtA and in order to maintain the low pH the column was washed with 25 mM Tris-HCl pH 6.0 and after elution with glycine.HCl buffer (pH 2.7, 0.1 M), the elution buffer was neutralized with Tris-HCl (pH 7.2, 1 M). Via this protocol 0.25 mg of an IgG was obtained, AccuTOF analysis of which showed the presence of trast(N297Q, V363T)-(GalNAcSH)$_2$ as a single desired product (GalNAcSAc minus the acetate group, probably due to in situ deprotection with DTT (mass 49744, expected mass 49748).

Example 15. Glycosyltransfer of UDP-Sugar 29 (GalNAcCl) to Deglycosylated Trastuzumab Trimmed trastuzumab (100 μL, 10 mg/mL, 6.6 nmol) was incubated with UDP-GalNAcCl (29) (5 μL, 10 mM) and β(1,4)-Gal-T1(Y289L) (5 μL, 2 mg/mL) in 10 mM $MnCl_2$ and 25 mM Tris-HCl pH 6.0 for 16 hours at 30° C. The crude mixture was purified with ProtA according to the protocol for GalNAcSAc to afford trast-(GalNAcCl)$_2$ (0.36 mg). AccuTOF analysis showed complete conversion to the desired product (mass 49731, expected mass 49732).

Example 16. Glycosyltransfer of UDP-Sugar 29 (GalNAcCl) to Deglycosylated Trastuzumab (N297Q, V363T)

Trimmed trastuzumab N297Q V363T mutant (100 μL, 10 mg/mL, 6.6 nmol) was incubated with UDP-GalNAcCl (29) (5 μL, 10 mM) and β(1,4)-Gal-T1(Y289L) (5 μL, 2 mg/mL) in 10 mM $MnCl_2$ and 25 mM Tris-HCl pH 6.0 for 16 hours at 30° C. The crude mixture was purified with ProtA according to the protocol for GalNAcSAc to afford trast-(GalNAcCl)$_2$ (0.35 mg). AccuTOF analysis showed complete conversion to the desired product (mass 49750, expected mass 49750).

Example 17. Glycosyltransfer of UDP-Sugar 30 (GalNAcBr) to Deglycosylated Trastuzumab The trimmed trastuzumab (100 μL, 10 mg/mL, 6.6 nmol) was incubated with UDP-GalNAcBr (RHX) (15 μL, 10 mM) and β1,4-Gal-T1-Y289L (5 μL, 2 mg/mL) in 10 mM $MnCl_2$ and 25 mM Tris-HCl pH 6.0 for 16 hours at 30° C. The crude mixture was purified with ProtA according to the protocol for GalNaSAc to afford trast-(GalNacBr)$_2$ (0.34 mg). AccuTOF analysis showed 50% conversion to the desired product (mass 49777, expected mass 49776 and mass+DTT (reaction during analysis sample) 49849.5). The intramolecular substitution of the bromide was 30% (mass 49696, expected mass 49698) and 20% was remaining starting material.

Example 18. Conjugation of Trast-GalNAcCl with DTT

Crude trast-(GalNAcCl)$_2$ (2 μL, 10 mg/ml in 25 mM Tris-HCl pH 8.0) was incubated with DTT (2 μL, 0.2 M) for 10 minutes at 37° C. Subsequent analysis with AccuTOF showed 70% incooperation of DTT (mass 49849, expected mass 49850) and 30% intramolecular substitution of the chloride (mass 49697, expected mass 49698).

Example 19. Conjugation of Trast(GalNAcCl)$_2$ with p-NO$_2$PhSH

To a solution of trast-(GalNAcCl)$_2$ (7.5 μL, 26.6 mg/ml, 1.3 nmol) in 25 mM Tris-HCl pH 6.0 was added degassed Tris-HCl (7.5 μL, 100 mM pH 7.2) and a solution of degassed p-NO$_2$PhSH (7.5 μL, 0.10 mM, 750 nmol in MiliQ+10 mM EDTA) under argon atmosphere. Analysis after 4 h by AccuTOF showed 95% conversion to the desired product (mass 49849, expected mass 49851).

Example 20. Conjugation of Trast(GalNAcCl)$_2$ with p-MeOPhSH

To a solution of trast-(GalNAcCl)$_2$ (7.5 μL, 26.6 mg/ml, 1.3 nmol) in 25 mM Tris-HCl pH 6.0 was added degassed Tris-HCl (7.5 μL, 100 mM pH 7.2) and a solution of degassed p-MeOPhSH (1 μL, 0.10 mM, 100 nmol in MiliQ+10 mM EDTA) under argon atmosphere. Analysis after 4 h by AccuTOF showed 95% conversion to the desired product (mass 49835, expected mass 49836). SDS-PAGE analysis indicated that no reduction of disulfide bonds of the antibody had taken place.

Example 21. Conjugation of Trast(GalNAcCl)$_2$ with 32

To a solution of trast-(GalNAcCl)$_2$ (7.5 μL, 26.6 mg/ml, 1.3 nmol) in 25 mM Tris-HCl pH 6.0 was added degassed Tris-HCl (7.5 μL, 100 mM pH 7.2) and a solution of degassed 32 (1 μL, 0.10 mM, 100 nmol in 10 mM EDTA in MiliQ/DMF=1:1) under argon atmosphere. After overnight incubation the excess of reagent was removed by spinfilter purification after which analysis by AccuTOF showed complete conversion to the desired product 40 (mass 50208, expected mass 50206).

Example 22. Conjugation of Trast(GalNAcSH)$_2$ with Mc-Vc-PABA-MMAE (34)

Protein A purified trast-(GalNAcSH)$_2$ (5 μL, 20 mg/ml in 25 mM Tris-HCl pH 8.0), which was obtained using UDP-sugar 29 as described above, was incubated with mc-vc-PABA-MMAE (5 μL, 1 mM, commercially available from Concortis) in PBS for 16 hrs at room temperature. The excess of reagent was removed by spin-filter purification. Subsequent analysis with AccuTOF showed the presence of the desired product (mass 51051, expected mass+$Na^+$ 51050).

Example 23. Cloning and Expression of GalT Mutants Y289N, Y289F, Y289M, Y289V, Y289A, Y289G and Y289I The GalT mutant genes were amplified from a construct containing the sequence encoding the catalytic domain of GalT consisting of 130-402 aa residues, by the overlap extension PCR method. The wild type enzyme is represented by SEQ ID NO: 17. For Y289N mutant (represented by SEQ ID NO: 18), the first DNA fragment was amplified with a pair of primers: Oligo38_GalT_External_Fw (CAG CGA <u>CATATG</u> TCG CTG ACC GCA TGC CCT GAG GAG TCC represented by SEQ ID NO: 1) and Oligo19_GalT_Y289N_Rw (GAC ACC TCC AAA GTT CTG CAC GTA AGG TAG GCT AAA represented by SEQ ID NO: 2). The NdeI restriction site is underlined, while the mutation site is highlighted in bold. The second fragment was amplified with a pair of primers: Oligo29_GalT_External_Rw (CTG ATG GAT GGATCCCTA GCT CGG CGT CCC GAT GTC CAC represented by SEQ ID NO: 3) and Oligo18 GalT Y289N_Fw (CCT TAC GTG CAG AAC TTT GGA GGT GTC TCT GCT CTA represented by SEQ ID NO: 4). The BamHI restriction site is underlined, while the mutation site is highlighted in bold. The two fragments generated in the first round of PCR were fused in the second round using Oligo38_GalT_External_Fw and Oligo29_GalT_External_Rw primers. After digestion with NdeI and BamHI. This fragment was ligated into the pET16b vector cleaved with the same restriction enzymes. The newly constructed expression vector contained the gene encoding Y289N mutant and the sequence encoding for the His-tag from pET16b vector, which was confirmed by DNA sequencing results. For the construction of Y289F (represented by SEQ ID NO: 19), Y289M (represented by SEQ ID NO: 20), Y289I (represented by SEQ ID NO: 22), Y289A (represented by SEQ ID NO: 23) and Y289G (represented by SEQ ID NO: 24) mutants the same procedure was used, with the mutation sites changed to TTT, ATG, ATT, GTG, GCG or GGC triplets encoding for phenylalanine, methionine, isoleucine, valine, alanine or glycine, respectively. More specifically, for the construction of Y289F the first DNA fragment was amplified with a pair of primers defined herein as SEQ ID NO: 1 and SEQ ID NO: 5 and the second fragment was amplified with a pair of primers defined herein as SEQ ID NO: 3 and SEQ ID NO: 6 (be referred to Table 1 for the related sequences). Furthermore, for the construction of Y289M the first DNA fragment was amplified with a pair of primers defined herein as SEQ ID NO: 1 and SEQ ID NO: 7 and the second fragment was amplified with a pair of primers defined herein as SEQ ID NO: 3 and SEQ ID NO: 8. For the construction of Y289I the first DNA fragment was amplified with a pair of primers defined herein as SEQ ID NO: 1 and SEQ ID NO: 9 and the second fragment was amplified with a pair of primers defined herein as SEQ ID NO: 3 and SEQ ID NO: 10. For the construction of Y289V the first DNA fragment was amplified with a pair of primers defined herein as SEQ ID NO: 1 and SEQ ID NO: 11 and the second fragment was amplified with a pair of primers defined herein as SEQ ID NO: 3 and SEQ ID NO: 12. for the construction of Y289A the first DNA fragment was amplified with a pair of primers defined herein as SEQ ID NO: 1 and SEQ ID NO: 13 and the second fragment was amplified with a pair of primers defined herein as SEQ ID NO: 3 and SEQ ID NO: 14. For the construction of Y289G the first DNA fragment was amplified with a pair of primers defined herein as SEQ ID NO: 1 and SEQ ID NO: 15 and the second fragment was amplified with a pair of primers defined herein as SEQ ID NO: 3 and SEQ ID NO: 16 (be referred to Table 1 for the related sequences).

GalT mutants were expressed, isolated and refolded from inclusion bodies according to the reported procedure by Qasba et al. (*Prot. Expr. Pur.* 2003, 30, 219-229). After refolding, the precipitate was removed and the soluble and folded protein was isolated using a Ni-NTA column (His-Trap excel 1 mL column, GE Healthcare). After elution with 25 mM Tris-HCl pH 8.0, 300 mM NaCl and 200 mM imidazole, the protein was dialyzed against 25 mM Tris-HCl pH 8.0 and concentrated to 2 mg/mL using a spinfilter (Amicon Ultra-15 Centrifugal Filter Unit with Ultracel-10 membrane, Merck Millipore).

TABLE 1

Sequence identification of the primers used

| SEQ ID NO | Nucleotide sequence |
| --- | --- |
| SEQ ID NO: 1 | CAG CGA CAT ATG TCG CTG ACC GCA TGC CCT GAG GAG TCC |
| SEQ ID NO: 2 | GAC ACC TCC AAA GTT CTG CAC GTA AGG TAG GCT AAA |
| SEQ ID NO: 3 | CTG ATG GAT GGA TCC CTA GCT CGG CGT CCC GAT GTC CAC |
| SEQ ID NO: 4 | CCT TAC GTG CAG AAC TTT GGA GGT GTC TCT GCT CTA |
| SEQ ID NO: 5 | GAC ACC TCC AAA AAA CTG CAC GTA AGG TAG GCT AAA |
| SEQ ID NO: 6 | CCT TAC GTG CAG TTT TTT GGA GGT GTC TCT GCT CTA |
| SEQ ID NO: 7 | GAC ACC TCC AAA CAT CTG CAC GTA AGG TAG GCT AAA |
| SEQ ID NO: 8 | CCT TAC GTG CAG ATG TTT GGA GGT GTC TCT GCT CTA |
| SEQ ID NO: 9 | GAC ACC TCC AAA AAT CTG CAC GTA AGG TAG GCT AAA |
| SEQ ID NO: 10 | CCT TAC GTG CAG ATT TTT GGA GGT GTC TCT GCT CTA |
| SEQ ID NO: 11 | GAC ACC TCC AAA CAC CTG CAC GTA AGG TAG GCT AAA |
| SEQ ID NO: 12 | CCT TAC GTG CAG GTG TTT GGA GGT GTC TCT GCT CTA |
| SEQ ID NO: 13 | GAC ACC TCC AAA CGC CTG CAC GTA AGG TAG GCT AAA |
| SEQ ID NO: 14 | CCT TAC GTG CAG GCG TTT GGA GGT GTC TCT GCT CTA |

TABLE 1-continued

Sequence identification of the primers used

| SEQ ID NO | Nucleotide sequence |
|---|---|
| SEQ ID NO: 15 | GAC ACC TCC AAA GCC CTG CAC GTA AGG TAG GCT AAA |
| SEQ ID NO: 16 | CCT TAC GTG CAG GGC TTT GGA GGT GTC TCT GCT CTA |

Example 24. Synthesis of 4,4'-disulfanediyldibenzoic acid bishydroxysuccinimide ester To a suspension of 4,4'-disulfanediyldibenzoic acid 31 (550 mg, 1.79 mmol) in DCM (20 mL) was added EDC.HCl (770 mg, 3.95 mmol) and NHS (447 mg, 3.95 mmol). The mixture was stirred for 4 h and subsequent washed with water (2×20 mL), aqueous saturated NaHCO$_3$ (2×20 mL), dried over Na$_2$SO$_4$, filtrated and concentrated in vacuo. 4,4'-Disulfanediyldibenzoic acid bishydroxysuccinimide ester was used crude in the next reaction.

Example 25. Synthesis of 4,4'-disulfanediylbis(N-(2''-(2'-(2-azidoethoxy)-ethoxy)ethyl)benzamide)

To a solution of 2''-(2'-(2-azidoethoxy)ethoxy)ethan-1-amine (210 mg, 1 mmol) in DCM (10 mL) was added Et$_3$N (240 µL, 1.7 mmol) and the mixture was stirred for 5 min followed by the addition of the 4,4'-dithiodibenzoic acid bishydroxysuccinimide ester (240 mg, 0.5 mmol). After stirring overnight, the reaction mixture was concentrated under reduced pressure and the product was purified on flash column chromatography (DCM→DCM:MeOH, 96:4). The fractions containing the product were washed with water (3×20 mL), subsequent dried over Na$_2$SO$_4$, filtrated and concentrated in vacuo to yield 4,4'-disulfanediylbis(N-(2''-(2'-(2-azidoethoxy)ethoxy)ethyl)benzamide in 54% yield (168 mg, 0.27 mmol). $^1$H-NMR (400 MHz, CDCl$_3$) δ (ppm) 7.74-7.72 (m, 4H), 7.54-7.52 (m, 4H), 3.68-3.58 (m, 20H), 3.35 (t, 4H, J=4.8 Hz).

Example 26. Synthesis of Mercaptobenzoic Acid Derivative 41

To a solution of 4,4'-disulfanediyl-bis(N-(2''-(2'-(2-azidoethoxy)ethoxy)ethyl)-benzamide (22 mg, 0.036 mmol) in THF at 0° C. (1 mL) was added NaBH$_4$ (2.7 mg, 0.07 mmol). The slurry was stirred and after 3 and 6 h extra NaBH$_4$ (2 times 2.7 mg, 0.07 mmol) was added. The reaction was stirred for another hour followed by the addition of 0.1 M HCl (1 mL) and DCM (2 mL). The mixture was extracted with DCM (2×5 mL) and the combined organic layers were dried over Na$_2$SO$_4$, filtrated and concentrated in vacuo to yield 41 in 69% yield (16 mg, 0.05 mmol). $^1$H-NMR (400 MHz, CDCl$_3$) δ (ppm) 7.65-7.63 (m, 2H), 7.29-7.26 (m, 2H), 3.68-3.56 (m, 10H), 3.35 (t, 2H, J=6.4 Hz).

Example 27. Synthesis of N-(2-(2-(2-azidoethoxy)ethoxy)ethyl)but-3-ynamide (42)

To a solution of but-3-ynoic acid (15 mg, 0.18 mmol) in CH$_2$Cl$_2$ (2 mL) was added Mukayama reagens (66 mg, 0.27 mmol) and the suspension was stirred for 1 h followed by the dropwise addition of a premixed solution of 2-(2-(2-azidoethoxy)ethoxy)ethan-1-amine (17 mg, 0.20 mmol) and Et$_3$N (60 µL, 0.45 mmol) in CH$_2$Cl$_2$ (2 mL). After 30 min the mixture was concentrated under reduced pressure and subsequent water (5 mL) and EtOAc (5 mL) were added. The organic layer was washed with water (2×5 mL), dried over Na$_2$SO$_4$ filtrated and concentrated in vacuo. Flash chromatography (EtOAc:pentane 1:1→6:1) afforded product 42 (9 mg, 0.04 mmol, 21%). 1H-NMR (400 MHz, CDCl$_3$): δ 3.64-3.58 (m, 6H), 3.55-3.52 (m, 2H), 3.45-3.42 (m, 2H), 3.33 (t, J=4.8 Hz, 2H), 3.15 (d, J=2.4 Hz, 2H), 2.29 (t, J=2.8 Hz, 1H).

Example 28. Synthesis of N-(2-(2-(2-azidoethoxy)ethoxy)ethyl)buta-2-allenamide (43)

Butynamide 42 (9 mg, 0.04 mmol) was dissolved in dioxane (0.5 mL) followed by the addition K$_2$CO$_3$ (18% in water, 0.5 mL). The reaction mixture was heated to 40° C. for 2 h followed by the addition of citric acid (2 mL, 10% in water) and CH$_2$Cl$_2$ (2 mL). The water layer was extracted with CH$_2$Cl$_2$ (2×3 mL) and the organic layers were combined, dried over Na$_2$SO$_4$, filtrated and concentrated in vacuo to yield the product 43 (8 mg, 0.04 mmol, 89%). 1H-NMR (400 MHz, CDCl$_3$): δ 5.63 (t, J=6.4 Hz, 1H), 5.21 (d, J=6.7 Hz, 2H), 3.70-3.60 (m, 6H), 3.60-3.58 (m, 2H), 3.53-3.50 (m, 2H), 3.39 (t, J=4.8 Hz, 2H).

Example 29. Synthesis of 1-pyrenecarboxylic acid OSu ester

To a solution of 1-pyrenecarboxylic acid (65 mg, 0.24 mmol) in DCM/DMF (2 mL each) was added N-hydroxysuccinimide (34 mg, 0.29 mmol) and EDC.HCl (70 mg, 0.36 mmol). The reaction was stirred for 2 h and subsequent diluted with DCM (10 mL), washed with aqueous citric acid (10%, 5 mL) and saturated NaHCO$_3$ (3×5 mL), dried over Na$_2$SO$_4$, filtrated and concentrated in vacuo to give crude 1-pyrenecarboxylic acid hydroxysuccinimide ester.

Example 30. Synthesis of 44

1-Pyrenecarboxylic acid hydroxysuccinimide ester (480 mg, 1.38 mmol) was dissolved in DCM (15 mL) and tert-butyl (2-(2-(2-aminoethoxy)ethoxy)ethyl)carbamate (348 mg, 1.4 mmol and Et$_3$N (286 µL, 2.1 mmol) were added. The reaction mixture was stirred overnight and quenched with water (15 mL), the organic layer was washed with water (1×15 mL) and saturated aqueous NaHCO$_3$ (2×15 mL), dried over Na$_2$SO$_4$, filtrated and concentrated in vacuo. Purification via gradient flash column chromatography (DCM→DCM:MeOH 95:5) yielded the Boc-protected pyrene derivative (460 mg, 0.97 mmol, 70%).

Next, the Boc-protected pyrene derivative (460 mg, 0.97 mmol) was dissolved in methanol (10 mL). Acetylchloride (140 µL, 1.9 mmol) was added and after 1 and 3 h additional acetyl chloride (2×140 µL, 1.9 mmol) was added. After stirring for 4 h the mixture was concentrated under reduced pressure. Next, the crude product (100 mg, 0.24 mmol) was dissolved in DCM (3 mL) and 2,5-dioxopyrrolidin-1-yl 4-(2,5-dioxo-2,5-dihydro-1H-pyrrol-1-yl)butanoate (50 mg, 0.17 mmol) and Et$_3$N (73 µL, 0.52 mmol) were added. After stirring overnight the solution was quenched with water (3 mL), washed with water (2×3 mL), dried over Na$_2$SO$_4$, filtrated and concentrated. Purification via gradient flash column chromatography (DCM→DCM:MeOH 95:5) yielded 44 (69 mg, 0.13 mmol, 75%). $^1$H-NMR (400 MHz, CDCl$_3$) δ (ppm) 8.48 (d, 1H, J=9.2 Hz), 8.12 (d, 2H, J=7.6 Hz), 8.04-7.93 (m, 6H), 6.59 (bs, 1H), 6.38 (s, 2H), 5.99 (bs, 1H), 3.76-3.71 (m, 4H), 3.62-3.60 (m, 2H), 3.54-3.52 (m, 2H), 3.37 (t, 2H, J=5.2 Hz), 3.23-3.17 (m, 4H), 1.82 (t, 2H, J=6.8 Hz), 1.63 (q, 2H, J=7.2 Hz).

Example 31. Formation of Maleimide BCN Conjugate 45

To a solution of BCN—(POE)$_3$NH$_2$ (13 mg, 0.04 mmol) in DMA (1 mL) was added 4-maleimido butanoic acid hydroxysuccinimide ester (7 mg, 0.03 mmol), followed by incubation for 1 h. The solution was used as such in the conjugation experiments.

Example 32. Conjugation of Trast(GalNProSH)$_2$ with 34 to Give 39

Trastuzumab-(GalNProSH)$_2$ (1.0 mg, 10 mg/mL) was incubated with TCEP (6.6 µL, 10 mM in MiliQ), in PBS and 20 mM EDTA for 2 hours at rt. Subsequently, the reaction medium was exchanged to PBS using an Amicon Ultra-0.5, Ultracel-10 Membrane (Millipore). Dehydroascorbic acid (5.4 µL, 10 mM in DMSO) was added followed by incubation for 3 h. Maleimide-vc-PABA-MMAE 34 (1 µL, 10 mM in DMA) was added and the mixture was incubated for 35 min. Subsequently, a sample (2 µL) was taken for digestion with Fabricator™ (50 U in 10 µL PBS) and washed with MiliQ using an Amicon Ultra-0.5, Ultracel-10 Membrane (Millipore) and mass analysis showed the formation of 39 (25706, expected mass 25701).

Example 33. Formation of Trastuzumab-Conjugate 46

To a solution of 36 (R═Cl) (3 µL, 63 mg/ml, 1.3 nmol) in 25 mM Tris-HCl pH 6.0 was added Tris-HCl (10 µL, 100 mM pH 7.2) and a solution of 41 (10 µL, 10 mM, 100 nmol in MiliQ+10 mM EDTA+10% DMF). After incubation overnight, AccuTOF analysis showed >95% conversion to the desired product 46 (mass 50010, expected mass 50006).

Example 34. SPAAC of 46 with 47, Leading to Antibody-Drug Conjugate 48

The remaining reagent of example 33 was removed via spin-filtration (3×0.5 mL) to Tris-HCl (25 mM, pH 7.5) and BCN-vc-PABA-MMAF 47 (10 µL, 2 mM, 20 nmol in MiliQ+5% DMF) was added. After incubation overnight, AccuTOF analysis showed >95% conversion to the desired product 48 (mass 51566, expected mass 51564).

Example 35. Conjugation of Trast(GalNProSH)$_2$ with Allenamide 43, Leading to Conjugate 49

Trastuzumab-(GalNProSH)$_2$ (0.2 mg, 20 mg/mL) in 50 mM Tris-HCl pH 6.0 was incubated with N-(2″-(2′-(2-azidoethoxy)ethoxy)ethyl)buta-2-allenamide (43) (1 µL, 40 mM in DMA) and 50 mM Tris-HCl pH 8.8 (10 µL) overnigth at rt. Subsequent a sample (2 µL) was taken for digestion with Fabricator™ (50 U in 10 µL PBS) and washed with MiliQ using an Amicon Ultra-0.5, Ultracel-10 Membrane (Millipore) and mass analysis showed the formation of the desired product 49 (24627, expected mass 24627) as main product (about 70%).

Example 36. Conjugation of Trast(GalNProSH)$_2$ with 44, Leading to Conjugate 50

Trastuzumab-(GalNProSH)$_2$ (0.5 mg, 10 mg/mL) was incubated with TCEP (3.3 µL, 10 mM in MiliQ), in PBS and 20 mM EDTA for 2 hours at rt. Subsequent the reaction medium was exchanged to PBS using an Amicon Ultra-0.5, Ultracel-10 Membrane (Millipore). Dehydroascorbic acid (2.8 µL, 10 mM in DMSO) was added followed by incubation for 3 h. Pyrene maleimide 44 (1 µL, 10 mM in DMA) was added and the mixture was incubated for 35 min. Subsequent a sample (2 µL) was taken for digestion with Fabricator™ (50 U in 10 µL PBS) and washed with MiliQ using an Amicon Ultra-0.5, Ultracel-10 Membrane (Millipore) and mass analysis showed the formation of the desired product 50 (24929, expected mass 24929) as main product (about 85%).

Example 37. Conjugation of Trast(GalNProSH)$_2$ with 45 Followed by Addition of Biotine-N$_3$ (52)

Trastuzumab-(GalNBuSH)$_2$ (1 mg, 10 mg/mL) was incubated with TCEP (8.3 µL, 10 mM in MiliQ), in PBS and 20 mM EDTA for 2 hours at rt. Subsequent the reaction medium was exchanged to PBS using an Amicon Ultra-0.5, Ultracel-10 Membrane (Millipore). Dehydroascorbic acid (6.5 µL, 10 mM in DMSO) was added followed by incubation for 3 h. Compound 45 (3 µL premix, 40 mM in DMA) was added and the mixture was incubated for 35 min. Subsequently, a sample (2 µL) was taken for digestion with Fabricator™ (50 U in 10 µL PBS) and washed with MiliQ using an Amicon Ultra-0.5, Ultracel-10 Membrane (Millipore) and mass analysis showed the formation of the desired product 51 (24891, expected mass 24891) as main product (about 85%). The reaction mixture was spinfiltered to 25 mM Tris-HCl pH 7.5, two times, followed by the addition of 52 (3 µL, 40 mM in DMF). After incubation a sample was subjected to DTT as described above and mass analysis showed the formation of the desired product 53 (50658, expected mass 50650) as main product (about 85%), one of the remaining species is trimmed trastuzumab (49503, expected mass 49495).

Example 38. Synthesis of 52

2″-(2′-(2-azidoethoxy)ethoxy)ethan-1-amine (50 mg, 0.17 mmol) was dissolved in CH$_2$Cl$_2$ (2 mL) and biotine hydroxysuccinimide derivative (60 mg, 0.18 mmol) and Et$_3$N (52 µL, 0.37 mmol) were added. The reaction mixture was stirred overnight and quenched with water (5 mL) and CH$_2$Cl$_2$ (5 mL). The organic layer was washed with water (2×5 mL), dried over NaSO$_4$, filtrated and concentrated under reduced pressure. Flash chromatography (DCM→DCM:MeOH 9:1) afforded product 52 (13 mg, 0.03 mmol, 20%). LRMS (ESI+) calcd for C$_{16}$H$_{29}$N$_6$O$_4$S (M+H$^+$) 401.19. found 401.34.

Example 39. Synthesis of UDP-GalNProSH (59) and UDP-GalNBuSH (60) Derivatives The reaction scheme of the synthesis of UDP-GalNProSH and UDP-GalNBuSH derivatives 59+60, starting from 24, as performed in Examples xxx, is shown in FIG. 12.

Example 40. 3,4,6-tri-O-acetyl-D-galactosamine-1-phosphate (54)

To a solution of azide 24 (105 mg, 0.255 mmol) in MeOH (3 mL) was added Pd/C (20 mg). The reaction was stirred under a $H_2$ atmosphere for 2 h and filtered over celite. The filter was rinsed with MeOH (10 mL) and the filtrate was concentrated in vacuo to afford 54 (94 mg, 0.244 mmol, 96%).

$^1$H-NMR (300 MHz, $D_2O$): δ 5.87-5.76 (m, 1H), 5.44 (br s, 1H), 5.30-5.20 (m, 1H), 4.55 (t, J=6.3 Hz, 1H), 4.28-4.00 (m, 3H), 2.11 (s, 3H), 2.03 (s, 3H), 2.00 (s, 3H). LRMS (ESI) calcd for $C_{12}H_{19}NO_{11}P$ (M$^-$) 384.07. found 384.1.

Example 41. Synthesis of 55

To a solution of 54 (162 mg, 0.42 mmol) in DCM/DMF (2 mL each), acetylmercapto-3-propanoic acid hydroxysuccinimide ester (175 mg, 0.69 mmol) and $Et_3N$ (88 µL, 0.63 mmol) were added. After stirring overnight, the reaction mixture was concentrated under reduced pressure. Purification via flash column chromatography (EtOAc EtOAc:MeOH 30:70) yielded 55 (85 mg, 0.17 mmol, 39%). LRMS (ESI) calcd for $C_{17}H_{25}NO_{13}PS$ (M$^-$) 514.09. found 514.06.

Example 42. Synthesis of 57

Next, compound 55 was coupled to UMP according to Baisch et al. *Bioorg. Med. Chem.*, 1997, 5, 383-391.

Thus, a solution of D-uridine-5'-monophosphate disodium salt (1.49 g, 4.05 mmol) in $H_2O$ (15 mL) was treated with DOWEX 50W×8 (H$^+$ form) for 30 minutes and filtered. The filtrate was stirred vigorously at rt while tributylamine (0.966 mL, 4.05 mmol) was added dropwise. After 30 minutes of further stirring, the reaction mixture was lyophilized.

The resulting tributylammonium uridine-5'-monophosphate (103 mg, 0.20 mmol) was dissolved in dry DMF (2 mL) in an argon atmosphere. Carbonyldiimidazole (57 mg, 0.36 mmol) was added and the reaction mixture was stirred at r.t. for 30 min. Next, dry MeOH (7 µL) was added and stirred for 15 min to remove the excess CDI. The leftover MeOH was removed under high vacuum for 15 min. Subsequently, compound x (87 mg, 0.17 mmol) and N-methylimidizole HCl (118 mg, 0.85 mmol) were dissolved in dry DMF (2 mL) and added dropwise to the reaction mixture. The reaction was allowed to stir overnight before concentration in vacuo. Flash chromatography (9:2:1-5:2:1 EtOAc:MeOH:$H_2O$) afforded 57 (91 mg, 0.11 mmol, 65%). LRMS (ESI) calcd for $C_{26}H_{36}N_3O_{21}P_2S$ (M$^-$) 820.11. found 820.24.

Example 43. Synthesis of UDP-GalNProSH (59)

UDP-galactosamine derivative 57 (178 mg, 0.21 mmol) was dissolved in a mixture of water:MeOH:$Et_3N$ (3:7:3, 5 mL) and stirred until full deprotection was achieved according to LCMS. The reaction was concentrated under reduced pressure and split in two portions. One portion was stored, while the other half was purified on anion exchange column (Q HITRAP, 2×5 mL columns). First binding on the column was achieved via loading with buffer A (10 mM $NaHCO_3$) and the column was rinsed with 100 mL buffer A. Next a gradient to 25% B (250 mM $NaHCO_3$) was performed to elute the impurities such as diUMP. Increasing the gradient to 100% B eluted the product as dimer. The fractions were freeze-dried and subsequent dissolved in water (5 mL) followed by the addition of DTT (15 mg, 0.1 mmol) and $Et_3N$ (few drops). After 1 h the reduction was to completion and the solvents were removed under reduced pressure. Flash chromatography (6:2:1-3:2:1 EtOAc:MeOH:$H_2O$) afforded product 59 (17 mg, 0.03 mmol, 26%). LRMS (ESI) calcd for $C_{18}H_{28}N_3O_{17}P_2S$ (M$^-$) 652.07. found 652.03.

$^1$H-NMR (400 MHz, D2O): δ 7.86 (d, J=8.0 Hz, 1H), 5.88-5.86 (m, 2H), 5.48-5.45 (m, 1H), 4.28-4.05 (m, 8H), 3.95-3.85 (m, 1H), 3.68-3.65 (m, 2H), 2.69-2.67 (m, 2H), 2.60-2.55 (m, 2H).

Example 44. Synthesis of acetylmercapto-4-butanoic acid 4-bromobutanoic acid (1 g, 6 mmol) was dissolved in DMF (7 mL) followed by the addition of potassium thioacetate (1 g, 9 mmol). The reaction was stirred for 1 h and quenched by 1 M HCl (20 mL) and $Et_2O$ (20 mL). The organic layer was washed with 1 M HCl (3×20 mL), dried over $Na_2SO_4$, filtrated and concentrated. Flash chromatography (1:0-7:1 heptane:EtOAc+1% $Ac_2O$) afforded acetylmercapto-4-butanoic acid (450 mg, 2.7 mmol, 46%).

$^1$H-NMR (400 MHz, CDCl$_3$): δ 2.94 (t, J=7.2 Hz, 2H), 2.45 (t, J=7.2 Hz, 2H), 2.34 (s, 3H), 1.92 (q, J=6.8 Hz, 2H).

Example 45. Synthesis of acetylmercapto-4-butanoic acid hydroxysuccinimide ester Acetylmercapto-4-butanoic acid (450 mg, 2.7 mmol) was dissolved in $CH_2Cl_2$ (30 mL) followed by the addition of EDC.HCl (813 mg, 4.1 mmol) and N-hydroxysuccinimide (500 mg, 4.1 mmol). The reaction was stirred overnight and quenched with saturated aqueous $NaHCO_3$ (20 mL). The organic layer was washed with saturated aqueous $NaHCO_3$ (2×20 mL) and citric acid (1×10 mL). The organic layer was dried over $Na_2SO_4$, filtrated and concentrated, to give the title compound as a crude product (630 mg, 2.4 mmol, 90%).

Example 46. Synthesis of 56

To a solution of galactosamine derivative 54 (167 mg, 0.43 mmol) in DCM/DMF (2 mL each) was added acetylmercapto-4-butanoic acid hydroxysuccinimide (200 mg, 0.77 mmol) and $Et_3N$ (88 µL, 0.63 mmol). After stirring overnight, the reaction mixture was concentrated under reduced pressure. Purification via flash column chromatography (EtOAc→EtOAc:MeOH 30:70) yielded 56 (68 mg, 0.13 mmol, 30%). LRMS (ESI) calcd for $C_{18}H_{27}NO_{13}PS$ (M$^-$) 528.10. found 528.25.

Example 47. Synthesis of 58

Next, galactosamine derivative 56 was coupled to UMP according to Baisch et al. *Bioorg. Med. Chem.*, 1997, 5, 383-391.

Thus, a solution of D-uridine-5'-monophosphate disodium salt (1.49 g, 4.05 mmol) in $H_2O$ (15 mL) was treated with DOWEX 50W×8 (H+ form) for 30 minutes and filtered. The filtrate was stirred vigorously at rt while tributylamine (0.966 mL, 4.05 mmol) was added dropwise. After 30 minutes of further stirring, the reaction mixture was lyophilized.

The resulting tributylammonium uridine-5'-monophosphate (78 mg, 0.15 mmol) was dissolved in dry DMF (2 mL) in an argon atmosphere. Carbonyldiimidazole (43 mg, 0.27 mmol) was added and the reaction mixture was stirred at r.t. for 30 min. Next, dry MeOH (6 µL) was added and stirred for 15 min to remove the excess CDI. The leftover MeOH was removed under high vacuum for 15 min. Subsequently, compound 56 (68 mg, 0.13 mmol) and N-methylimidizole HCl (118 mg, 0.72 mmol) were dissolved in dry DMF (2 mL) and added dropwise to the reaction mixture. The reaction was allowed to stir overnight before concentration in vacuo. Flash chromatography (9:2:1-5:2:1 EtOAc: MeOH:H$_2$O) afforded product 58 (53 mg, 0.06 mmol, 49%). LRMS (ESI) calcd for C$_{27}$H$_{38}$N$_3$O$_{21}$P$_2$S (M$^-$) 834.13. found 834.26.

Example 48. Synthesis of 60

Sugar 58 (53 mg, 0.06 mmol) was dissolved in a mixture of degassed water:MeOH:Et$_3$N (3:7:3, 3 mL) and stirred until full deprotection was achieved according to LCMS. The reaction was concentrated under reduced pressure and purified on flash chromatography (7:2:1-3:2:1 EtOAc: MeOH:H$_2$O). One portion was stored, the other half was purified on anion exchange column (Q HITRAP, 1×5 mL column). First binding on the column was achieved via loading with buffer A (10 mM NaHCO$_3$) and the column was rinsed with 50 mL buffer A. Next, a gradient to 25% B (250 mM NaHCO$_3$) was performed to elute the product 60 (1 mg, 0.002 mmol, 5%).

LRMS (ESI−) calcd for C$_{19}$H$_{31}$N$_3$O$_{17}$P$_2$S (M$^-$) 666.08. found 666.0.

$^1$H-NMR (400 MHz, D$_2$O): δ 7.86 (d, J=8.0 Hz, 1H), 5.88-5.86 (m, 2H), 5.48-5.45 (m, 1H), 4.27-4.10 (m, 7H), 3.94-3.86 (m, 2H), 3.68-3.61 (m, 3H), 3.12-3.08 (m, 2H), 2.46-2.35 (m, 2H), 1.20-1.17 (m, 2H).

Example 49. Synthesis of 64

Acetylmercaptoacetic acid pentafluorophenol ester (100 mg, 0.33 mmol) was dissolved in CH$_2$Cl$_2$ (3 mL) and benzylamine (69 µL, 0.5 mmol) and Et$_3$N (44 µL, 0.40 mmol) were added. The mixture was stirred overnight and quenched by the addition of water (3 mL), followed by washing with water (3×3 mL). The organic layer was dried over Na$_2$SO$_4$, filtrated and concentrated in vacuo. Flash chromatography (EtOAc: heptane 1:4→1:1) afforded 61, which was dissolved in degassed methanol (7 mL). Subsequent degassed aqueous NaOH (1M, 3 mL) was added and the reaction was stirred under nitrogen atmosphere. After 2 h the reaction was quenched with 1 M HCl (10 mL) and CH$_2$Cl$_2$ (20 mL). The waterlayer was extracted with CH$_2$Cl$_2$ (2×30 mL), dried over Na$_2$SO$_4$, filtrated and concentrated in vacuo. The product 64 was used crude for the next reaction. $^1$H-NMR (400 MHz, CDCl$_3$): δ 7.28-7.70 (m, 5H), 6.94 (bs, 1H), 4.40 (d, J=5.6 Hz, 2H), 3.21 (d, J=9.2 Hz, 2H), 1.81 (t, J=9.2 Hz, 1H). LRMS (ESI+) calcd for C$_9$H$_{12}$NOS (M+H$^+$) 182.06. found 182.60.

Example 50. Synthesis of 65

Acetylmercapto-3-propanoic acid hydroxysuccinimide ester (100 mg, 0.41 mmol) was dissolved in CH$_2$Cl$_2$ (3 mL) and benzylamine (69 µL, 0.5 mmol) and Et$_3$N (44 µL, 0.40 mmol) were added. The mixture was stirred overnight and quenched by the addition of water (3 mL), followed by washing with water (3×3 mL). The organic layer was dried over Na$_2$SO$_4$, filtrated and concentrated in vacuo. Flash chromatography (EtOAc: heptane 1:4→1:1) afforded product 62, which was dissolved in degassed methanol (7 mL). Subsequent degassed aqueous NaOH (1 M, 3 mL) was added and the reaction was stirred under nitrogen atmosphere. After 2 h the reaction was quenched with 1 M HCl (10 mL) and CH$_2$Cl$_2$ (20 mL). The waterlayer was extracted with CH$_2$Cl$_2$ (2×30 mL), dried over Na$_2$SO$_4$, filtrated and concentrated in vacuo. The product 65 was used crude for the next reaction. LRMS (ESI+) calcd for C$_{10}$H$_{14}$NOS (M+H$^+$) 196.07. found 196.60.

Example 51. Synthesis of 66

Acetylmercapto-4-butanoic acid hydroxysuccinimide ester (100 mg, 0.38 mmol) was dissolved in CH$_2$Cl$_2$ (3 mL) and benzylamine (69 µL, 0.5 mmol) and Et$_3$N (44 µL, 0.40 mmol) were added. The mixture was stirred overnight and quenched by the addition of water (3 mL), followed by washing with water (3×3 mL). The organic layer was dried over Na$_2$SO$_4$, filtrated and concentrated in vacuo. Flash chromatography (EtOAc: heptane 1:4→1:1) afforded product 63, which was dissolved in degassed methanol (7 mL). Subsequent degassed aqueous NaOH (1M, 3 mL) was added and the reaction was stirred under nitrogen atmosphere. After 2 h, the reaction was quenched with 1 M HCl (10 mL) and CH$_2$Cl$_2$ (20 mL). The water-layer was extracted with CH$_2$Cl$_2$ (2×30 mL), dried over Na$_2$SO$_4$, filtrated and concentrated in vacuo. The product 66 was used crude for the next reaction. LRMS (ESI+) calcd for C$_{11}$H$_{16}$NOS (M+H$^+$) 210.09. found 210.60.

Example 52. Synthesis of Succinimide Adduct 67

To a solution of pyrene maleimide derivative 44 (10 mg, 0.02 mmol) in CH$_2$Cl$_2$ was added 64 (8 mg, 0.044 mmol) and Et$_3$N (10 µL, 0.09 mmol). After stirring for 1 h, the reaction was concentrated and flash chromatography (DCM→DCM:MeOH 9:1) afforded 67 (4 mg, 0.01 mmol, 28%). LRMS (ESI−) calcd for C$_{40}$H$_{43}$N$_4$O$_7$S (M+H$^+$) 723.28. found 723.31.

Example 53. Synthesis of Succinimide Adduct 68

To a solution of pyrene maleimide derivative 44 (10 mg, 0.02 mmol) in CH$_2$Cl$_2$ was added 65 (8 mg, 0.041 mmol) and Et$_3$N (10 µL, 0.09 mmol). After stirring for 1 h, the reaction was concentrated and flash chromatography (DCM→DCM:MeOH 9:1) afforded 68 (8 mg, 0.01 mmol, 54%). LRMS (ESI+) calcd for C$_{41}$H$_{45}$N$_4$O$_7$S (M+H$^+$) 737.29. found 736.29.

Example 54. Synthesis of Succinimide Adduct 69

To a solution of pyrene maleimide derivative 44 (10 mg, 0.02 mmol) in CH$_2$Cl$_2$ was added 66 (8 mg, 0.04 mmol) and Et$_3$N (10 µL, 0.09 mmol). After stirring for 1 h, the reaction was concentrated and flash chromatography (DCM→DCM: MeOH 9:1) afforded 69 (6 mg, 0.01 mmol, 40%). LRMS (ESI+) calcd for C$_{42}$H$_{47}$N$_4$O$_7$S (M+H$^+$) 751.31. found 751.38.

Example 55. Stability Studies of Succinimides 67-69

One of succinimide conjugates 67-69 (1 mg) was dissolved in DMF (400 µL) followed by the addition of buffer solution 1, 2 or 3 (800 µL). Buffer solution 1 is PBS, buffer solution 2 is PBS+1 mM glutathione (GSH, reduced) and buffer solution 3 is PBS+1 mM glutathione (oxidized). Final concentration of glutathione (through dilution with DMF) is 0.71 mM. The samples were incubated at 37° C. and measured in time. Ratio of products was determined by LC-MS.

TABLE 2

Relative ratio of starting succinimide (67-69) versus hydrolyzed succinimide versus glutathione adduct formed by reverse Michael, then GSH addition. Structures of compounds 67-69 are shown in FIG. 12.

| | 48 h Succin-imide | 48 h Hydro pro | 48 h GS adduct | 120 h Succin-imide | 120 h Hydro pro | 120 h GS adduct |
|---|---|---|---|---|---|---|
| 67 + buffer 1 | 57 | 43 | 0 | ND | ND | ND |
| 67 + buffer 2 | 41 | 18 | 41 | 3 | 38 | 52 |
| 67 + buffer 3 | 57 | 12 | 31 | 9 | 28 | 59 |
| 68 + buffer 1 | 79 | 21 | 0 | 47 | 53 | 0 |
| 68 + buffer 2 | 75 | 16 | 9 | 42 | 41 | 17 |
| 68 + buffer 3 | 80 | 13 | 7 | 49 | 35 | 16 |
| 69 + buffer 1 | 75 | 25 | 0 | 37 | 63 | 0 |
| 69 + buffer 2 | 79 | 14 | 6 | 49 | 39 | 12 |
| 69 + buffer 3 | 85 | 11 | 4 | 57 | 33 | 10 |

Example 56. Glycosyltransfer of UDP-Sugar 59 (GalNProSH) to Deglycosylated Trastuzumab Deglycosylated trastuzumab (10 mg/mL) was incubated with 59 (1.3 mM) and β (1,4)-Gal-T1(Y289L,C342T) (0.2 mg/mL) in 10 mM $MnCl_2$ and 50 mM Tris-HCl pH 6.0 for 16 hours at 30° C.

Next, the functionalized trastuzumab was incubated with protein A agarose (40 µL per mg IgG) for 1 hours at rt. The protein A agarose was washed three times with TBS (pH 6.0) and the IgG was eluted with 100 mM glycine-HCl pH 2.5. The eluted IgG was neutralized with 1 M Tris-HCl pH 7.0 and concentrated and washed with 50 mM Tris-HCl pH 6.0 using an Amicon Ultra-0.5, Ultracel-10 Membrane (Millipore) to a concentration of 15-20 mg/mL. Spectral analysis after digestion with Fabricator™ (50 U in 10 µL PBS pH 6.6) and subsequent wash with MiliQ using an Amicon Ultra-0.5, Ultracel-10 Membrane (Millipore) showed the formation of two products, the major product (24387 Da, expected mass 24388) of deglycosylated trastuzumab+GalNProSH (trastuzumab-(GalNProSH)$_2$) and the minor (25037 Da, expected mass 25038) of deglycosylated trastuzumab+GalNProS-UDPGalNProS disulfide. The ratio between the products is about 60:40.

Example 57. Glycosyltransfer of UDP-Sugar 60 (GalNBuSH) to Deglycosylated Trastuzumab Deglycosylated trastuzumab (10 mg/mL) was incubated with 60 (1.3 mM) and β(1,4)-Gal-T1(Y289M) (2 mg/mL) in 10 mM $MnCl_2$ and 50 mM Tris-HCl pH 6.0 for 16 hours at 30° C.

Spectral analysis after digestion with Fabricator™ (50 U in 10 µL PBS pH 6.6) and subsequent wash with MiliQ using an Amicon Ultra-0.5, Ultracel-10 Membrane (Millipore) showed 60% conversion of the starting material into two products, the minor product (24401 Da, expected mass 24402) of deglycosylated trastuzumab+GalNBuSH (trastuzumab-(GalNBuSH)$_2$) and the major (25066 Da, expected mass 25068) of deglycosylated trastuzumab+GalNBuS-UDPGalNBuS disulfide. The ratio between the products is about 20:80.

The invention claimed is:

1. A glycoprotein-conjugate comprising the formula:

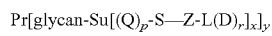

wherein:

Pr represents a protein;

glycan comprises the formula (101A) or (102A):

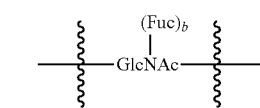

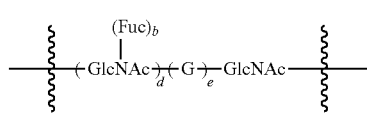

wherein G is a monosaccharide, or a linear or branched oligosaccharide comprising 2 to 20 sugar moieties;

b is 0 or 1;

d is 0 or 1; and e is 0 or 1;

Su is a sugar or a sugar derivative;

Q is —N(H)C(O)CH$_2$— or —CH$_2$—;

Z is a connecting group selected from -succinimide, —CH$_2$—C(O)—N(R$^9$)— and —C(=CH$_2$)—CH$_2$—C(O)—N(R$^9$)—, wherein the carbon atom is connected to and S and the nitrogen atom to L;

wherein R$^9$ is selected from the group consisting of L(D)$_r$, hydrogen, C$_1$-C$_{24}$ alkyl groups, C$_6$-C$_{24}$ aryl groups, C$_7$-C$_{24}$ alkylaryl groups and C$_7$-C$_{24}$ arylalkyl groups, wherein said C$_1$-C$_{24}$ alkyl groups, C$_6$-C$_{24}$ aryl groups, C$_7$-C$_{24}$ alkylaryl groups and C$_7$-C$_{24}$ arylalkyl groups are optionally substituted;

L is a linker;

D is a molecule of interest;

p is 0 or 1;

r is 1 to 20;

x is 1, 2, 3, or 4; and y is 1 to 20.

2. The glycoprotein-conjugate of claim 1, wherein said glycoprotein conjugate comprises the formula (121) or (122):

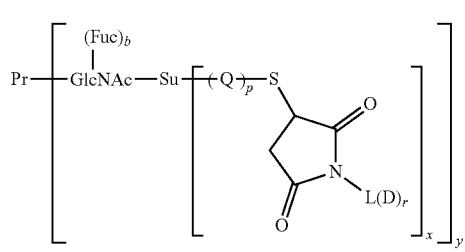

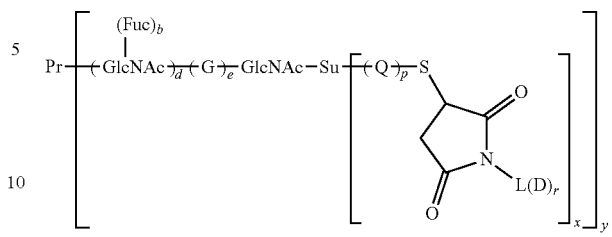

wherein: Pr, L, D, r, x, y, b, d, e, p, Q, Su, and G are as defined in claim 1.

3. The glycoprotein-conjugate of claim 1, wherein said glycoprotein conjugate comprises the formula (123) or (124):

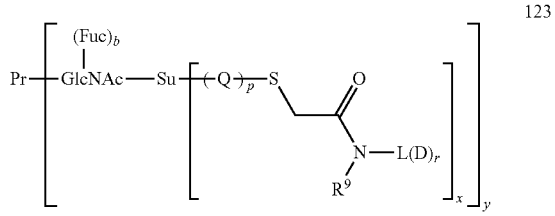

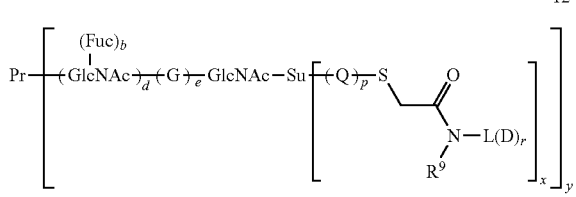

wherein: Pr, L, D, r, x, y, b, d, e, p, Q, Su, G, and R$^9$ are as defined in claim 1.

4. The glycoprotein-conjugate of claim 1, wherein said glycoprotein conjugate comprises the formula (125) or (126):

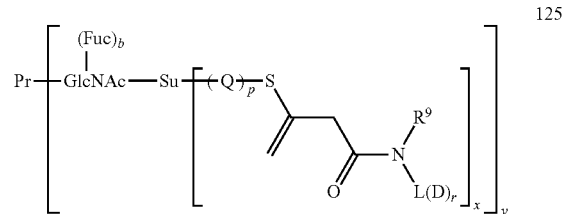

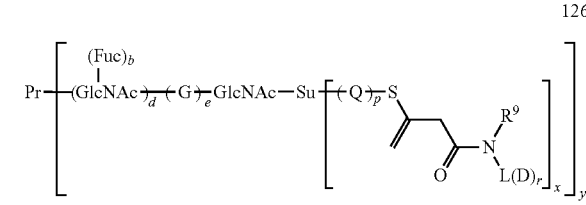

wherein: Pr, L, D, r, x, y, b, d, e, p, Q, Su, G, and R$^9$ are as defined in claim 1.

5. The glycoprotein-conjugate of claim 1, wherein said glycoprotein conjugate is an antibody-conjugate.

6. The antibody-conjugate of claim 5, wherein said antibody-conjugate comprises a monoclonal antibody.

7. The antibody-conjugate of claim 5, wherein D is a pharmaceutically active substance.

8. A pharmaceutical composition comprising the antibody conjugate of claim 5 and a pharmaceutically acceptable excipient.

9. A process for the preparation of the glycoprotein-conjugate of claim 1, said process comprising:
  contacting a glycoprotein comprising the formula Pr-[glycan]$_y$ with a nucleotide-sugar derivative in the presence of a catalyst to provide a modified glycoprotein comprising the formula Pr-[glycan-Su(A)$_x$]$_y$;
  wherein Pr is as defined in claim 1;
  wherein said glycan comprises the formula (101) or (102):

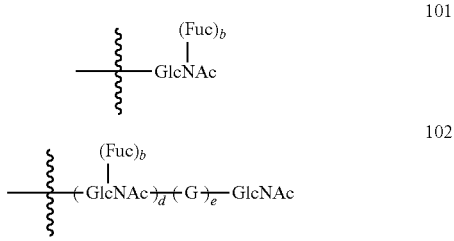

wherein G, b, d, and e are as defined in claim 1,
  wherein said catalyst is selected from the group consisting of β(1,4)-galactosyltransferases, β(1,3)-N-galactosyltransferases, β(1,4)-galactosyltransferases comprising a mutant catalytic domain and β(1,3)-N-galactosyltransferases comprising a mutant catalytic domain,
  wherein said nucleotide-sugar derivative comprises the formula Su(A)$_x$-P, wherein x is as defined in claim 1,
  A is a functional group independently selected at each occurrence from the group consisting of a thiol group or a precursor thereof, a halogen, a sulfonyloxy group, a halogenated acetamido group, a mercaptoacetamido group and a sulfonated hydroxyl acetamido group, and
  P is a nucleotide;
  reacting said modified glycoprotein with a linker-conjugate comprising the formula B-L-(D)$_r$;
  wherein B is a functional group capable of reacting with said functional group A; and L, D, and r are as defined in claim 1;
  thereby producing said glycoprotein-conjugate of claim 1.

10. The process of claim 9, wherein said catalyst is selected from the group consisting of a β(1,4)-galactosyltransferases comprising a mutant catalytic domain and a β(1,3)-galactosyltransferases comprising a mutant catalytic domain.

11. The process of claim 9, wherein said catalyst comprises a mutant catalytic domain from a β(1,4)-galactosyltransferase selected from the group consisting of bovine β(1,4)-Gal-T1 GalT Y289L, GalT Y289N, GalT Y289I, GalT Y289F, GalT Y289M, GalT Y289V, GalT, Y289G and GalT Y289A.

12. The process of claim 9, wherein said glycoprotein-conjugate is an antibody-conjugate.

13. The process of claim 9, further comprising providing a glycoprotein comprising a terminal GlcNAc-moiety at the non-reducing end.

14. The process of claim 9, wherein:
  (a) when said modified glycoprotein is a halogen-modified glycoprotein or a halogenated acetamido-modified glycoprotein, functional group B comprises a thiol group, an alcohol group or an amine group;
  (b) when said modified glycoprotein is a thiol-modified glycoprotein or a mercaptoacetamido modified glycoprotein, functional group B comprises an N-maleimide group or a halogenate acetamido group or an alkene group; or
  (c) when said modified glycoprotein is a sulfonyloxy-modified glycoprotein or a sulfonated hydroxyacetamido-modified glycoprotein, functional group B comprises a thiol group, an alcohol group or an amine group.

15. The process of claim 9, wherein said glycoprotein is a thiol-modified glycoprotein or a mercaptoacetamido-modified glycoprotein, and functional group B comprises an alleneamide group.

* * * * *